(12) United States Patent
Hu et al.

(10) Patent No.: US 12,390,565 B2
(45) Date of Patent: Aug. 19, 2025

(54) DIALYSIS SYSTEMS AND METHODS

(71) Applicant: OUTSET MEDICAL, INC., San Jose, CA (US)

(72) Inventors: Dean Hu, San Leandro, CA (US); Justin Thomas Puzin, Los Gatos, CA (US); Steven Owen Miller, Livermore, CA (US); Tyler John Miller, Danville, CA (US); Logan Rivas, San Jose, CA (US); Michael Kim, San Jose, CA (US); Michael Edward Hogard, Odessa, FL (US); Jeffrey Etter, Hayward, CA (US); Todd Nelson, San Jose, CA (US); James Tumber, San Jose, CA (US); Stephanie Klunk, San Jose, CA (US); Paul Brayford, San Jose, CA (US); Cole Naymark, San Jose, CA (US)

(73) Assignee: Outset Medical, Inc., San Jose, CA (US)

( * ) Notice: Subject to any disclaimer, the term of this patent is extended or adjusted under 35 U.S.C. 154(b) by 728 days.

(21) Appl. No.: 17/607,637

(22) PCT Filed: Apr. 30, 2020

(86) PCT No.: PCT/US2020/030751
§ 371 (c)(1),
(2) Date: Oct. 29, 2021

(87) PCT Pub. No.: WO2020/223500
PCT Pub. Date: Nov. 5, 2020

(65) Prior Publication Data
US 2022/0203004 A1    Jun. 30, 2022

Related U.S. Application Data

(60) Provisional application No. 62/933,752, filed on Nov. 11, 2019, provisional application No. 62/841,051, filed on Apr. 30, 2019.

(51) Int. Cl.
*A61M 1/16* (2006.01)
*A61M 1/36* (2006.01)

(52) U.S. Cl.
CPC ........ *A61M 1/1656* (2013.01); *A61M 1/1678* (2013.01); *A61M 1/362227* (2022.05);
(Continued)

(58) Field of Classification Search
CPC .. A61M 1/1656; A61M 1/1668; A61M 1/155; A61M 1/1666; A61M 1/28
See application file for complete search history.

(56) References Cited

U.S. PATENT DOCUMENTS

| 1,662,870 A | 3/1928 | Stancliffe |
| 3,356,360 A | 12/1967 | Ward |

(Continued)

FOREIGN PATENT DOCUMENTS

| CA | 2297271 C | 8/2008 |
| CA | 2830085 A1 | 9/2012 |

(Continued)

OTHER PUBLICATIONS

Allis et al., "Chapter 16: Nanostructural Architectures from Molecular Building Blocks," in Handbook of Nanoscience, Engineering, and Technology, 1st Edition (Electrical Engineering Handbook), CRC Press LLC, Boca Raton, FL, Chapter 16 (70 pgs.), Oct. 2002.

(Continued)

*Primary Examiner* — Susan S Su
*Assistant Examiner* — Erin A Kim
(74) *Attorney, Agent, or Firm* — Shay Glenn LLP

(57) ABSTRACT

Dialysis systems and methods are described which can include a number of features. The dialysis systems described can be to provide dialysis therapy to a patient in the comfort of their own home. The dialysis system can be configured to prepare purified water from a tap water source in real-time (Continued)

that is used for creating a dialysate solution. The dialysis systems described also include features that make it easy for a patient to self-administer therapy.

15 Claims, 45 Drawing Sheets

(52) U.S. Cl.
CPC .... *A61M 1/36224* (2022.05); *A61M 1/36225* (2022.05); *A61M 1/3627* (2013.01); *A61M 1/3641* (2014.02); *A61M 1/36226* (2022.05); *A61M 1/362262* (2022.05); *A61M 1/362265* (2022.05); *A61M 1/362266* (2022.05); *A61M 2205/3317* (2013.01); *A61M 2205/3324* (2013.01); *A61M 2205/3334* (2013.01); *A61M 2205/702* (2013.01); *A61M 2205/707* (2013.01)

(56) References Cited

U.S. PATENT DOCUMENTS

| | | | |
|---|---|---|---|
| 3,695,445 A | 10/1972 | Esmond | |
| 3,710,237 A | 1/1973 | Watson et al. | |
| 3,762,032 A | 10/1973 | Bowling et al. | |
| 3,809,309 A | 5/1974 | Batista | |
| 3,827,563 A | 8/1974 | Boe et al. | |
| 3,965,008 A | 6/1976 | Dawson | |
| 4,080,295 A | 3/1978 | Riede | |
| 4,089,456 A | 5/1978 | Toppen et al. | |
| 4,100,068 A | 7/1978 | Jordan et al. | |
| 4,110,220 A | 8/1978 | Lavender | |
| 4,115,273 A | 9/1978 | Winstead | |
| 4,155,157 A | 5/1979 | Gersbacher | |
| 4,172,033 A | 10/1979 | Willock | |
| 4,194,014 A | 3/1980 | Hermans et al. | |
| 4,204,628 A | 5/1980 | Houston et al. | |
| 4,209,391 A | 6/1980 | Lipps | |
| 4,229,299 A | 10/1980 | Savitz et al. | |
| 4,231,366 A | 11/1980 | Schael | |
| 4,267,040 A | 5/1981 | Schal | |
| 4,293,409 A | 10/1981 | Riede et al. | |
| 4,310,416 A | 1/1982 | Tanaka et al. | |
| 4,317,725 A | 3/1982 | Kume et al. | |
| 4,342,651 A | 8/1982 | Ahrens | |
| 4,476,022 A | 10/1984 | Doll | |
| 4,486,303 A | 12/1984 | Brous | |
| 4,500,426 A | 2/1985 | Ishii et al. | |
| 4,508,622 A | 4/1985 | Polaschegg | |
| 4,536,201 A | 8/1985 | Brorsson et al. | |
| 4,560,472 A | 12/1985 | Granzow et al. | |
| 4,624,784 A | 11/1986 | Lefebvre | |
| 4,647,748 A | 3/1987 | Glassman | |
| 4,661,246 A | 4/1987 | Ash | |
| 4,689,108 A | 8/1987 | Barry, Jr. et al. | |
| 4,711,715 A | 12/1987 | Polaschegg | |
| 4,756,835 A | 7/1988 | Wilson | |
| 4,769,134 A | 9/1988 | Allan et al. | |
| 4,770,787 A | 9/1988 | Heath et al. | |
| 4,773,991 A | 9/1988 | Aid | |
| 4,784,495 A * | 11/1988 | Jonsson | A61M 1/1666 366/151.1 |
| 4,786,411 A | 11/1988 | Benattar et al. | |
| 4,827,430 A | 5/1989 | Aid et al. | |
| 4,828,543 A | 5/1989 | Weiss et al. | |
| 4,869,421 A | 9/1989 | Norris et al. | |
| 4,875,619 A | 10/1989 | Anderson et al. | |
| 4,889,635 A | 12/1989 | Chevallet | |
| 4,894,164 A | 1/1990 | Polaschegg | |
| 4,923,613 A | 5/1990 | Chevallet | |
| 4,925,056 A | 5/1990 | McCoig | |
| 4,940,455 A | 7/1990 | Guinn | |
| 5,087,930 A | 2/1992 | Roy et al. | |
| 5,092,836 A | 3/1992 | Polaschegg | |
| 5,094,749 A | 3/1992 | Seita et al. | |
| 5,120,303 A | 6/1992 | Hombrouckx | |
| 5,147,605 A | 9/1992 | Tatsuno et al. | |
| 5,227,049 A | 7/1993 | Chevallet et al. | |
| 5,232,145 A | 8/1993 | Alley et al. | |
| 5,236,476 A | 8/1993 | Klick | |
| 5,247,434 A | 9/1993 | Peterson et al. | |
| 5,259,961 A | 11/1993 | Eigendorf | |
| 5,312,550 A | 5/1994 | Hester | |
| 5,313,023 A | 5/1994 | Johnson | |
| 5,316,676 A | 5/1994 | Drori | |
| 5,326,476 A | 7/1994 | Grogan et al. | |
| 5,336,165 A | 8/1994 | Twardowski | |
| 5,342,326 A | 8/1994 | Peppel et al. | |
| 5,344,392 A | 9/1994 | Senninger et al. | |
| 5,346,472 A | 9/1994 | Keshaviah et al. | |
| 5,360,395 A | 11/1994 | Utterberg | |
| 5,385,623 A | 1/1995 | Diaz | |
| 5,394,732 A | 3/1995 | Johnson et al. | |
| 5,395,351 A | 3/1995 | Munsch | |
| 5,401,238 A | 3/1995 | Pirazzoli | |
| 5,409,612 A | 4/1995 | Maltais et al. | |
| 5,421,208 A | 6/1995 | Packard et al. | |
| 5,439,451 A | 8/1995 | Collinson et al. | |
| 5,469,264 A | 11/1995 | Shigemori | |
| 5,472,614 A | 12/1995 | Rossi | |
| 5,489,385 A | 2/1996 | Raabe et al. | |
| 5,498,253 A | 3/1996 | Aswad et al. | |
| 5,498,338 A | 3/1996 | Kruger et al. | |
| 5,503,624 A | 4/1996 | Roeher et al. | |
| 5,520,640 A | 5/1996 | Utterberg | |
| 5,526,357 A | 6/1996 | Jandrell | |
| 5,529,685 A | 6/1996 | Irie et al. | |
| 5,533,996 A | 7/1996 | Murphey et al. | |
| 5,534,328 A | 7/1996 | Ashmead et al. | |
| 5,536,258 A | 7/1996 | Folden | |
| 5,580,460 A | 12/1996 | Polaschegg | |
| 5,580,523 A | 12/1996 | Bard | |
| 5,582,600 A | 12/1996 | Loh | |
| 5,591,016 A | 1/1997 | Kubota et al. | |
| 5,591,344 A | 1/1997 | Kenley et al. | |
| 5,593,581 A | 1/1997 | Lescoche | |
| 5,595,712 A | 1/1997 | Harbster et al. | |
| 5,609,770 A | 3/1997 | Zimmerman et al. | |
| 5,610,645 A | 3/1997 | Moore et al. | |
| 5,611,214 A | 3/1997 | Wegeng et al. | |
| 5,613,663 A | 3/1997 | Schmidt et al. | |
| 5,615,996 A | 4/1997 | Suzuki et al. | |
| 5,616,305 A * | 4/1997 | Mathieu | B01F 35/50 422/267 |
| 5,618,268 A | 4/1997 | Raines et al. | |
| 5,618,441 A | 4/1997 | Rosa et al. | |
| 5,620,608 A | 4/1997 | Rosa et al. | |
| 5,623,969 A | 4/1997 | Raines | |
| 5,624,572 A | 4/1997 | Larson et al. | |
| 5,629,871 A | 5/1997 | Love et al. | |
| 5,630,804 A | 5/1997 | Imada et al. | |
| 5,643,190 A | 7/1997 | Utterberg | |
| 5,647,984 A | 7/1997 | Hovland et al. | |
| 5,648,684 A | 7/1997 | Bertin et al. | |
| 5,650,071 A | 7/1997 | Brugger et al. | |
| 5,662,144 A | 9/1997 | Lo et al. | |
| 5,685,835 A | 11/1997 | Brugger | |
| 5,689,966 A | 11/1997 | Zess et al. | |
| 5,693,008 A | 12/1997 | Brugger et al. | |
| 5,698,916 A | 12/1997 | Eguchi | |
| 5,711,883 A | 1/1998 | Folden et al. | |
| 5,713,850 A | 2/1998 | Heilmann et al. | |
| 5,725,773 A | 3/1998 | Polaschegg | |
| 5,743,892 A | 4/1998 | Loh et al. | |
| 5,744,031 A | 4/1998 | Bene | |
| 5,749,226 A | 5/1998 | Bowman et al. | |
| 5,769,985 A | 6/1998 | Kawakami et al. | |
| 5,779,833 A | 7/1998 | Cawley et al. | |
| 5,782,575 A | 7/1998 | Vincent et al. | |
| 5,788,099 A | 8/1998 | Treu et al. | |
| 5,788,851 A | 8/1998 | Kenley et al. | |
| 5,792,367 A | 8/1998 | Mattisson et al. | |
| 5,811,062 A | 9/1998 | Wegeng et al. | |

(56) References Cited

U.S. PATENT DOCUMENTS

| | | |
|---|---|---|
| 5,813,235 A | 9/1998 | Peterson |
| 5,851,202 A | 12/1998 | Carlsson |
| 5,858,238 A | 1/1999 | Mcrea et al. |
| 5,858,239 A | 1/1999 | Kenley et al. |
| 5,861,555 A | 1/1999 | Hobro et al. |
| 5,868,930 A | 2/1999 | Kopf |
| 5,879,316 A | 3/1999 | Safar et al. |
| 5,881,774 A | 3/1999 | Utterberg |
| 5,885,456 A | 3/1999 | Charkoudian et al. |
| 5,895,368 A | 4/1999 | Utterberg |
| 5,903,211 A | 5/1999 | Flego et al. |
| 5,910,138 A | 6/1999 | Sperko et al. |
| 5,914,033 A | 6/1999 | Carlsson |
| 5,921,678 A | 7/1999 | Desai et al. |
| 5,928,177 A | 7/1999 | Brugger et al. |
| 5,928,180 A | 7/1999 | Krivitski et al. |
| 5,932,103 A | 8/1999 | Kenley et al. |
| 5,932,940 A | 8/1999 | Epstein et al. |
| 5,938,634 A | 8/1999 | Packard |
| 5,938,938 A | 8/1999 | Bosetto et al. |
| 5,951,863 A | 9/1999 | Kruger et al. |
| 5,951,870 A | 9/1999 | Utterberg |
| 5,957,898 A | 9/1999 | Jepson et al. |
| 5,974,867 A | 11/1999 | Forster et al. |
| 5,976,115 A | 11/1999 | Paris et al. |
| 5,983,947 A | 11/1999 | Utterberg |
| 5,984,903 A | 11/1999 | Nadal |
| 5,993,174 A | 11/1999 | Konishi |
| 6,003,556 A | 12/1999 | Brugger et al. |
| 6,010,623 A | 1/2000 | Schnell et al. |
| 6,024,276 A | 2/2000 | Hirata et al. |
| 6,032,926 A | 3/2000 | Fuchs |
| 6,036,680 A | 3/2000 | Horne et al. |
| 6,036,858 A * | 3/2000 | Carlsson ............ A61M 1/1666 604/4.01 |
| 6,039,877 A | 3/2000 | Chevallet et al. |
| 6,041,801 A | 3/2000 | Gray et al. |
| 6,044,691 A | 4/2000 | Kenley et al. |
| 6,048,432 A | 4/2000 | Ecer |
| 6,058,934 A | 5/2000 | Sullivan |
| 6,064,797 A | 5/2000 | Crittendon et al. |
| 6,066,261 A | 5/2000 | Spickermann |
| 6,071,269 A | 6/2000 | Schnell et al. |
| 6,074,559 A | 6/2000 | Hahmann et al. |
| 6,077,443 A | 6/2000 | Goldau |
| 6,082,891 A | 7/2000 | Schubert et al. |
| 6,100,463 A | 8/2000 | Ladd et al. |
| 6,109,994 A | 8/2000 | Cho et al. |
| 6,113,785 A | 9/2000 | Miura et al. |
| 6,117,115 A | 9/2000 | Hill et al. |
| 6,117,123 A | 9/2000 | Barney et al. |
| 6,121,539 A | 9/2000 | Johnson et al. |
| 6,123,798 A | 9/2000 | Gandhi et al. |
| 6,126,723 A | 10/2000 | Drost et al. |
| 6,126,831 A | 10/2000 | Goldau et al. |
| 6,129,973 A | 10/2000 | Martin et al. |
| 6,132,616 A | 10/2000 | Twardowski et al. |
| 6,139,754 A | 10/2000 | Hartranft et al. |
| 6,142,008 A | 11/2000 | Cole et al. |
| 6,143,181 A | 11/2000 | Falkvall et al. |
| 6,143,247 A | 11/2000 | Sheppard et al. |
| 6,148,635 A | 11/2000 | Beebe et al. |
| 6,153,102 A | 11/2000 | Kenley et al. |
| 6,165,149 A | 12/2000 | Utterberg et al. |
| 6,165,161 A | 12/2000 | York et al. |
| 6,167,910 B1 | 1/2001 | Chow |
| 6,187,198 B1 | 2/2001 | Utterberg |
| 6,187,199 B1 | 2/2001 | Goldau |
| 6,192,596 B1 | 2/2001 | Bennett et al. |
| 6,193,462 B1 | 2/2001 | Kubota |
| 6,202,312 B1 | 3/2001 | Rando |
| 6,203,522 B1 | 3/2001 | Holmberg et al. |
| 6,203,535 B1 | 3/2001 | Barney et al. |
| 6,212,333 B1 | 4/2001 | Olk et al. |
| 6,220,299 B1 | 4/2001 | Arvidsson et al. |
| 6,221,040 B1 | 4/2001 | Kleinekofort |
| 6,221,064 B1 | 4/2001 | Nadal |
| 6,223,130 B1 | 4/2001 | Gray et al. |
| 6,225,497 B1 | 5/2001 | Becker et al. |
| 6,234,773 B1 | 5/2001 | Hill et al. |
| 6,251,279 B1 | 6/2001 | Peterson et al. |
| 6,254,567 B1 | 7/2001 | Treu et al. |
| 6,254,754 B1 | 7/2001 | Ross et al. |
| 6,258,276 B1 | 7/2001 | Mika et al. |
| 6,261,282 B1 | 7/2001 | Jepson et al. |
| 6,277,277 B1 | 8/2001 | Jacobi et al. |
| 6,280,406 B1 | 8/2001 | Dolecek et al. |
| 6,284,141 B1 | 9/2001 | Shaldon et al. |
| 6,302,653 B1 | 10/2001 | Bryant et al. |
| 6,308,721 B1 | 10/2001 | Bock et al. |
| 6,309,673 B1 | 10/2001 | Duponchelle et al. |
| 6,322,551 B1 | 11/2001 | Brugger |
| 6,323,662 B2 | 11/2001 | Ferri |
| 6,325,774 B1 | 12/2001 | Bene et al. |
| 6,329,139 B1 | 12/2001 | Nova et al. |
| 6,331,252 B1 | 12/2001 | El Sayyid et al. |
| 6,334,301 B1 | 1/2002 | Otsap et al. |
| 6,343,614 B1 | 2/2002 | Gray et al. |
| 6,344,033 B1 | 2/2002 | Jepson et al. |
| 6,346,084 B1 | 2/2002 | Schnell et al. |
| 6,347,711 B1 | 2/2002 | Goebel et al. |
| 6,349,170 B1 | 2/2002 | Fressinet et al. |
| 6,350,260 B1 | 2/2002 | Goebel et al. |
| 6,355,161 B1 | 3/2002 | Shah et al. |
| 6,357,332 B1 | 3/2002 | Vecchio |
| 6,361,201 B1 * | 3/2002 | Russell ............ B01F 25/312 366/144 |
| 6,365,041 B1 | 4/2002 | Hoadley |
| 6,368,505 B1 | 4/2002 | Grummert et al. |
| 6,375,871 B1 | 4/2002 | Bentsen et al. |
| 6,382,923 B1 | 5/2002 | Gray |
| 6,387,069 B1 | 5/2002 | Utterberg |
| 6,395,180 B2 | 5/2002 | Chioini et al. |
| 6,415,860 B1 | 7/2002 | Kelly et al. |
| 6,416,293 B1 | 7/2002 | Bouchard et al. |
| 6,423,022 B1 | 7/2002 | Rocher et al. |
| 6,432,309 B1 | 8/2002 | Fuke et al. |
| 6,454,736 B1 | 9/2002 | Ludt et al. |
| 6,454,942 B1 | 9/2002 | Shintani et al. |
| 6,468,056 B1 | 10/2002 | Murakoshi |
| 6,477,058 B1 | 11/2002 | Luebs et al. |
| 6,481,982 B1 | 11/2002 | Yokomichi |
| 6,485,263 B1 | 11/2002 | Bryant et al. |
| 6,488,842 B2 | 12/2002 | Nagaoka |
| 6,488,872 B1 | 12/2002 | Beebe et al. |
| 6,503,062 B1 | 1/2003 | Gray et al. |
| 6,514,225 B1 | 2/2003 | Utterberg et al. |
| 6,514,412 B1 | 2/2003 | Insley et al. |
| 6,526,357 B1 | 2/2003 | Soussan et al. |
| 6,527,728 B2 | 3/2003 | Zhang |
| 6,530,262 B1 | 3/2003 | Esser |
| 6,536,742 B2 | 3/2003 | Lotz et al. |
| 6,537,506 B1 | 3/2003 | Schwalbe et al. |
| 6,544,229 B1 | 4/2003 | Danby et al. |
| 6,546,998 B2 | 4/2003 | Oh et al. |
| 6,554,789 B1 | 4/2003 | Brugger et al. |
| 6,572,576 B2 | 6/2003 | Brugger et al. |
| 6,572,641 B2 | 6/2003 | Brugger et al. |
| 6,575,927 B1 | 6/2003 | Weitzel et al. |
| 6,579,241 B2 | 6/2003 | Roeher |
| 6,579,253 B1 | 6/2003 | Burbank et al. |
| 6,581,906 B2 | 6/2003 | Pott et al. |
| 6,582,385 B2 | 6/2003 | Burbank et al. |
| 6,592,558 B2 | 7/2003 | Quah |
| 6,601,432 B1 | 8/2003 | Ericson et al. |
| 6,602,424 B1 | 8/2003 | Krämer et al. |
| 6,604,908 B1 | 8/2003 | Bryant et al. |
| 6,607,644 B1 | 8/2003 | Apffel, Jr. |
| 6,607,697 B1 | 8/2003 | Müller |
| 6,616,877 B2 | 9/2003 | Close et al. |
| 6,616,909 B1 | 9/2003 | Tonkovich et al. |
| 6,623,860 B2 | 9/2003 | Hu et al. |
| 6,630,068 B1 | 10/2003 | Vinci |
| 6,635,226 B1 | 10/2003 | Tso et al. |

(56) References Cited

U.S. PATENT DOCUMENTS

| | | |
|---|---|---|
| 6,640,611 B2 | 11/2003 | Ericson et al. |
| 6,649,046 B2 | 11/2003 | Chevallet |
| 6,649,063 B2 | 11/2003 | Brugger et al. |
| 6,652,627 B1 | 11/2003 | Tonkovich et al. |
| 6,653,841 B1 | 11/2003 | Koerdt et al. |
| 6,654,660 B1 | 11/2003 | Singh et al. |
| 6,666,840 B1 | 12/2003 | Falkvall et al. |
| 6,666,909 B1 | 12/2003 | Tegrotenhuis et al. |
| 6,672,502 B1 | 1/2004 | Paul et al. |
| 6,673,311 B1 | 1/2004 | Sotoyama et al. |
| 6,676,621 B1 | 1/2004 | Menninger |
| 6,676,835 B2 | 1/2004 | O'Connor et al. |
| 6,684,710 B2 | 2/2004 | Chevallet et al. |
| 6,685,831 B2 | 2/2004 | Dönig et al. |
| 6,686,946 B2 | 2/2004 | Masuda et al. |
| 6,688,381 B2 | 2/2004 | Pence et al. |
| 6,695,807 B2 | 2/2004 | Bell et al. |
| 6,716,356 B2 | 4/2004 | Collins et al. |
| 6,730,233 B2 | 5/2004 | Pedrazzi |
| 6,731,216 B2 | 5/2004 | Ho et al. |
| 6,733,676 B2 | 5/2004 | Takai |
| 6,736,789 B1 | 5/2004 | Spickermann |
| 6,738,052 B1 | 5/2004 | Manke et al. |
| 6,743,193 B2 | 6/2004 | Brugger et al. |
| 6,744,038 B2 | 6/2004 | Wang et al. |
| 6,746,514 B2 | 6/2004 | Bedingfield et al. |
| 6,749,814 B1 | 6/2004 | Bergh et al. |
| 6,767,333 B1 | 7/2004 | Müller et al. |
| 6,775,577 B2 | 8/2004 | Cmkovich et al. |
| 6,793,831 B1 | 9/2004 | Paul et al. |
| 6,797,056 B2 | 9/2004 | David |
| 6,804,991 B2 | 10/2004 | Balschat et al. |
| 6,806,947 B1 | 10/2004 | Ekdahl et al. |
| 6,811,707 B2 | 11/2004 | Rovatti et al. |
| 6,814,547 B2 | 11/2004 | Childers et al. |
| 6,814,726 B1 | 11/2004 | Lauer |
| 6,814,859 B2 | 11/2004 | Koehler et al. |
| 6,818,179 B1 | 11/2004 | Edgson et al. |
| 6,821,432 B2 | 11/2004 | Metzner |
| 6,827,698 B1 | 12/2004 | Kleinekofort |
| 6,830,693 B2 | 12/2004 | Govoni et al. |
| 6,838,156 B1 | 1/2005 | Neyer et al. |
| 6,852,231 B2 | 2/2005 | Ivansons et al. |
| 6,858,137 B2 | 2/2005 | Hahmann et al. |
| 6,863,867 B2 | 3/2005 | Vanden Bussche et al. |
| 6,868,309 B1 | 3/2005 | Begelman |
| 6,869,538 B2 | 3/2005 | Yu et al. |
| 6,871,838 B2 | 3/2005 | Raines et al. |
| 6,877,713 B1 | 4/2005 | Gray et al. |
| 6,878,283 B2 | 4/2005 | Thompson |
| 6,880,034 B2 | 4/2005 | Manke et al. |
| 6,881,344 B2 | 4/2005 | Vasta et al. |
| 6,889,556 B2 | 5/2005 | Steger |
| 6,892,781 B2 | 5/2005 | Mcherron et al. |
| 6,903,332 B2 | 6/2005 | Weiss et al. |
| 6,905,479 B1 | 6/2005 | Bouchard et al. |
| 6,911,262 B2 | 6/2005 | Sallavanti et al. |
| 6,913,877 B1 | 7/2005 | Chaplen et al. |
| 6,929,751 B2 | 8/2005 | Bowman, Jr. et al. |
| 6,936,031 B2 | 8/2005 | Caleffi |
| 6,939,111 B2 | 9/2005 | Huitt et al. |
| 6,939,471 B2 | 9/2005 | Gross et al. |
| 6,952,963 B2 | 10/2005 | Delnevo |
| 6,953,323 B2 | 10/2005 | Childers et al. |
| 6,955,655 B2 | 10/2005 | Burbank et al. |
| 6,967,002 B1 | 11/2005 | Edgson et al. |
| 6,974,301 B2 | 12/2005 | Suzuki et al. |
| 6,976,964 B2 | 12/2005 | Chevallet et al. |
| 6,979,309 B2 | 12/2005 | Burbank et al. |
| 6,981,522 B2 | 1/2006 | O'Connor et al. |
| 6,986,428 B2 | 1/2006 | Hester et al. |
| 6,989,134 B2 | 1/2006 | Tonkovich et al. |
| 6,994,829 B2 | 2/2006 | Whyatt et al. |
| 7,004,924 B1 | 2/2006 | Brugger et al. |
| 7,014,705 B2 | 3/2006 | David |
| 7,021,148 B2 | 4/2006 | Kuhn et al. |
| 7,022,098 B2 | 4/2006 | Wariar et al. |
| 7,029,456 B2 | 4/2006 | Ware et al. |
| 7,033,498 B2 | 4/2006 | Wong |
| 7,033,539 B2 | 4/2006 | Krensky et al. |
| 7,040,142 B2 | 5/2006 | Burbank |
| 7,044,432 B2 | 5/2006 | Beden et al. |
| 7,044,927 B2 | 5/2006 | Mueller et al. |
| 7,063,512 B2 | 6/2006 | Haesloop et al. |
| 7,070,589 B2 | 7/2006 | Lolachi et al. |
| 7,074,191 B2 | 7/2006 | Bosetto et al. |
| 7,087,033 B2 | 8/2006 | Brugger et al. |
| 7,087,036 B2 | 8/2006 | Busby et al. |
| 7,094,345 B2 | 8/2006 | Gilbert et al. |
| 7,112,273 B2 | 9/2006 | Weigel et al. |
| 7,114,701 B2 | 10/2006 | Peppel |
| 7,115,206 B2 | 10/2006 | Chevallet et al. |
| 7,115,228 B2 | 10/2006 | Lundiveit et al. |
| 7,118,920 B2 | 10/2006 | Brophy et al. |
| 7,121,815 B2 | 10/2006 | Knuth et al. |
| 7,122,149 B2 | 10/2006 | Li et al. |
| 7,122,156 B2 | 10/2006 | Bergh et al. |
| 7,125,540 B1 | 10/2006 | Wegeng et al. |
| 7,131,956 B1 | 11/2006 | Pirazzoli et al. |
| 7,147,615 B2 | 12/2006 | Wariar et al. |
| 7,150,815 B2 | 12/2006 | Ashmead et al. |
| 7,152,469 B2 | 12/2006 | Milleker et al. |
| 7,163,531 B2 | 1/2007 | Seese et al. |
| 7,166,084 B2 | 1/2007 | Utterberg |
| 7,168,334 B1 | 1/2007 | Drott |
| 7,170,591 B2 | 1/2007 | Ohishi et al. |
| 7,175,697 B2 | 2/2007 | Neri |
| 7,186,342 B2 | 3/2007 | Pirazzoli et al. |
| 7,188,151 B2 | 3/2007 | Kumar et al. |
| 7,211,442 B2 | 5/2007 | Gilbert et al. |
| 7,214,312 B2 | 5/2007 | Brugger et al. |
| 7,217,108 B2 | 5/2007 | Herwig et al. |
| 7,217,364 B2 | 5/2007 | Lauer et al. |
| 7,223,262 B2 | 5/2007 | Brehm et al. |
| 7,223,338 B2 | 5/2007 | Duchamp et al. |
| 7,232,418 B2 | 6/2007 | Neri et al. |
| 7,238,164 B2 | 7/2007 | Childers et al. |
| 7,247,146 B2 | 7/2007 | Tonelli et al. |
| 7,279,134 B2 | 10/2007 | Chan et al. |
| 7,291,123 B2 | 11/2007 | Baraldi et al. |
| 7,306,197 B2 | 12/2007 | Parrino et al. |
| 7,314,061 B2 | 1/2008 | Peppel |
| 7,316,780 B1 | 1/2008 | Fendya et al. |
| 7,337,674 B2 | 3/2008 | Burbank et al. |
| 7,341,568 B2 | 3/2008 | Zhang |
| 7,354,426 B2 | 4/2008 | Young |
| 7,355,685 B2 | 4/2008 | Scibona et al. |
| 7,378,280 B2 | 5/2008 | Quake et al. |
| 7,381,195 B2 | 6/2008 | Mori et al. |
| 7,393,337 B2 | 7/2008 | Tonelli et al. |
| 7,402,249 B2 | 7/2008 | Ikeda |
| 7,469,716 B2 | 12/2008 | Parrino et al. |
| 7,470,265 B2 | 12/2008 | Brugger et al. |
| 7,488,301 B2 | 2/2009 | Beden et al. |
| 7,488,447 B2 | 2/2009 | Sternby |
| 7,493,824 B2 | 2/2009 | Brucksch et al. |
| 7,494,590 B2 | 2/2009 | Felding et al. |
| 7,503,908 B2 | 3/2009 | Bartholomew |
| 7,507,380 B2 | 3/2009 | Chang et al. |
| 7,510,545 B2 | 3/2009 | Peppel |
| 7,517,332 B2 | 4/2009 | Tonelli et al. |
| 7,517,387 B2 | 4/2009 | Chevallet et al. |
| 7,520,919 B2 | 4/2009 | Caleffi |
| 7,537,687 B2 | 5/2009 | Toyoda et al. |
| 7,544,300 B2 | 6/2009 | Brugger et al. |
| 7,551,043 B2 | 6/2009 | Nguyen et al. |
| 7,559,911 B2 | 7/2009 | Giannella |
| 7,575,562 B2 | 8/2009 | Oishi et al. |
| 7,575,564 B2 | 8/2009 | Childers |
| 7,591,449 B2 | 9/2009 | Raines et al. |
| 7,603,907 B2 | 10/2009 | Reiter et al. |
| 7,615,035 B2 | 11/2009 | Peppel |
| 7,618,531 B2 | 11/2009 | Sugioka et al. |
| 7,622,043 B2 | 11/2009 | Sawada et al. |

(56) References Cited

U.S. PATENT DOCUMENTS

| | | |
|---|---|---|
| 7,632,470 B2 | 12/2009 | Tabata et al. |
| 7,647,834 B2 | 1/2010 | O'Mahony et al. |
| 7,648,474 B2 | 1/2010 | Paolini et al. |
| 7,648,476 B2 | 1/2010 | Bock et al. |
| 7,648,792 B2 | 1/2010 | Kaschmitter et al. |
| 7,656,527 B2 | 2/2010 | Scarpaci |
| 7,661,294 B2 | 2/2010 | Dam |
| 7,671,974 B2 | 3/2010 | O'Mahony et al. |
| 7,682,328 B2 | 3/2010 | Han et al. |
| 7,686,778 B2 | 3/2010 | Burbank et al. |
| 7,699,992 B2 | 4/2010 | Stemby |
| 7,708,714 B2 | 5/2010 | Connell et al. |
| 7,713,226 B2 | 5/2010 | Ash et al. |
| 7,726,361 B2 | 6/2010 | Bartholomew |
| 7,727,220 B2 | 6/2010 | Wieslander et al. |
| 7,744,553 B2 | 6/2010 | Kelly et al. |
| 7,749,184 B2 | 7/2010 | Cavalcanti et al. |
| 7,758,082 B2 | 7/2010 | Weigel et al. |
| 7,758,547 B2 | 7/2010 | Tonelli et al. |
| 7,771,379 B2 | 8/2010 | Treu |
| 7,771,380 B2 | 8/2010 | Jönsson et al. |
| 7,775,986 B2 | 8/2010 | Roeher et al. |
| 7,776,219 B2 | 8/2010 | Brugger et al. |
| 7,780,848 B2 | 8/2010 | Kim et al. |
| 7,788,038 B2 | 8/2010 | Oshita et al. |
| 7,790,029 B2 | 9/2010 | Dannenmaier et al. |
| 7,794,141 B2 | 9/2010 | Perry et al. |
| 7,794,419 B2 | 9/2010 | Paolini et al. |
| 7,801,746 B2 | 9/2010 | Moll et al. |
| 7,815,852 B2 | 10/2010 | Stemby |
| 7,824,354 B2 | 11/2010 | Vinci et al. |
| 7,871,390 B2 | 1/2011 | Rambod et al. |
| 7,873,489 B2 | 1/2011 | Dolgos et al. |
| 7,896,831 B2 | 3/2011 | Sternby et al. |
| 7,901,579 B2 | 3/2011 | Brugger et al. |
| 7,913,751 B2 | 3/2011 | Zwittig |
| 7,918,993 B2 | 4/2011 | Harraway |
| 7,922,899 B2 | 4/2011 | Vasta et al. |
| 7,955,504 B1 | 6/2011 | Jovanovic et al. |
| 7,968,250 B2 | 6/2011 | Kaschmitter et al. |
| 8,002,727 B2 | 8/2011 | Brugger et al. |
| 8,012,114 B2 | 9/2011 | Daniel et al. |
| 8,075,509 B2 | 12/2011 | Molducci et al. |
| 8,105,256 B1 | 1/2012 | Ariza |
| 8,105,265 B2 | 1/2012 | Demers et al. |
| 8,105,266 B2 | 1/2012 | Childers et al. |
| 8,128,822 B2 | 3/2012 | Browning et al. |
| 8,137,554 B2 | 3/2012 | Jovanovic et al. |
| 8,182,440 B2 | 5/2012 | Cruz et al. |
| 8,182,691 B2 | 5/2012 | Stahl |
| 8,190,651 B2 | 5/2012 | Treu et al. |
| 8,192,387 B2 | 6/2012 | Brugger et al. |
| 8,210,049 B2 | 7/2012 | Brugger |
| 8,235,931 B2 | 8/2012 | Burbank et al. |
| 8,236,599 B2 | 8/2012 | Chang et al. |
| 8,267,881 B2 | 9/2012 | O'Mahony et al. |
| 8,273,245 B2 | 9/2012 | Jovanovic et al. |
| 8,293,113 B2 | 10/2012 | Jönsson et al. |
| 8,293,114 B2 | 10/2012 | Jönsson et al. |
| 8,298,427 B2 | 10/2012 | Ficheux et al. |
| 8,323,492 B2 | 12/2012 | Childers et al. |
| 8,329,030 B2 | 12/2012 | Childers et al. |
| 8,343,085 B2 | 1/2013 | Toyoda et al. |
| 8,394,046 B2 | 3/2013 | Nuemberger et al. |
| 8,414,182 B2 | 4/2013 | Paul et al. |
| 8,419,945 B2 | 4/2013 | Browning et al. |
| 8,425,471 B2 | 4/2013 | Grant et al. |
| 8,449,487 B2 | 5/2013 | Hovland et al. |
| 8,460,228 B2 | 6/2013 | Burbank et al. |
| 8,475,398 B2 | 7/2013 | O'Mahony |
| 8,491,518 B2 | 7/2013 | Schnell et al. |
| 8,496,824 B2 | 7/2013 | Remkes et al. |
| 8,501,009 B2 | 8/2013 | Peterson et al. |
| 8,506,536 B2 | 8/2013 | Schnell |
| 8,512,553 B2 | 8/2013 | Cicchello et al. |
| 8,512,554 B2 | 8/2013 | Yu et al. |
| 8,524,086 B2 | 9/2013 | Peterson et al. |
| 8,529,491 B2 | 9/2013 | Beiriger |
| 8,535,525 B2 | 9/2013 | Heyes et al. |
| 8,603,020 B2 | 12/2013 | Roger et al. |
| 8,608,658 B2 | 12/2013 | Burbank et al. |
| 8,647,290 B2 | 2/2014 | Masala et al. |
| 8,679,348 B2 | 3/2014 | Burbank et al. |
| 8,685,244 B2 | 4/2014 | Heyes et al. |
| 8,685,251 B2 | 4/2014 | Smejtek et al. |
| 8,753,515 B2 | 6/2014 | Curtis et al. |
| 8,801,922 B2 | 8/2014 | Wrazel et al. |
| 8,840,581 B2 | 9/2014 | McGill et al. |
| 9,024,746 B2 | 5/2015 | Burbank et al. |
| 9,097,370 B2 | 8/2015 | Schnell et al. |
| 9,138,687 B2 | 9/2015 | Peterson et al. |
| 9,220,825 B2 | 12/2015 | Buckberry |
| 9,220,828 B2 | 12/2015 | Coates |
| 9,283,320 B2 | 3/2016 | Brugger et al. |
| 9,328,969 B2 | 5/2016 | Wrazel et al. |
| 9,402,945 B2 | 8/2016 | Hogard et al. |
| 9,480,455 B2 | 11/2016 | Buckberry |
| 9,482,218 B2 | 11/2016 | Coates et al. |
| 9,504,777 B2 | 11/2016 | Hogard et al. |
| 9,526,822 B2 | 12/2016 | Meyer et al. |
| 9,545,469 B2 | 1/2017 | Curtis et al. |
| 9,579,440 B2 | 2/2017 | Hogard et al. |
| 9,592,029 B2 | 3/2017 | Buckberry |
| 9,636,444 B2 | 5/2017 | Burbank et al. |
| 9,700,663 B2 | 7/2017 | Burbank et al. |
| 9,835,509 B2 | 12/2017 | Brugger et al. |
| 9,879,807 B2 | 1/2018 | Brugger et al. |
| 9,895,480 B2 | 2/2018 | Wrazel et al. |
| 10,105,476 B2 | 10/2018 | Peterson et al. |
| 10,155,076 B2 | 12/2018 | Merchant |
| 10,668,201 B2 | 6/2020 | Wrazel et al. |
| 2002/0023879 A1 | 2/2002 | Hadden |
| 2002/0032398 A1 | 3/2002 | Steele et al. |
| 2002/0088751 A1 | 7/2002 | Rosenqvist et al. |
| 2002/0108859 A1 | 8/2002 | Wang et al. |
| 2002/0108869 A1 | 8/2002 | Savtchenko |
| 2002/0115200 A1 | 8/2002 | Zou et al. |
| 2002/0162784 A1 | 11/2002 | Kohlheb et al. |
| 2002/0187069 A1 | 12/2002 | Levin et al. |
| 2003/0010717 A1 | 1/2003 | Brugger et al. |
| 2003/0039169 A1 | 2/2003 | Ehrfeld et al. |
| 2003/0052429 A1 | 3/2003 | Vigna et al. |
| 2003/0082066 A1 | 5/2003 | Hajaligol et al. |
| 2003/0138349 A1 | 7/2003 | Robinson et al. |
| 2003/0156991 A1 | 8/2003 | Halas et al. |
| 2003/0163077 A1 | 8/2003 | Kim et al. |
| 2003/0183345 A1 | 10/2003 | Soberay |
| 2003/0220598 A1 | 11/2003 | Busby et al. |
| 2004/0004589 A1 | 1/2004 | Shih |
| 2004/0008370 A1 | 1/2004 | Keane et al. |
| 2004/0012122 A1 | 1/2004 | Nagaoka et al. |
| 2004/0016700 A1 | 1/2004 | Kellam et al. |
| 2004/0020286 A1 | 2/2004 | Blakley et al. |
| 2004/0022691 A1 | 2/2004 | Allen et al. |
| 2004/0035452 A1 | 2/2004 | Ma |
| 2004/0035462 A1 | 2/2004 | McCarty et al. |
| 2004/0072278 A1 | 4/2004 | Chou et al. |
| 2004/0082903 A1 | 4/2004 | Micheli |
| 2004/0084370 A1 | 5/2004 | Singh et al. |
| 2004/0084371 A1 | 5/2004 | Kellam et al. |
| 2004/0086427 A1 | 5/2004 | Childers et al. |
| 2004/0125689 A1 | 7/2004 | Ehrfeld et al. |
| 2004/0157096 A1 | 8/2004 | Peterson |
| 2004/0158189 A1 | 8/2004 | Tonelli et al. |
| 2004/0208751 A1 | 10/2004 | Lazar et al. |
| 2004/0215129 A1 | 10/2004 | Edgson et al. |
| 2004/0256230 A1 | 12/2004 | Yager et al. |
| 2005/0006296 A1 | 1/2005 | Sullivan et al. |
| 2005/0007748 A1 | 1/2005 | Callahan et al. |
| 2005/0040110 A1 | 2/2005 | Felding |
| 2005/0061740 A1* | 3/2005 | Felding .......... B01D 61/32 210/741 |
| 2005/0070837 A1 | 3/2005 | Ferrarini et al. |
| 2005/0074834 A1 | 4/2005 | Chaplen et al. |

(56) References Cited

U.S. PATENT DOCUMENTS

| | | |
|---|---|---|
| 2005/0082225 A1 | 4/2005 | Kreymann |
| 2005/0126211 A1 | 6/2005 | Drost et al. |
| 2005/0129580 A1 | 6/2005 | Swinehart et al. |
| 2005/0131332 A1 | 6/2005 | Kelly et al. |
| 2005/0145497 A1 | 7/2005 | Gilbert et al. |
| 2005/0179748 A1 | 8/2005 | Malik et al. |
| 2005/0202557 A1 | 9/2005 | Borenstein et al. |
| 2006/0046113 A1 | 3/2006 | Wang et al. |
| 2006/0079698 A1 | 4/2006 | Joshi et al. |
| 2006/0157413 A1 | 7/2006 | Bene et al. |
| 2006/0174715 A1 | 8/2006 | Wehrs et al. |
| 2006/0200064 A1 | 9/2006 | Gross et al. |
| 2006/0266692 A1 | 11/2006 | Foster et al. |
| 2007/0020400 A1 | 1/2007 | Chang |
| 2007/0029365 A1 | 2/2007 | Paul et al. |
| 2007/0119771 A1 | 5/2007 | Schukar et al. |
| 2007/0125489 A1 | 6/2007 | Paul et al. |
| 2007/0128707 A1 | 6/2007 | Rorrer et al. |
| 2007/0131403 A1 | 6/2007 | Vetrovec et al. |
| 2007/0149914 A1 | 6/2007 | Axelsson et al. |
| 2007/0158249 A1 | 7/2007 | Ash |
| 2007/0158268 A1 | 7/2007 | Decomo |
| 2007/0184576 A1 | 8/2007 | Chang et al. |
| 2007/0215644 A1 | 9/2007 | Otis et al. |
| 2007/0243990 A1 | 10/2007 | Kolenbrander et al. |
| 2007/0278155 A1 | 12/2007 | Lo et al. |
| 2007/0295651 A1 | 12/2007 | Martinez et al. |
| 2008/0006040 A1 | 1/2008 | Peterson et al. |
| 2008/0009780 A1 | 1/2008 | Leonard et al. |
| 2008/0053842 A1 | 3/2008 | Williams et al. |
| 2008/0097274 A1 | 4/2008 | Neri et al. |
| 2008/0108122 A1 | 5/2008 | Paul et al. |
| 2008/0108930 A1 | 5/2008 | Weitzel et al. |
| 2008/0149563 A1 | 6/2008 | Ash |
| 2008/0196725 A1 | 8/2008 | Mele |
| 2008/0200858 A1 | 8/2008 | Ichilshi et al. |
| 2008/0296226 A1 | 12/2008 | Gotch |
| 2009/0008331 A1 | 1/2009 | Wilt et al. |
| 2009/0012452 A1 | 1/2009 | Slepicka et al. |
| 2009/0038393 A1 | 2/2009 | Chaung et al. |
| 2009/0076433 A1 | 3/2009 | Folden et al. |
| 2009/0087326 A1 | 4/2009 | Voltenburg et al. |
| 2009/0092526 A1 | 4/2009 | Miller |
| 2009/0095679 A1 | 4/2009 | Demers et al. |
| 2009/0101549 A1 | 4/2009 | Kamen et al. |
| 2009/0101576 A1 | 4/2009 | Rohde et al. |
| 2009/0114595 A1 | 5/2009 | Wallenas et al. |
| 2009/0124963 A1 | 5/2009 | Hogard et al. |
| 2009/0165366 A1 | 7/2009 | Jovanovic et al. |
| 2009/0211977 A1 | 8/2009 | Miller |
| 2009/0230036 A1 | 9/2009 | Apel et al. |
| 2009/0306573 A1 | 12/2009 | Gagner et al. |
| 2009/0309835 A1 | 12/2009 | Levin et al. |
| 2009/0312686 A1 | 12/2009 | Sakamoto et al. |
| 2009/0320684 A1 | 12/2009 | Weaver et al. |
| 2010/0018923 A1 | 1/2010 | Rohde et al. |
| 2010/0022934 A1 | 1/2010 | Hogard |
| 2010/0051552 A1 | 3/2010 | Rohde et al. |
| 2010/0078385 A1 | 4/2010 | Kawarabata et al. |
| 2010/0089807 A1 | 4/2010 | Heyes et al. |
| 2010/0192686 A1 | 8/2010 | Kamen et al. |
| 2010/0271296 A1 | 10/2010 | Kopychev et al. |
| 2010/0292627 A1 | 11/2010 | Caleffi et al. |
| 2010/0292657 A1 | 11/2010 | Fontanazzi et al. |
| 2010/0292944 A1 | 11/2010 | Howell et al. |
| 2010/0321046 A1 | 12/2010 | Randall et al. |
| 2010/0326914 A1 | 12/2010 | Drost et al. |
| 2011/0005986 A1 | 1/2011 | Kelly et al. |
| 2011/0009796 A1 | 1/2011 | Tulis et al. |
| 2011/0105979 A1 | 5/2011 | Schlaeper et al. |
| 2011/0106466 A1 | 5/2011 | Furmanski et al. |
| 2011/0132841 A1 | 6/2011 | Rohde et al. |
| 2011/0186517 A1 | 8/2011 | Hedmann et al. |
| 2011/0189048 A1 | 8/2011 | Curtis et al. |
| 2011/0257579 A1 | 10/2011 | Rossi et al. |
| 2011/0295175 A1 | 12/2011 | Felder et al. |
| 2012/0029937 A1 | 2/2012 | Neftel et al. |
| 2012/0065581 A1 | 3/2012 | Childers et al. |
| 2012/0103902 A1 | 5/2012 | Childers et al. |
| 2012/0116316 A1 | 5/2012 | Schutz et al. |
| 2012/0138533 A1 | 6/2012 | Curtis et al. |
| 2012/0204968 A1 | 8/2012 | Fulkerson et al. |
| 2012/0226236 A1 | 9/2012 | Fini et al. |
| 2012/0248017 A1 | 10/2012 | Beiriger et al. |
| 2012/0267291 A1 | 10/2012 | Coates |
| 2012/0292246 A1 | 11/2012 | Jovanovic et al. |
| 2012/0298580 A1 | 11/2012 | Gronau et al. |
| 2012/0318740 A1 | 12/2012 | Ekdahl et al. |
| 2013/0018301 A1 | 1/2013 | Weaver et al. |
| 2013/0020237 A1 | 1/2013 | Wilt et al. |
| 2013/0030344 A1 | 1/2013 | Gronau et al. |
| 2013/0037485 A1 | 2/2013 | Will et al. |
| 2013/0056418 A1 | 3/2013 | Kopperschmidt et al. |
| 2013/0056419 A1 | 3/2013 | Curtis |
| 2013/0060233 A1 | 3/2013 | O'Connor et al. |
| 2013/0146541 A1 | 6/2013 | Weigel et al. |
| 2013/0180339 A1 | 7/2013 | Brugger |
| 2013/0186829 A1 | 7/2013 | Callan et al. |
| 2013/0206693 A2 | 8/2013 | Thys |
| 2013/0213890 A1 | 8/2013 | Kelly et al. |
| 2013/0267883 A1 | 10/2013 | Medrano |
| 2013/0303962 A1 | 11/2013 | Bernard |
| 2013/0303963 A1 | 11/2013 | Breuch et al. |
| 2014/0014580 A1 | 1/2014 | Ritter |
| 2014/0018727 A1 | 1/2014 | Burbank et al. |
| 2014/0021111 A1 | 1/2014 | Roger et al. |
| 2014/0069861 A1 | 3/2014 | Browning et al. |
| 2014/0072288 A1 | 3/2014 | Newell |
| 2014/0076058 A1 | 3/2014 | Brugger et al. |
| 2014/0158589 A1 | 6/2014 | Furuhashi et al. |
| 2014/0178215 A1 | 6/2014 | Baxter et al. |
| 2014/0209540 A1 | 7/2014 | Smejtek et al. |
| 2014/0216250 A1 | 8/2014 | Meyer et al. |
| 2014/0276424 A1 | 9/2014 | Davis et al. |
| 2014/0291243 A1 | 10/2014 | Curtis et al. |
| 2014/0319035 A1 | 10/2014 | Burbank et al. |
| 2015/0005699 A1 | 1/2015 | Burbank et al. |
| 2015/0027951 A1 | 1/2015 | Wallace et al. |
| 2015/0029817 A1* | 1/2015 | Orszullok ............ B01F 35/513 366/342 |
| 2015/0041377 A1 | 2/2015 | Heyes |
| 2015/0076053 A1 | 3/2015 | Higgitt et al. |
| 2015/0129481 A1 | 5/2015 | Higgitt et al. |
| 2015/0196702 A1 | 7/2015 | Burbank et al. |
| 2015/0204733 A1 | 7/2015 | Newell et al. |
| 2015/0238676 A1 | 8/2015 | Giordano et al. |
| 2015/0252800 A1 | 9/2015 | Buckberry et al. |
| 2015/0267821 A1 | 9/2015 | Brugger et al. |
| 2015/0306294 A1 | 10/2015 | Jansson et al. |
| 2015/0314055 A1 | 11/2015 | Hogard et al. |
| 2015/0343128 A1 | 12/2015 | Hogard et al. |
| 2015/0343133 A1 | 12/2015 | Hogard et al. |
| 2015/0354906 A1 | 12/2015 | Miller |
| 2015/0359973 A1 | 12/2015 | Onken et al. |
| 2016/0045656 A1* | 2/2016 | Buckberry .......... A61M 1/1668 210/257.2 |
| 2016/0051739 A1 | 2/2016 | Buckberry |
| 2016/0051743 A1 | 2/2016 | Buckberry |
| 2016/0082172 A1 | 3/2016 | Miller et al. |
| 2016/0084785 A1 | 3/2016 | Buckberry |
| 2016/0106906 A1 | 4/2016 | Buckberry |
| 2016/0199558 A1 | 7/2016 | Buckberry |
| 2016/0325034 A1 | 11/2016 | Wiktor et al. |
| 2017/0239411 A1 | 8/2017 | Lura et al. |
| 2017/0290970 A1 | 10/2017 | Friederichs et al. |
| 2017/0296727 A1 | 10/2017 | Burbank et al. |
| 2017/0296730 A1 | 10/2017 | Soto et al. |
| 2017/0312419 A1 | 11/2017 | Burbank et al. |
| 2017/0326285 A1 | 11/2017 | Hogard et al. |
| 2018/0071447 A1 | 3/2018 | Gronau et al. |
| 2018/0128688 A1 | 5/2018 | Newell et al. |
| 2018/0128698 A1 | 5/2018 | Brugger et al. |
| 2018/0133384 A1 | 5/2018 | Tokunaga et al. |
| 2019/0022293 A1 | 1/2019 | Peterson et al. |

(56) References Cited

U.S. PATENT DOCUMENTS

| | | |
|---|---|---|
| 2019/0125950 A1 | 5/2019 | Noack |
| 2019/0192758 A1 | 6/2019 | Ritson et al. |
| 2019/0201604 A1 | 7/2019 | Hogard et al. |
| 2019/0381232 A1 | 12/2019 | Crnkovich et al. |
| 2020/0033897 A1 | 1/2020 | Jensen et al. |
| 2020/0061273 A1 | 2/2020 | Hogard et al. |
| 2020/0282125 A1 | 9/2020 | Kalaskar et al. |
| 2020/0316283 A1 | 10/2020 | Vecten et al. |
| 2021/0069401 A1 | 3/2021 | Peterson et al. |
| 2021/0244869 A1 | 8/2021 | Hogard et al. |
| 2021/0252204 A1 | 8/2021 | Hogard et al. |
| 2023/0347035 A1 | 11/2023 | Ritson et al. |

FOREIGN PATENT DOCUMENTS

| | | |
|---|---|---|
| CA | 2887068 A1 | 4/2014 |
| CA | 2930431 A1 | 5/2015 |
| CN | 200951223 Y | 9/2007 |
| DE | 8702995 U1 | 6/1987 |
| DE | 69217519 T2 | 6/1997 |
| EP | 0165751 A2 | 12/1985 |
| EP | 0278100 A2 | 8/1988 |
| EP | 0324922 A2 | 7/1989 |
| EP | 0679100 A1 | 11/1995 |
| EP | 0796997 A1 | 9/1997 |
| EP | 0547025 B2 | 6/2002 |
| EP | 1892000 A1 | 2/2008 |
| EP | 1898000 A2 | 3/2008 |
| EP | 2319551 A2 | 5/2011 |
| EP | 2535067 A1 | 12/2012 |
| GB | 1289738 A | 9/1972 |
| JP | 59-58002 A | 4/1984 |
| JP | 60-143803 A | 7/1985 |
| JP | H4-35669 A | 2/1992 |
| JP | H10-15059 A | 1/1998 |
| JP | H11-33111 A | 2/1999 |
| JP | 2001510266 A | 7/2001 |
| JP | 2002143298 A | 5/2002 |
| JP | 2002527212 A | 8/2002 |
| JP | 2003508179 A | 3/2003 |
| JP | 2005512736 A | 5/2005 |
| JP | 2006255331 A | 9/2006 |
| JP | 2006280775 A | 10/2006 |
| JP | 2007167108 A | 7/2007 |
| JP | 2007268490 A | 10/2007 |
| JP | 2007529707 A | 10/2007 |
| JP | 2007327950 A | 12/2007 |
| JP | 2012152286 A | 8/2012 |
| JP | 2012152288 A | 8/2012 |
| JP | 55-14045 A | 6/2014 |
| JP | 2014531922 A | 12/2014 |
| JP | 2018524074 A | 8/2018 |
| WO | WO00/16916 A1 | 3/2000 |
| WO | WO00/25843 A1 | 5/2000 |
| WO | WO00/57935 A1 | 10/2000 |
| WO | WO02/40874 A1 | 5/2002 |
| WO | WO02/076529 A1 | 10/2002 |
| WO | WO03/076661 A1 | 9/2003 |
| WO | WO2006/011009 A2 | 2/2006 |
| WO | WO2006/039293 A2 | 4/2006 |
| WO | WO2007/073739 A1 | 7/2007 |
| WO | WO2007/089855 A2 | 8/2007 |
| WO | WO2008/027967 A1 | 3/2008 |
| WO | WO2008/106191 A2 | 9/2008 |
| WO | WO2010/027435 A1 | 3/2010 |
| WO | WO2010/062698 A2 | 6/2010 |
| WO | WO2010/085764 A2 | 7/2010 |
| WO | WO2010/146343 A2 | 12/2010 |
| WO | WO2013/031966 A1 | 3/2013 |
| WO | WO2014/117000 A2 | 7/2014 |
| WO | WO2014/124180 A2 | 8/2014 |
| WO | WO2014/159420 A1 | 10/2014 |
| WO | WO2014/160370 A1 | 10/2014 |
| WO | WO2015/150179 A1 | 10/2015 |
| WO | WO2015/173151 A1 | 11/2015 |
| WO | WO2015/185920 A1 | 12/2015 |
| WO | WO2016/030147 A1 | 3/2016 |
| WO | WO2016/049542 A2 | 3/2016 |
| WO | WO2016/057981 A1 | 4/2016 |
| WO | WO2016/057982 A1 | 4/2016 |
| WO | WO2016/130679 A2 | 9/2016 |
| WO | WO2016/208705 A1 | 12/2016 |
| WO | WO2017/072511 A1 | 5/2017 |
| WO | WO2018/035520 A1 | 2/2018 |
| WO | WO2020/223500 A1 | 11/2020 |

OTHER PUBLICATIONS

Anglés et al., "Plasticized starch/Tunicin Whiskers Nanocomposite Materials. 2. Mechanical behavior," Macromolecules, 34, pp. 2921-2931, Mar. 2001.

California Energy Commission; Development of Supported Polymeric Liquid Membrane Technology for Aqueous MTBE Mitigation, EPRI, Palo Alto, CA, California Energy Commission, Sacramento, CA: Doc. No. 1006577; 70 pgs.; Jul. 2002.

Demura et al., "Ductile Thin Foil of Ni3Al," Mechanical Properties of Structural Films, ASTM International Nov. 2000 Symposium (Orlando, FL), pp. 248-261, published Oct. 1, 2001.

Favier et al.; Nanocomposite materials from latex and cellulose whiskers; Polymers for Advanced Technologies; 6; pp. 351-355; Jan. 1995.

Federal Energy Technology Center, "Technology Development Through Industrial Partnerships," (Tech. Dev. Data Sheet), 12 pgs., Sep. 1998.

Grunert et al., "Progress in the Development of Cellulose Reinforced Nanocomposites," PMSE Preprints 2000, 82, 232, 2 pgs., Mar. 2000.

Haas, "Further development of MMW and SMMW platelet feed horn arrays," Astron, Soc. Pac. Conf. Ser., vol. 75, pp. 99-105, Multi-Feed Systems for Radio Telescopes, Workshop held in Tucson, Arizona, May 16-18, 1994.

Introtek International; Drip chamber liquid level sensor (sales literature); 2 pages; retrieved from the internet (http://www.introtek.com/PDFs/1/DDS-14.0_DripDetectSensor.pdf); ©Jan. 1, 2009.

Koeneman et al., "Feasibility of Micro Power Supplies for MEMS," (pre-publication copy) J. MicroElectoMechanical Sys., 6(4), pp. 355-362, Dec. 1997.

Morin et al., "Nanocomposites of Chitin Whiskers from Riftia Tubes and Poly (caprolactone)," Macromolecules, vol. 35, pp. 2190-2199, Feb. 2002.

Nakamura et al., "Research on Pressure Weiding Conditions of Various Work Metals (Effects of Contact Pressure, Surface Expansion Ratio and Temperature)," JSME International Journal, Series III 31(3), 612-617, Sep. 1988.

Nakao et al., "Diffusion Bonding of Intermetallic Compound TiAl," ISIJ International, 31(10), 1260-1266, Oct. 1991.

Oddy et al., "Electrokinetic Instability Micromixing," Anal. Chem., 73(24), pp. 5822-5832, Dec. 2001.

Omega Engineering Inc.; Load Cell (definition, information); 3 pgs; retrieved from the internet on Jun. 17, 2015 (http://www.omega.com/prodinfo/LoadCells.html).

Orts et al., "Effect of Fiber Source on Cellulose Reinforced Polymer Nanocomposites," ANTEC 2004: Conference Proceedings, 62nd Annual Tech. Conference; Chicago, IL, pp. 2427-2431, May 2004.

Paillet et al., "Chitin Whisker Reinforced Thermoplastic Nanocomposites," Macromolecules, vol. 34, No. 19, pp. 6527-6530, Sep. 2001.

Paul et al., "Microlamination for Microtechnology-based Energy, Chemical, and Biological Systems," ASME IMECE, ASE vol. 39, pp. 45-52, Nashville, Tennessee, Nov. 15-20, 1999.

Pluess, "Application of Controlled Thermal Expansion in Diffusion Bonding for the High-Volume Microlamination of MECS Devices," Thesis (MS), Oregon State University, 193 pgs., Sep. 2004.

Porter et al.; Cost drivers in microlamination based on a high volume production system design; ASME 2002 Conf. Proc.; New Orleans, Louisiana; pp. 267-274; Nov. 17-22, 2002.

Sharma et al., "The Application of Surface Mount Technology to Multi-Scale Process Intensification," ASPE, pp. 1-4, Oct. 2003.

(56) References Cited

OTHER PUBLICATIONS

Stroock et al., "Chaotic Mixer for Microchannels," Science, 295, pp. 647-651, Jan. 2002.
Thorsen et al.; Microfluidic Large-Scale Integration; Science; 298; pp. 580-584; Oct. 18, 2002.
Wegeng et al., "Chemical system miniaturization," Proceedings of the AIChE Spring National Meeting, pp. 1-13, Feb. 1996.
Hogard et al.; U.S. Pat. Appl. # U.S. Appl. No. 17/395,281 entitled "Dialysis system and methods," filed Aug. 5, 2021.
Hu et al.; U.S. Appl. No. 17/522,778 entitled "Dialysis system and methods," filed Nov. 9, 2021.
Peterson et al.; U.S. Appl. No. 18/344,376 entitled "Fluid Purification System," filed Jun. 29, 2023.
Ritson et al., U.S. Appl. No. 18/593,221 entitled "Peritoneal dialysis system and methods," filed Mar. 1, 2024.
Hu et al.; U.S. Appl. No. 18/728,723 entitled "Dialysis system and methods," filed Jul. 12, 2024.

\* cited by examiner

Patient's Vascular Access (Fistula/Graft)

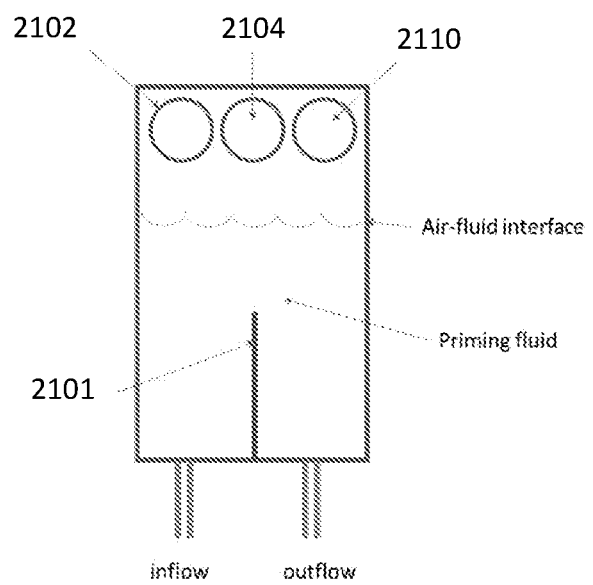
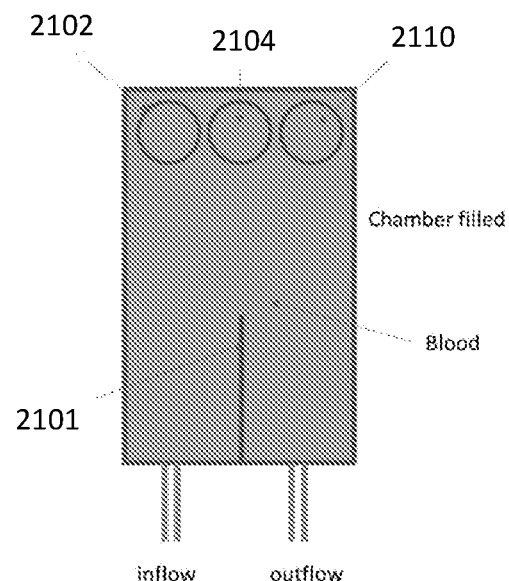
FIG. 21A
FIG. 21B

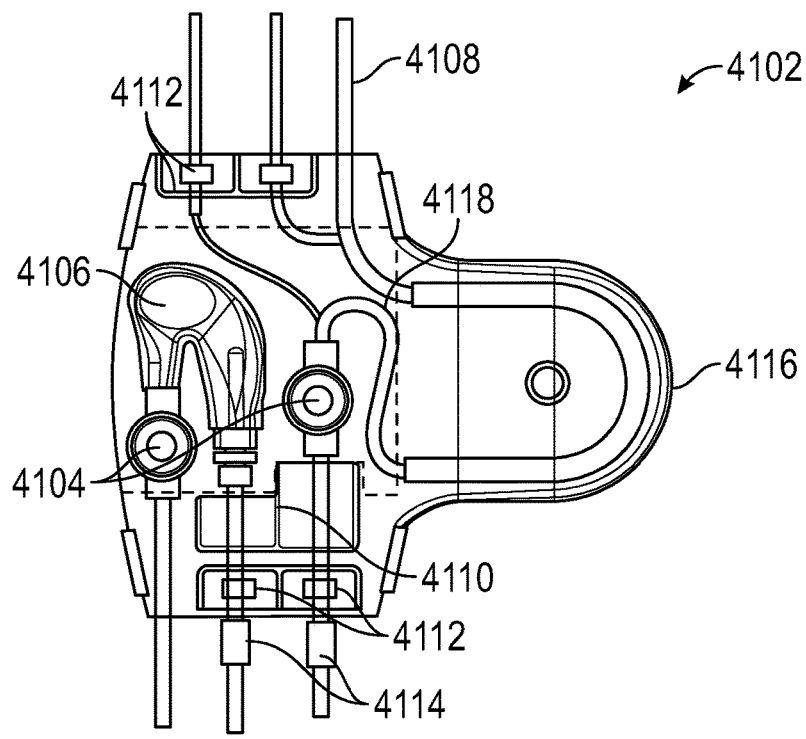
FIG. 41
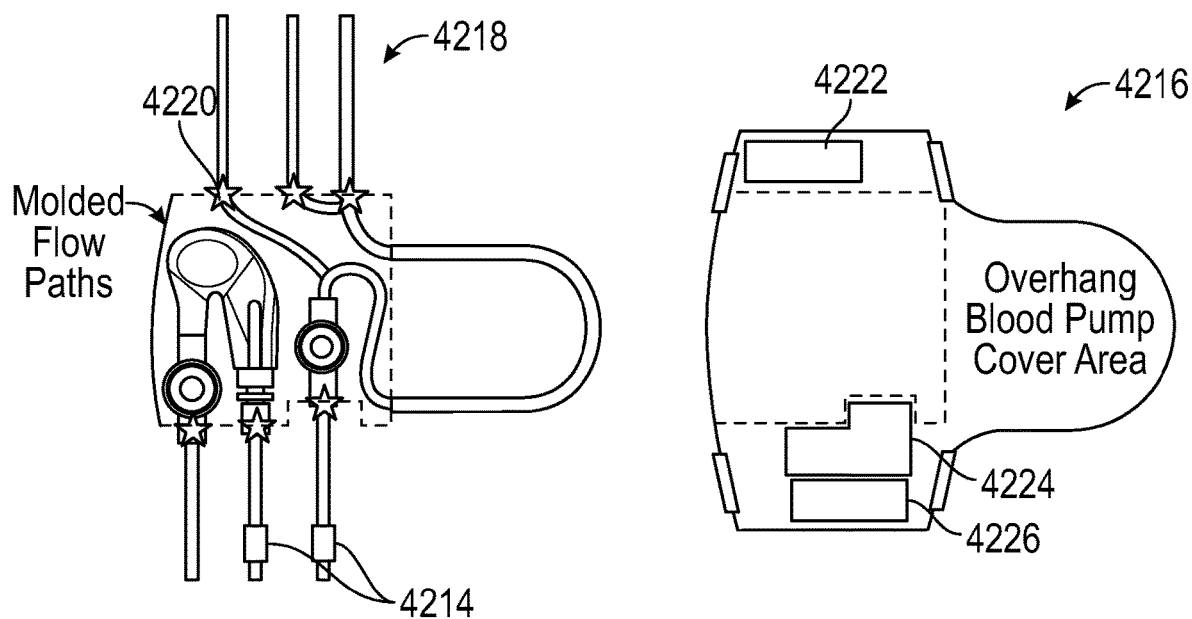
FIG. 42A  FIG. 42B

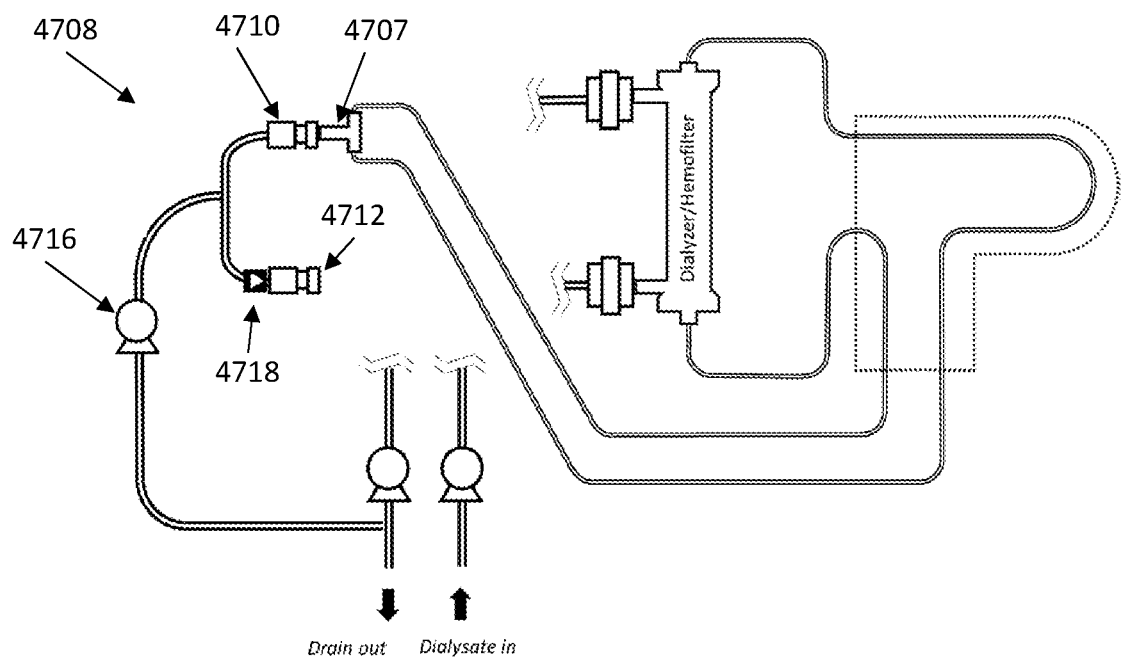

DIALYSIS SYSTEMS AND METHODS

CROSS REFERENCE TO RELATED APPLICATIONS

This application claims the benefit of U.S. Provisional Application No. 62/841,051, filed Apr. 30, 2019, titled "Automated Multimodal Sensor and Extracorporeal Cartridge for Hemodialysis", and of U.S. Provisional Application No. 62/933,752, filed Nov. 11, 2019, titled "Dialysis System and Methods", which are incorporated herein by reference in their entirety.

This application is related to U.S. Pat. No. 9,504,777, titled "Dialysis System and Methods", and to U.S. patent application Ser. No. 16/550,042, filed Aug. 23, 2019, both of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to dialysis systems. More specifically, this disclosure relates to systems and methods for creating dialysate in real-time during dialysis treatment.

BACKGROUND

There are, at present, hundreds of thousands of patients in the United States with end-stage renal disease. Most of those require dialysis to survive. Many patients receive dialysis treatment at a dialysis center, which can place a demanding, restrictive and tiring schedule on a patient. Patients who receive in-center dialysis typically must travel to the center at least three times a week and sit in a chair for 3 to 4 hours each time while toxins and excess fluids are filtered from their blood. After the treatment, the patient must wait for the needle site to stop bleeding and blood pressure to return to normal, which requires even more time taken away from other, more fulfilling activities in their daily lives. Moreover, in-center patients must follow an uncompromising schedule as a typical center treats three to five shifts of patients in the course of a day. As a result, many people who dialyze three times a week complain of feeling exhausted for at least a few hours after a session.

Many dialysis systems on the market require significant input and attention from technicians prior to, during, and after the dialysis therapy. Before therapy, the technicians are often required to manually install patient blood tubing sets onto the dialysis system, connect the tubing sets to the patient, and to the dialyzer, and manually prime the tubing sets to remove air from the tubing set before therapy. During therapy, the technicians are typically required to monitor venous pressure and fluid levels, and administer boluses of saline and/or heparin to the patient. After therapy, the technicians are often required to return blood in the tubing set to the patient and drain the dialysis system. The inefficiencies of most dialysis systems and the need for significant technician involvement in the process make it even more difficult for patients to receive dialysis therapy away from large treatment centers.

Given the demanding nature of in-center dialysis, many patients have turned to home dialysis as an option. Home dialysis provides the patient with scheduling flexibility as it permits the patient to choose treatment times to fit other activities, such as going to work or caring for a family member. Unfortunately, current dialysis systems are generally unsuitable for use in a patient's home. One reason for this is that current systems are too large and bulky to fit within a typical home. Current dialysis systems are also energy-inefficient in that they use large amounts of energy to heat large amounts of water for proper use. Although some home dialysis systems are available, they generally are difficult to set up and use. As a result, most dialysis treatments for chronic patients are performed at dialysis centers.

Hemodialysis is also performed in the acute hospital setting, either for current dialysis patients who have been hospitalized, or for patients suffering from acute kidney injury. In these care settings, typically a hospital room, water of sufficient purity to create dialysate is not readily available. Therefore, hemodialysis machines in the acute setting rely on large quantities of pre-mixed dialysate, which are typically provided in large bags and are cumbersome for staff to handle. Alternatively, hemodialysis machines may be connected to a portable RO (reverse osmosis) machine, or other similar water purification device. This introduces another independent piece of equipment that must be managed, transported and disinfected.

SUMMARY

A method of calculating arterial pressure during dialysis treatment is provided, comprising the steps of operating a blood pump of a dialysis system at a pre-selected speed, measuring a flow rate of blood in a tubing set of the dialysis system, comparing the measured flow rate with the pre-selected speed, calculating the arterial pressure based on the difference between the measured flow rate and the pre-selected speed, and adjusting the blood pump speed such that the measured flow rate matches the pre-selected speed.

A flow chamber of a dialysis system is also provided, comprising a housing comprising an inflow lumen and an outflow lumen, a septum within the housing at least partially separating the inflow lumen from the outflow lumen, a flexible elastomeric diaphragm configured to sense a pressure within the housing, the flexible elastomeric diaphragm being impermeable to fluid and gas, an air evacuation mechanism configured to evacuate air but not fluid from the housing.

In some embodiments, the air evacuation mechanism comprises a hydrophobic membrane that is impermeable to fluid but permeable to gas. In other embodiments, the air evacuation mechanism comprises a float ball valve.

A method of creating dialysate in a dialysis system is also provided, comprising the steps of creating a flow of water into a dialysis therapy system, measuring a pH of the flow of water, delivering an acid and/or bicarbonate concentrate from a dialysate proportioning system of the dialysis system into the flow of water to adjust the pH of the water, purifying the water with a water purification system of the dialysis system, and delivering the acid and/or bicarbonate concentrate from the dialysate proportioning system into the purified water having the adjusted pH to form a dialysate.

In some examples, the method further comprises performing dialysis therapy on a user of the dialysis system with the dialysate.

A dialysis system configured to create dialysate is provided, comprising a source of water configured to provide a flow of water into the dialysis system, a pH sensor disposed in the dialysis system and configured to measure a pH of the flow of water, a controller disposed in the dialysis system and configured to deliver an acid and/or bicarbonate concentrate from a dialysate proportioning system of the dialysis system into the flow of water based on the measured pH to adjust the pH of the flow of water, a water purification system disposed in the dialysis system and being configured to purify the flow of water, and the controller being further configured to deliver the acid and/or bicarbonate concentrate from the dialysate proportioning system into the purified water having the adjusted pH to form a dialysate.

A method of measuring a percent rejection in a dialysis system is provided, comprising the steps of measuring a first conductivity of water prior to a reverse osmosis filtration system, flowing the water through the reverse osmosis filtration system, flowing the water through a degassing chamber configured to remove dissolved gasses from the water, measuring a second conductivity of water after the degassing chamber, and establishing a fractional relationship between the first conductivity and the second conductivity to determine the percent rejection.

An air removal chamber configured to remove gas from a dialysis system is provided, comprising a blood chamber configured to receive a flow of blood from an extracorporeal circuit of the dialysis system, a primary membrane disposed in the blood chamber, the primary membrane being configured to allow gas and small amounts of blood plasma to pass but configured to not allow blood to pass, a secondary chamber positioned adjacent to the primary membrane and being configured to collect the small amounts of blood plasma, a secondary membrane disposed in the secondary chamber and being configured to allow gas to pass but not blood to pass.

In some examples, the primary and secondary membranes are positioned generally perpendicular to a general plane of flow of blood through the blood chamber. In other embodiments, the primary and secondary membranes are positioned generally parallel to a general plane of flow of blood through the blood chamber.

One example of the air removal chamber further comprises a tap in the secondary chamber configured to allow access to collected blood plasma within the secondary chamber.

Another example further comprises a perforated support structure disposed within the secondary chamber, the perforated support structure being configured to provide structural support between the primary membrane and the secondary membrane.

A method of collecting and analyzing blood plasma during dialysis therapy is provided, comprising initiating dialysis therapy, allowing blood plasma and gas but not blood to pass through a primary membrane of an air removal chamber and into a secondary chamber of the air removal chamber, collecting a sample of the blood plasma from the secondary chamber of the air removal chamber, analyzing the sample of blood plasma in a blood plasma analyzer, and completing the dialysis therapy.

In some embodiments, the collecting step further comprises collecting the sample of blood plasma from the secondary chamber via a tap in the secondary chamber. In other embodiments, the collecting step further comprises automatically transporting the sample of blood plasma from the secondary chamber to the blood plasma analyzer.

A method of removing gas from an extracorporeal circuit of a dialysis system is also provided, comprising the steps of operating a blood pump of the dialysis system to move fluid through the extracorporeal circuit, including through an air removal chamber of the extracorporeal circuit, allowing gas to be removed from the air removal chamber across a ventable membrane into a gas removing chamber, operating a level adjust pump that is coupled to the gas removing chamber to create a vacuum in the gas removing chamber and to expedite the removal of gas removed from the air removal chamber.

In one example, the method further comprises monitoring a pressure within the gas removing chamber, if the monitored pressure is relatively constant, stopping the operation of the level adjust pump, continuing to monitor a pressure within the gas removing chamber, and determining that a leak is present in the extracorporeal circuit if the monitored pressure in the gas removing chamber does not increase with the level adjust pump stopped.

In another example, the method further comprises monitoring a pressure within the gas removing chamber, and if the monitored pressure has fallen, determining that all gas has been removed from the extracorporeal circuit and that the extracorporeal circuit is fully primed.

An air removal chamber configured to remove gas from a dialysis system is provided, comprising a blood chamber configured to receive a flow of blood from an extracorporeal circuit of the dialysis system, a gas removing chamber adjacent to the blood chamber, a ventable membrane disposed between the blood chamber and the gas removing chamber, the ventable membrane being configured to allow gas but not blood to pass from the blood chamber to the gas removing chamber, a level adjusting pump fluidly coupled to the gas removing chamber, the level adjusting pump being configured to increase a pressure gradient across the ventable filter, and an electronic controller being configured to monitor a pressure within the gas removing chamber, the electronic controller being further configured to determine that all gas has been removed from the extracorporeal circuit and that the extracorporeal circuit is fully primed if the monitored pressure has fallen.

In some embodiments, the ventable filter is deformable.

An air removal chamber configured to remove gas from a dialysis system, comprising, a blood chamber configured to receive a flow of blood from an extracorporeal circuit of the dialysis system, a gas removing chamber adjacent to the blood chamber, a deformable, ventable membrane disposed between the blood chamber and the gas removing chamber, the deformable, ventable membrane being configured to allow gas but not blood to pass from the blood chamber to the gas removing chamber, a level adjusting pump fluidly coupled to the gas removing chamber, the level adjusting pump being configured to operate to increase a pressure gradient across the deformable, ventable filter, and an electronic controller being configured to monitor a pressure within the gas removing chamber, the electronic controller being further configured to stop the operation of the level adjust pump and continue to monitor the pressure within the gas removing chamber with the level adjust pump stopped, the electronic controller being further configured to determine that a leak is present in the extracorporeal circuit if the monitored pressure in the gas removing chamber does not increase with the level adjust pump stopped.

A method of inferring a line pressure in an extracorporeal circuit of a dialysis system between a blood pump and a dialyzer is also provided, comprising the steps of operating the blood pump of the dialysis system to create a flow of blood in the extracorporeal circuit, measuring a first arterial line pressure within an arterial line of the extracorporeal circuit, opening a fluid pathway between the arterial line and a saline source, measuring a second arterial line pressure within the arterial line of the extracorporeal circuit, determining a hydrostatic pressure of the saline source by subtracting the first arterial line pressure from the second arterial line pressure, opening a fluid pathway between a venous line of the extracorporeal circuit and the saline source, measuring a third arterial line pressure within the arterial line of the extracorporeal circuit, determining the line pressure between the blood pump and the dialyzer by subtracting the hydrostatic pressure of the saline source from the third arterial line pressure.

In some examples, the method further comprises closing the fluid pathways between the saline source and both the arterial and venous lines, measuring a venous line pressure within the venous line of the extracorporeal circuit, determining a pressure drop across the dialyzer by subtracting the line pressure between the blood pump and the dialyzer from the venous line pressure.

In one embodiment, the method further comprises determining that the dialyzer is compromised if the pressure drop across the dialyzer exceeds a clearance threshold.

A dialysate delivery subsystem of a dialysis system is also provided, comprising a water supply port in fluid communication with a source of purified water, a concentrate connection cap having an outlet line in fluid communication with the dialysis machine, the concentrate connection cap being configured to mate with one of the water supply port, a powdered bicarbonate canister, or a pre-mixed liquid bicarbonate concentrate container, wherein in a first configuration, a powdered bicarbonate canister is connected to the water supply port, and the concentrate connection cap is connected to the powdered bicarbonate canister, and wherein purified water is delivered from the water supply port into the powdered bicarbonate canister to form a mixed bicarbonate solution which is then delivered to the dialysis system via the outlet line of the concentration connection cap, wherein in a second configuration, the concentrate connection cap is connected to the pre-mixed liquid bicarbonate concentrate container, and wherein a mixed bicarbonate solution is then delivered to the dialysis system via the outlet line of the concentration connection cap, and wherein in a third configuration, the concentrate connection cap is connected directly to the water supply port, and wherein purified water from the source of purified water is configured to flow through the concentration connection cap to flush out residual concentrates.

In one embodiment, in the second configuration, the water supply port is automatically closed. In another embodiment, in the second configuration, a straw or conduit fluidly couples the concentrate connection cap to the pre-mixed liquid bicarbonate concentrate container.

A dialysate delivery subsystem of a dialysis system is provided, comprising a water supply port in fluid communication with a source of purified water, a powdered bicarbonate canister having an inlet configured to mate with the water supply port, the powdered bicarbonate canister further comprising an outlet positioned lower than the inlet and a filter positioned above the outlet, a concentrate connection cap having an outlet line in fluid communication with the dialysis system, the concentrate connection cap being configured to mate with the outlet of the powdered bicarbonate canister, wherein purified water from the water supply port is configured to mix with powdered bicarbonate concentrate in the powdered bicarbonate canister to produce a liquid bicarbonate that can then be proportioned by the concentrate connection cap to the dialysis system.

In one example, the filter is conical.

A method of providing extracorporeal dialysis therapy and intracorporeal dialysis therapy with the same dialysis system is provided, comprising the steps of attaching an extracorporeal therapy tubing set to the dialysis machine, the extracorporeal therapy tubing set comprising at least an arterial line, a venous line, an air removal chamber, and a dialyzer, providing extracorporeal dialysis therapy with the extracorporeal therapy tubing set, removing the extracorporeal therapy tubing set from the dialysis machine, attaching an intracorporeal therapy tubing set to the dialysis machine, the intracorporeal therapy tubing set comprising at least an inlet line, an outlet line, and an air removal chamber, providing intracorporeal dialysis therapy with the intracorporeal therapy tubing set.

In some examples, a blood pump of the dialysis system is connected to the extracorporeal therapy tubing set but not the intracorporeal therapy tubing set.

In one embodiment, the method further comprises removing gas from both the extracorporeal therapy tubing set and the intracorporeal therapy tubing set with the air removal chamber.

A dialysis system configured to provide both extracorporeal dialysis therapy and intracorporeal dialysis therapy is provided, comprising an interface panel configured to receive either an intracorporeal therapy tubing set or an extracorporeal therapy tubing set, the interface panel comprising one or more sensors configured to measure a pressure and/or flow of fluid within the intracorporeal therapy tubing set or the extracorporeal therapy tubing set, a mounting feature configured to receive a dialyzer or a dialyzer shell, a source of dialysate, and a blood pump, wherein in a first configuration in which an intracorporeal therapy tubing set is installed on the interface panel and a dialyzer shell is installed in the mounting feature, the dialysis system is configured to deliver dialysate from the source of dialysate, through the dialyzer shell, into the intracorporeal therapy tubing set, and wherein in a second configuration in which an extracorporeal therapy tubing set is installed on the interface panel and a dialyzer is installed in the mounting feature, the dialysis system is configured to deliver dialysate from the source of dialysate through the dialyzer while the blood pump draws blood from the patient into the extracorporeal therapy tubing set and into the dialyzer.

In some embodiments, the dialyzer shell further comprises a single-use microbe/endotoxin filter.

A single-use microbe/endotoxin filter configured to be used with a dialysis system is also provided, comprising a first port configured to removably mate with an inlet of a dialyzer, a second port configured to removably mate with an outlet of a dialysate source, wherein the single-use microbe/endotoxin filter is configured to remove contaminants from dialysate before the dialysate enters the dialyzer.

A dialyzer configured to be used with a dialysis system is provided, comprising an inlet of the dialyzer being integral with a single-use microbe/endotoxin filter, an inlet of the single-use microbe/endotoxin filter being configured to removably mate with an outlet of a dialysate source, wherein the single-use microbe/endotoxin filter is configured to remove contaminants from dialysate before the dialysate enters the dialyzer.

A pressure measurement device of a dialysis system is provided, comprising a channel configured to carry a flow of blood during dialysis therapy, a flexible membrane comprising at least a section of the channel, wherein fluctuations in pressure of the flow of blood cause the flexible membrane to displace inwards or outwards from the channel, a magnetic core disposed within at least a portion of the flexible membrane, a magnet configured to be magnetically coupled to the magnetic core disposed within the flexible membrane, a force transducer coupled to the magnet, the force transducer being configured to correlate displacement of the flexible membrane with a pressure of the flow of blood, and a temperature sensor disposed within the magnet and configured to contact the flexible membrane to determine a temperature of the flow of blood within the channel.

In some examples, the device further comprises a compliant mount configured to apply a known force against the magnet to maintain a consistent coupling between the magnet and the flexible membrane. In one example, the compliant mount comprises a plurality of axial extensions configured to contact the channel adjacent to the flexible membrane. In another example, the compliant mount further comprises a plurality of shoulder screws with springs coiled around each of the shoulder screws, the shoulder screws being positioned and mounted against a backing plate to eliminate any movement of the force transducer outside of an axial direction of movement.

In some embodiments, the temperature sensor is concentrically disposed within the magnet.

A blood tubing set configured to be mounted to a dialysis system for dialysis therapy is provided, comprising a cassette shell, a fluid tubing circuit disposed within the cassette shell, alignment features disposed on or within the cassette shell, the alignment features being configured to align the cassette with the dialysis system when attaching the cassette shell, and one or more engagement sections disposed within the cassette shell, the one or more engagement sections being configured to assist in fully seating the fluid tubing circuit of the cassette shell within corresponding channels on the dialysis system.

In some embodiments, the engagement sections comprise an abutting ridge configured to press the fluid tubing circuit into a groove or channel of the corresponding flow sensors on the dialysis system.

In another embodiment, the tubing set further comprises a compliant mount disposed on the one or more engagement sections and configured to provide compliance when mounting the cassette shell onto the dialysis system. In some embodiments, the corresponding channels on the dialysis system are associated with sensors, pumps, or pinch valves of the dialysis system.

A dialysis system is provided, comprising a cassette interface panel configured to mate to a cartridge-style patient tubing set, one or more latches disposed within or near the cassette interface panel, the one or more latches being configured to grasp the cartridge-style patient tubing set, and a linear actuator configured to move the cassette interface panel towards the cartridge-style patient tubing set when the cartridge-style patient tubing set is grasped by the one or more latches, wherein the linear actuator causes the cartridge-style patient tubing set to be fully engaged with the cassette interface panel.

In some embodiments, the cartridge-style patient tubing set is installed within one or more sensors of the dialysis system when it is fully engaged with the cassette interface panel.

A method of mounting a cartridge-style patient tubing set onto a dialysis machine is provided, comprising placing the cartridge-style patient tubing set into latches of a cassette interface panel of the dialysis machine, automatically detecting, with the dialysis machine, that the cartridge-style patient tubing set has been placed into the latches, moving the cassette interface panel of the dialysis machine towards the cartridge-style patient tubing set with a linear actuator, and fully engaging the cartridge-style patient tubing set with the cassette interface panel of the dialysis machine.

A method preparing a dialysis machine for dialysis therapy, comprising connecting an arterial line of an extracorporeal circuit to a venous line of the extracorporeal circuit with a union joint, flowing a priming solution through the extracorporeal circuit of the dialysis machine to remove gas from the extracorporeal circuit, connecting the union joint to a flush/drain pathway of the dialysis system, operating a drainage pump to remove the priming solution from the extracorporeal circuit and through the flush/drain pathway, removing the union joint from the flush/drain pathway, connecting dialysate lines to the flush/drain pathway, and operating a dialysate pump and/or the drainage pump to flow dialysate through the dialysate lines to disinfect the dialysate lines.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 21A-21D illustrate embodiments of a flow chamber for a dialysis system.

FIGS. 38A-38C illustrate various embodiments of a pressure measurement device of a dialysis system.

FIG. 41 is a detailed view of a cassette and patient tubing set.

FIGS. 42A-42B illustrate one embodiment of a cassette and patient tubing set having two clamshell sections.

FIGS. 47A-47C illustrate a flow path configured to rinse and drain fluid into/from an extracorporeal circuit of a dialysis system.

DETAILED DESCRIPTION

This disclosure describes systems, devices, and methods related to dialysis therapy, including a dialysis system that is simple to use and includes automated features that eliminate or reduce the need for technician involvement during dialysis therapy. In some embodiments, the dialysis system can be a home dialysis system. Embodiments of the dialysis system can include various features that automate and improve the performance, efficiency, and safety of dialysis therapy.

In some embodiments, a dialysis system is described that can provide acute and chronic dialysis therapy to users. The system can include a water purification system configured to prepare water for use in dialysis therapy in real-time using available water sources, and a dialysis delivery system configured to prepare the dialysate for dialysis therapy. The dialysis system can include a disposable cartridge and tubing set for connecting to the user during dialysis therapy to retrieve and deliver blood from the user.

Figure 1:
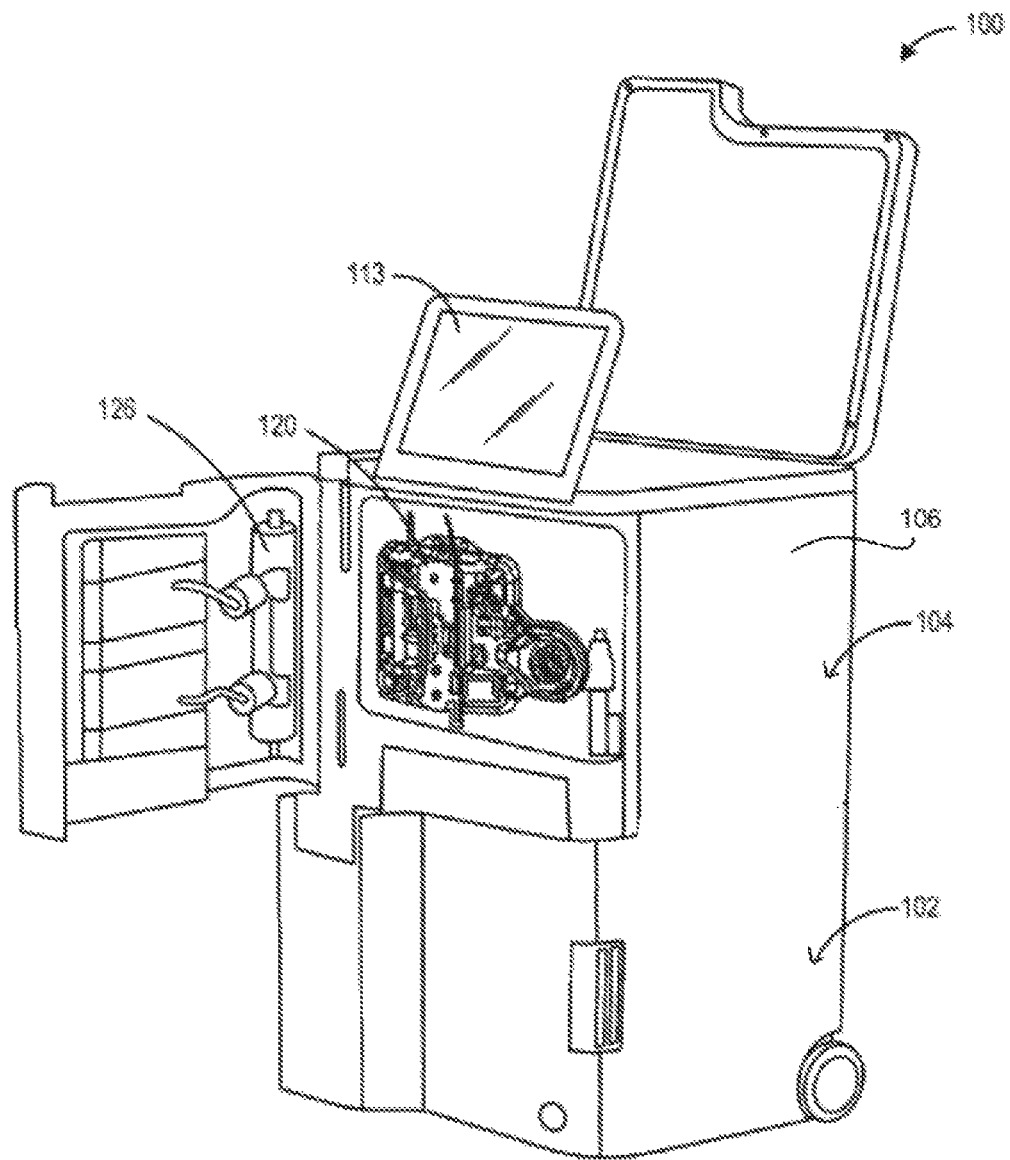
FIG. 1 shows one embodiment of a dialysis system.

FIG. 1 illustrates one embodiment of a dialysis system 100 configured to provide dialysis treatment to a user in either a clinical or non-clinical setting, such as the user's home. The dialysis system 100 can comprise a water purification system 102 and a dialysis delivery system 104 disposed within a housing 106. The water purification system 102 can be configured to purify a water source in real-time for dialysis therapy. For example, the water purification system can be connected to a residential water source (e.g., tap water) and prepare pasteurized water in real-time. The pasteurized water can then be used for dialysis therapy (e.g., with the dialysis delivery system) without the need to heat and cool large batched quantities of water typically associated with water purification methodologies.

Dialysis system 100 can also include a cartridge 120 which can be removably coupled to the housing 106 of the system. The cartridge can include a patient tubing set attached to an organizer. The cartridge and tubing set, which can be sterile, disposable, one-time use components, are configured to connect to the dialysis system prior to therapy. This connection correctly aligns corresponding components between the cartridge, tubing set, and dialysis system prior to dialysis therapy. For example, the tubing set is automatically associated with one or more pumps (e.g., peristaltic pumps), clamps and sensors for drawing and pumping the user's blood through the tubing set when the cartridge is coupled to the dialysis system. The tubing set can also be associated with a saline source of the dialysis system for automated priming and air removal prior to therapy. In some embodiments, the cartridge and tubing set can be connected to a dialyzer 126 of the dialysis system. In other embodiments, the cartridge and tubing set can include a built-in dialyzer that is pre-attached to the tubing set. A user or patient can interact with the dialysis system via a user interface 113 including a display.

Figure 2:
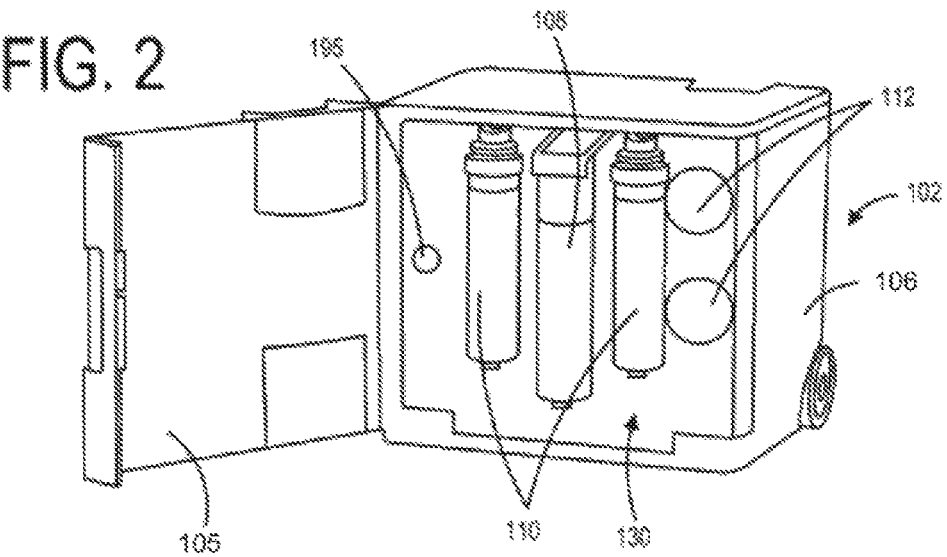
FIG. 2 illustrates one embodiment of a water purification system of the dialysis system.
Figure 3:
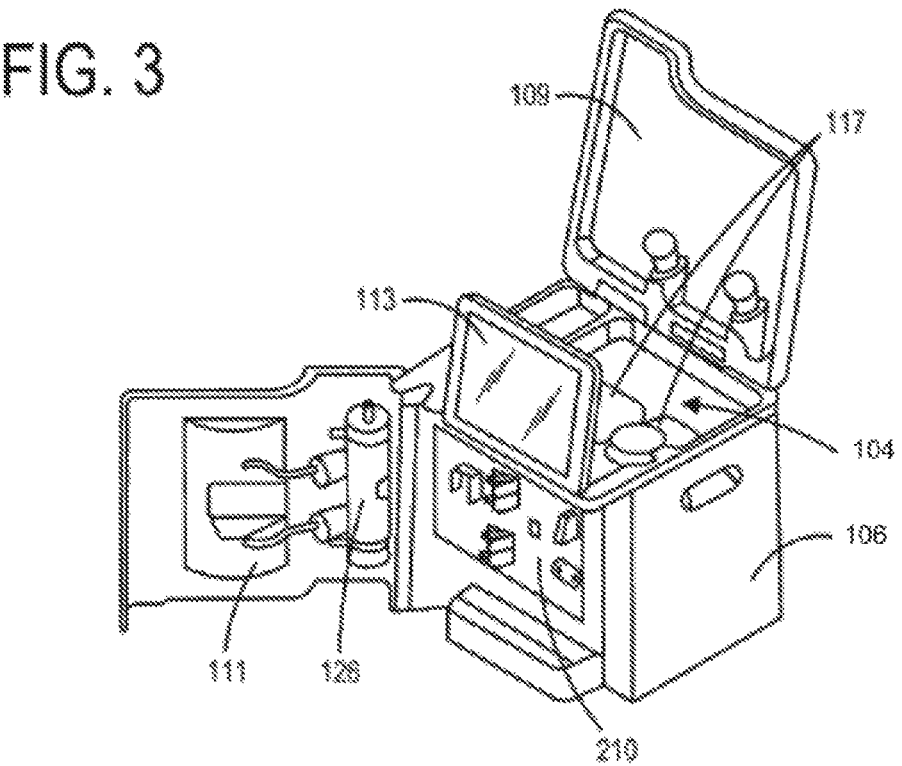
FIG. 3 illustrates one embodiment of a dialysis delivery system of the dialysis system.

FIGS. 2-3 illustrate the water purification system 102 and the dialysis delivery system 104, respectively, of one embodiment of the dialysis system 100. The two systems are illustrated and described separately for ease of explanation, but it should be understood that both systems can be included in a single housing 106 of the dialysis system. FIG. 2 illustrates one embodiment of the water purification system 102 contained within housing 106 that can include a front door 105 (shown in the open position). The front door 105 can provide access to features associated with the water purification system such as one or more filters, including sediment filter(s) 108, carbon filter(s) 110, and reverse osmosis (RO) filter(s) 112. The filters can be configured to assist in purifying water from a water source (such as tap water) in fluid communication with the water purification system 102. The water purification system can further include heating and cooling elements, including heat exchangers, configured to pasteurize and control fluid temperatures in the system, as will be described in more detail below. The system can optionally include a chlorine sample port 195 to provide samples of the fluid for measuring chlorine content.

In FIG. 3, the dialysis delivery system 104 contained within housing 106 can include an upper lid 109 and front door 111, both shown in the open position. The upper lid 109 can open to allow access to various features of the dialysis system, such as user interface 113 (e.g., a computing device including an electronic controller and a display such as a touch screen) and dialysate containers 117. Front door 111 can open and close to allow access to front panel 210, which can include a variety of features configured to interact with cartridge 120 and its associated tubing set, including alignment and attachment features configured to couple the cartridge 120 to the dialysis system 100. Dialyzer 126 can be mounted in front door 111 or on the front panel, and can include lines or ports connecting the dialyzer to the prepared dialysate as well as to the tubing set of the cartridge.

In some embodiments, the dialysis system 100 can also include a blood pressure cuff to provide for real-time monitoring of user blood pressure. The system (i.e., the electronic controller of the system) can be configured to monitor the blood pressure of the user during dialysis therapy. If the blood pressure of the user drops below a threshold value (e.g., a blood pressure threshold that indicates the user is hypotonic), the system can alert the user with a low blood pressure alarm and the dialysis therapy can be stopped. In the event that the user ignores a configurable number of low blood pressure alarms from the system, the system can be configured to automatically stop the dialysis therapy, at which point the system can inform the user that return of the user's blood (the blood that remains in the tubing set and dialyzer) back to the user's body is necessary. For example, the system can be pre-programmed to automatically stop therapy if the user ignores three low blood pressure alarms. In other embodiments, the system can give the user a bolus of saline to bring user fluid levels back up before resuming dialysis therapy. The amount of saline delivered to the patient can be tracked and accounted for during ultrafiltration fluid removal.

The dialysis delivery system 104 of FIG. 3 can be configured to automatically prepare dialysate fluid with purified water supplied by the water purification system 102 of FIG. 2. Furthermore, the dialysis delivery system can de-aerate the purified water, and proportion and mix in acid and bicarbonate concentrates from dialysate containers 117. The resulting dialysate fluid can be passed through one or more ultrafilters (described below) to ensure the dialysate fluid meets certain regulatory limits for microbial and endotoxin contaminants.

Dialysis can be performed in the dialysis delivery system 104 of the dialysis system 100 by passing a user's blood and dialysate through dialyzer 126. The dialysis system 100 can include an electronic controller configured to manage various flow control devices and features for regulating the flow of dialysate and blood to and from the dialyzer in order to achieve different types of dialysis, including hemodialysis, ultrafiltration, and hemodiafiltration.

Figure 4:
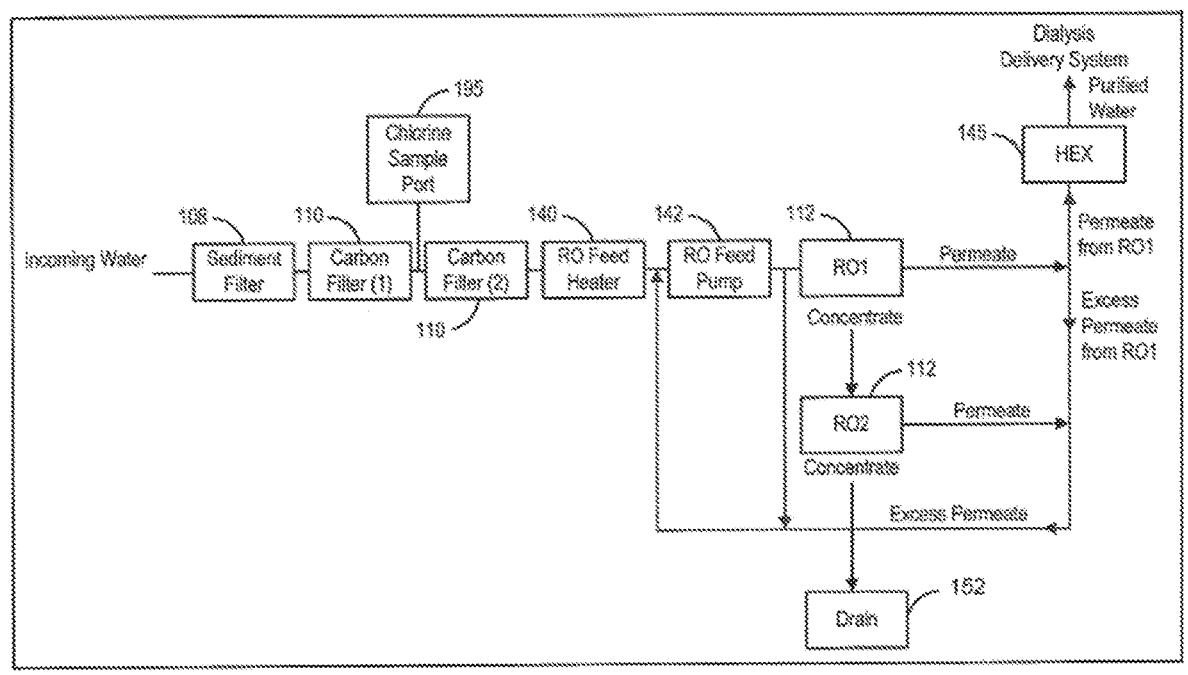
FIG. 4 shows a flow diagram of the water purification system contained within the dialysis system.

FIG. 4 shows a flow diagram of the water purification system 102 contained within the dialysis system 100. Incoming water, such as from the tap, can flow through a number of filters, including one or more sediment filters 108 and one or more carbon filters 110. A chlorine sample port 195 can be placed between the carbon filters 110 to provide samples of the fluid for measuring chlorine content. Redundant or dual carbon filters can be used to protect the system and the user in the event of a carbon filter failure. The water can then pass through a reverse osmosis (RO) feed heater 140, a RO feed pump 142, one or more RO filters 112 (shown as RO1 and RO2), and a heat exchanger (HEX) 144. Permeate from the RO filters 112 can be delivered to the HEX 144, while excess permeate can be passively recirculated to pass through the RO feed pump and RO filters again. The recirculation helps with operating of the water purification system by diluting the incoming tap water with RO water to achieve higher rejection of salts from incoming water. After passing through the HEX 144, the purified water can be sent to the dialysis delivery system 104 for preparing dialysate and assisting with dialysis treatments. Additionally, concentrate from the RO filters during the water purification process can be sent to drain 152.

Figure 5:
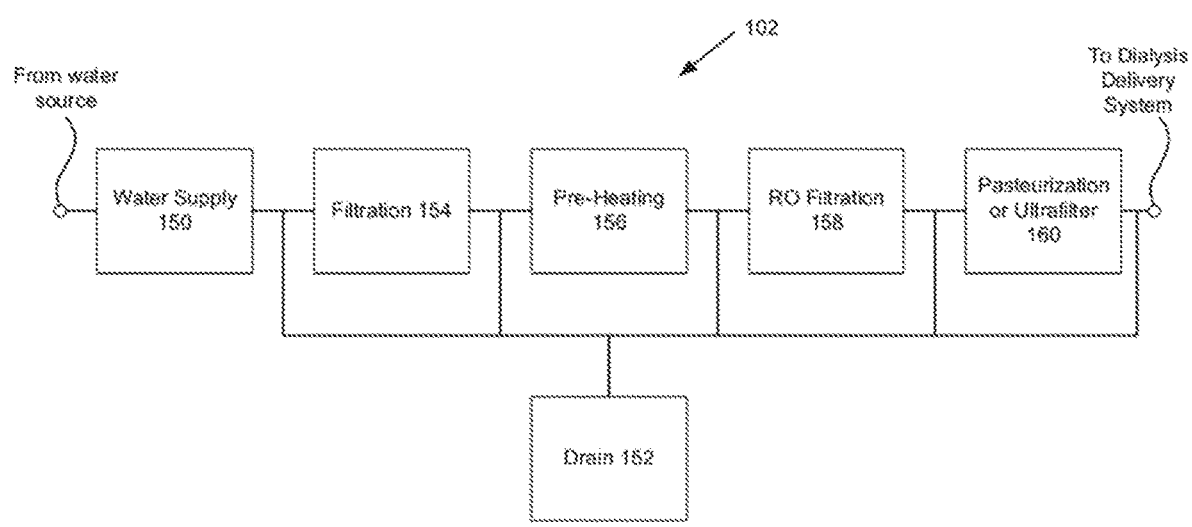
FIG. 5 is a schematic diagram showing a water supply subsystem, a filtration subsystem, a pre-heating subsystem, an RO filtration subsystem, and a pasteurization subsystem of the water purification system of the dialysis system.

Referring to FIG. 5, the water purification system 102 of the dialysis system can include one or more subsystems as described above in FIG. 4, including a water supply subsystem 150, a filtration subsystem 154, a pre-heating subsystem 156, an RO filtration subsystem 158, and a pasteurization or ultrafiltration subsystem 160. Each of the subsystems above can produce output to a drain 152. The water purification system 102 can be configured to purify a water source in real-time for dialysis therapy. For example, the water purification system can be connected to a residential water source (e.g., tap water) and prepare purified water in real-time. The purified water can then be used for dialysis therapy (e.g., with the dialysis delivery system) without the need to heat and cool large batched quantities of water typically associated with water purification methodologies.

Figure 6:
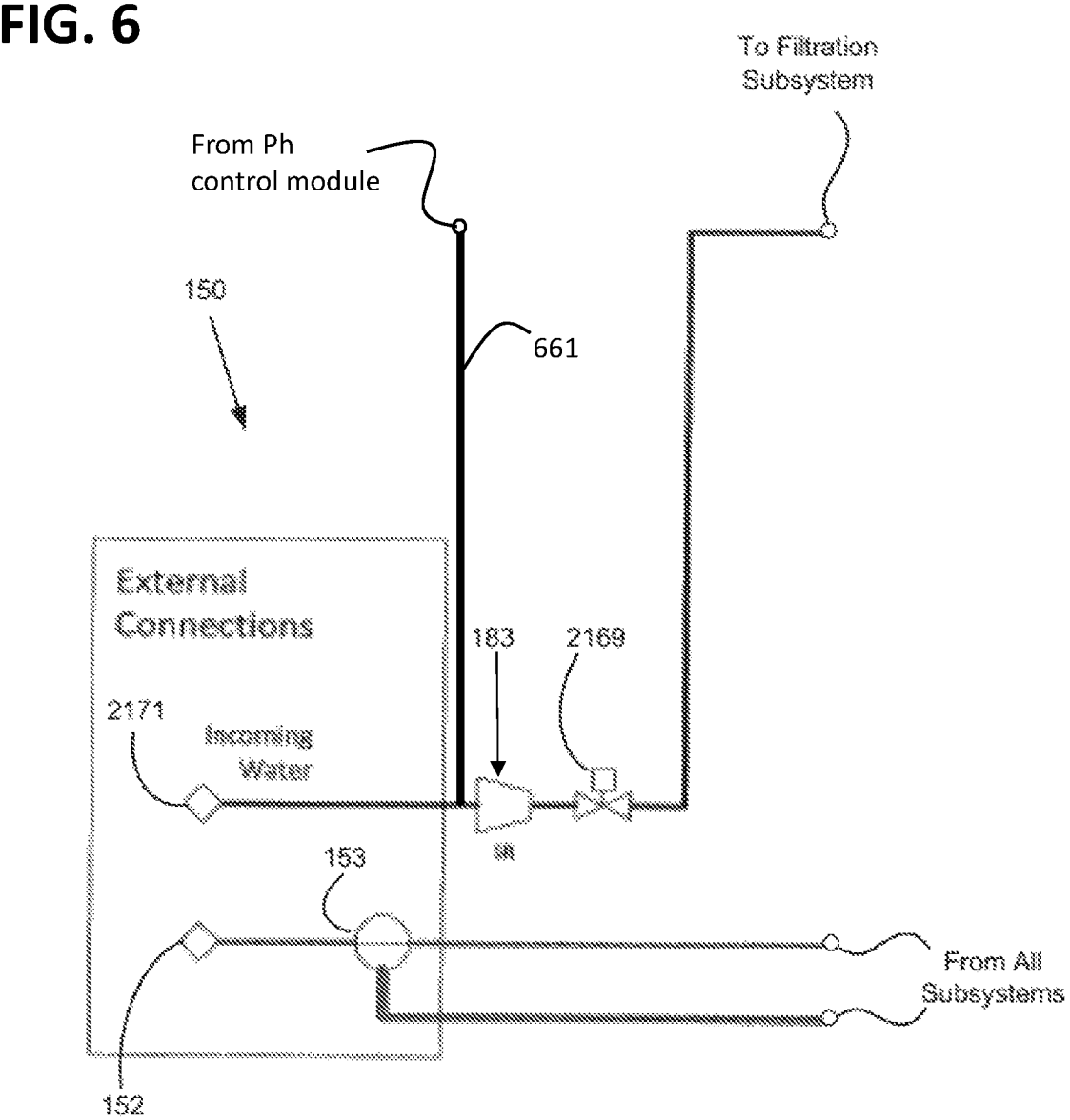
FIG. 6 shows the features of the water supply subsystem of the water purification system.
Figure 7:
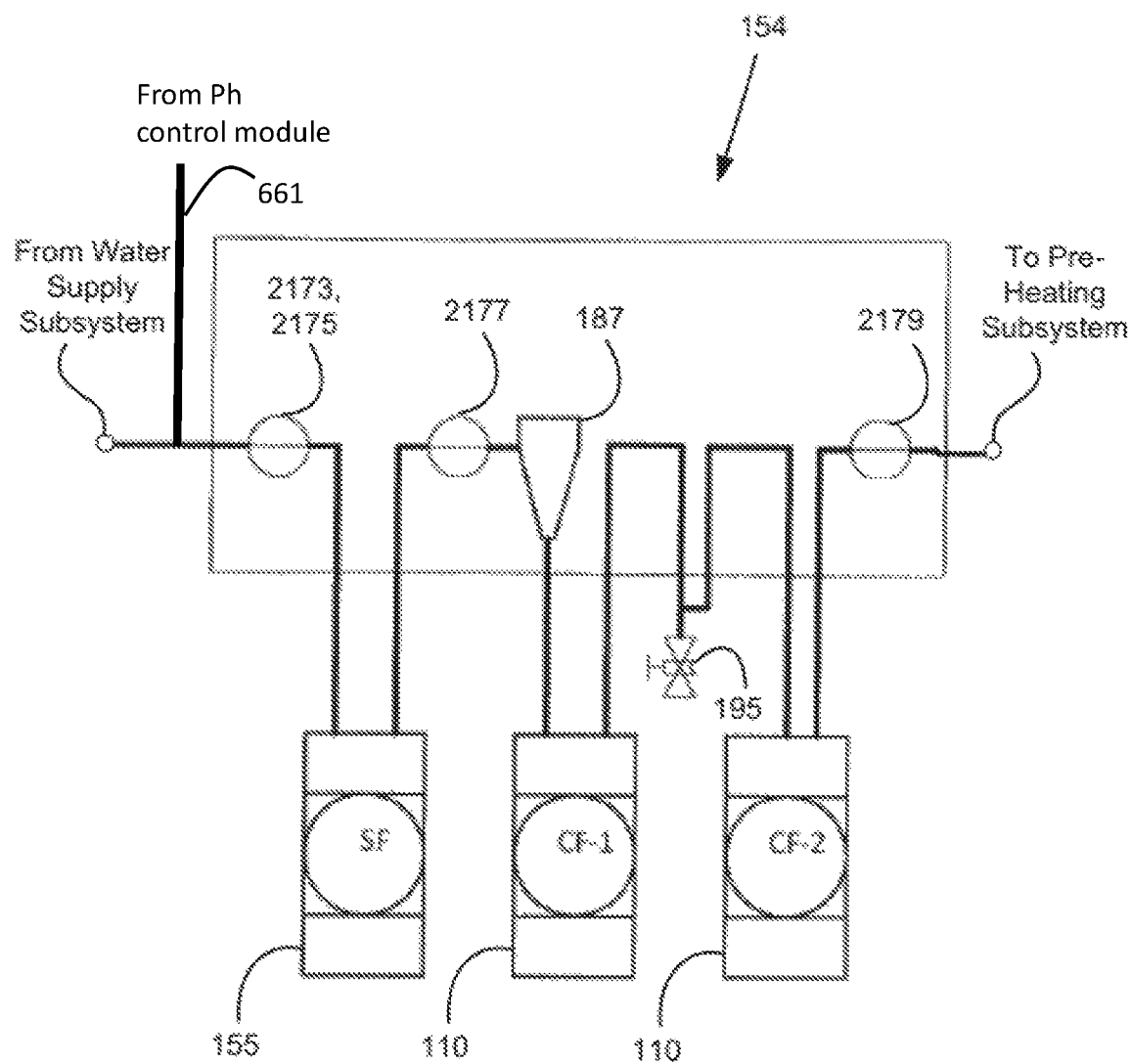
FIG. 7 shows one embodiment of a filtration subsystem of the water purification system.
Figure 8:
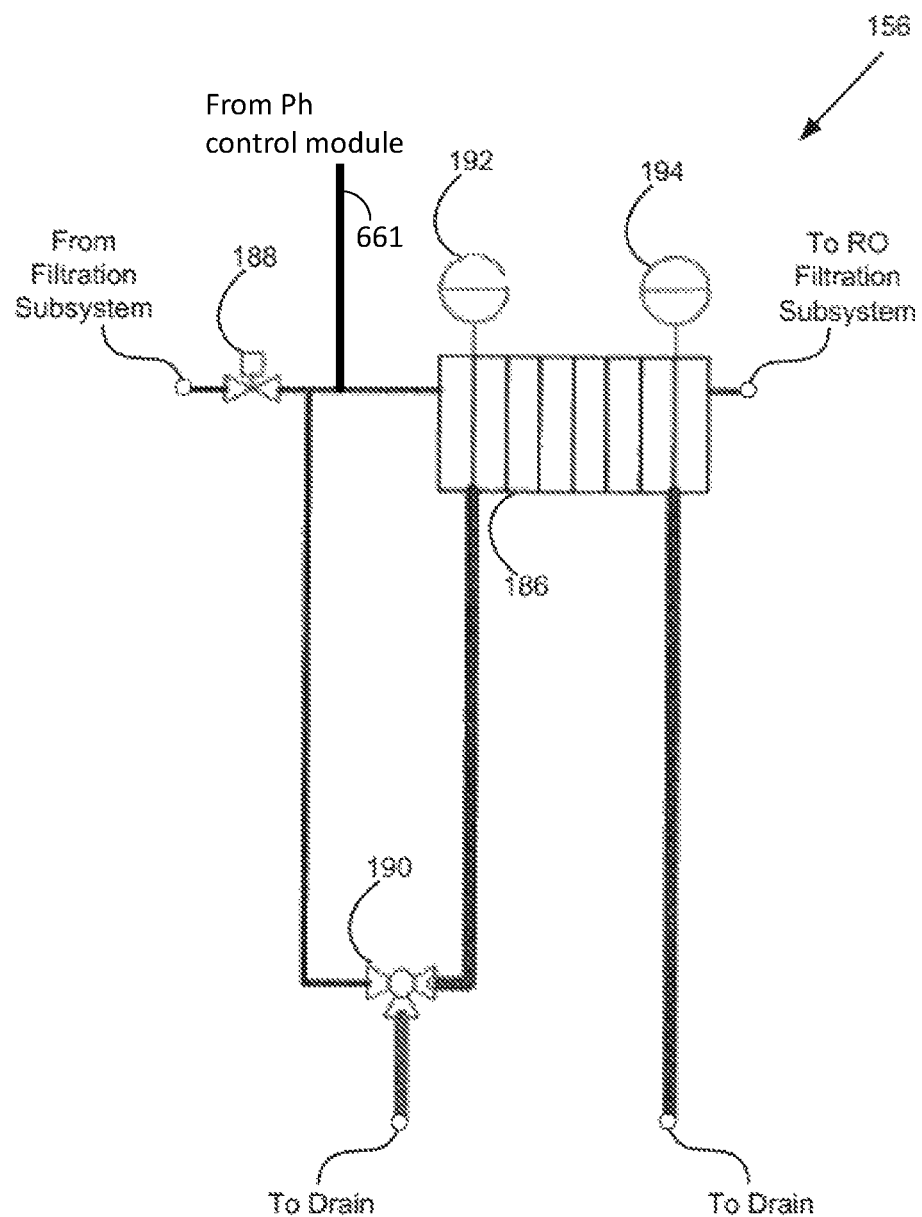
FIG. 8 shows one embodiment of a pre-heating subsystem of the water purification system.
Figure 9:
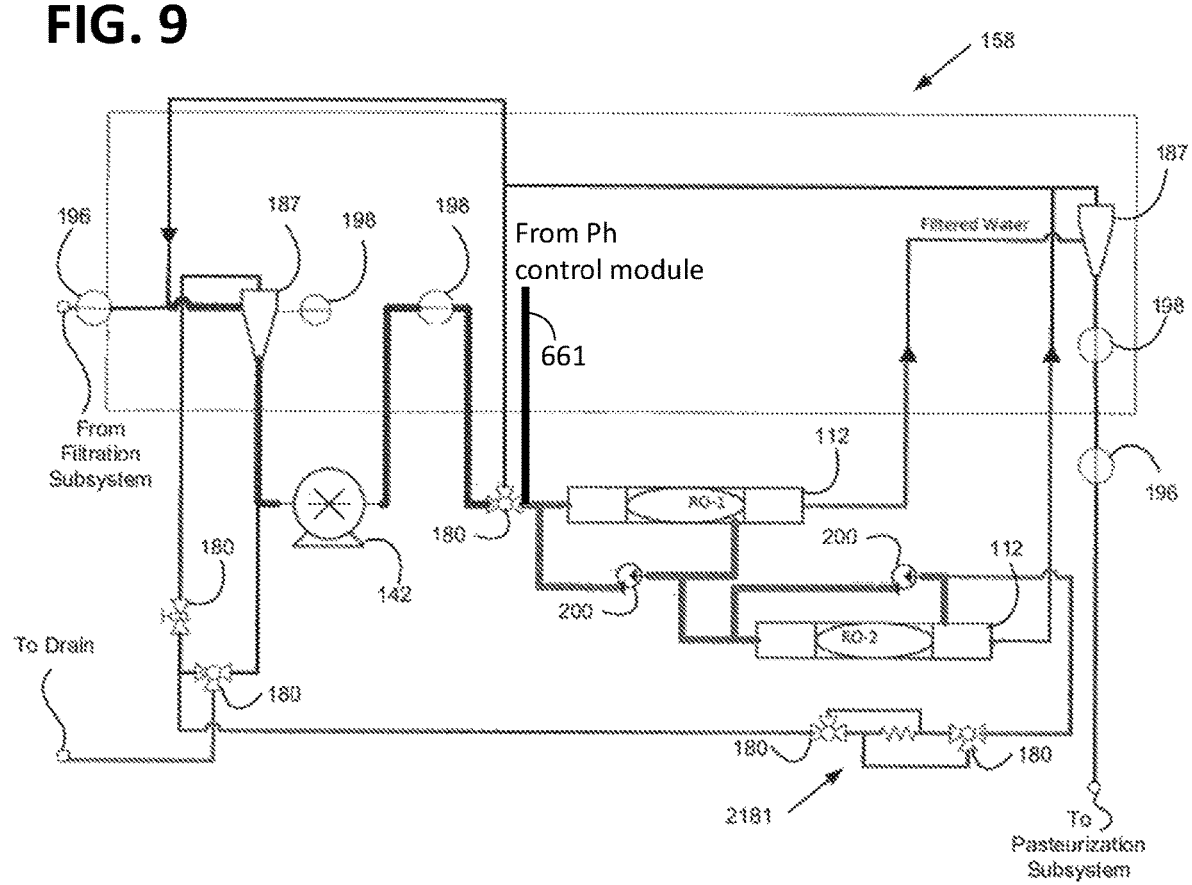
FIG. 9 shows one embodiment of a RO filtration subsystem of the water purification system.

FIG. 6 shows the features of the water supply subsystem 150 of the water purification system, which can include a variety of valves (e.g., three-way valves, control valves, etc.) for controlling fluid flow through the water purification system. For example, at least one valve 2169 can be opened to allow water to flow into the water purification system for purification. The incoming water can flow in from a tap water source 2171, for example. Fluid returning from the water purification system can be directed to drain 152 through one or more of the valves. Furthermore, the subsystem can include a supply regulator 183 that can adjust the water supply pressure to a set value. The water supply subsystem 150 can further include a pH control line 661 that connects into the fluid path after the tap water source 2171. As shown in FIG. 6, the pH control line 661 enters the fluid path after the tap water source 2171 but before the supply regulator 183. It should be understood, however, that the pH control line 661 can enter the dialysis system at any point in the fluid path after the tap water source 2171 but prior to the reverse osmosis (RO) filter(s) (e.g., RO filter(s) 112 of FIGS. 2-3). Thus, optional connections for the pH control line 661 are shown in FIGS. 7, 8, and 9. The pH control line 661 is configured to allow for the transfer of acid and base concentrates from a pH control module (described below) into the water supply line to balance incoming water for improved water filtration efficiency. A drain pressure sensor 153 can measure the pressure at the drain. Water can flow from the water supply subsystem 150 on to the filtration subsystem, described next.

FIG. 7 shows one embodiment of a filtration subsystem 154 of the water purification system. The filtration subsystem can receive water from the water supply subsystem 150 described in FIG. 6. Water can first pass through a supply pressure sensor 2173 configured to measure the water pressure and a supply temperature sensor 2175 configured to sense the temperature of the incoming water supply. In this embodiment, the PH control line 661 joins the fluid path immediately prior to the supply pressure sensor and supply temperature pressure. However it should be understood that the pH control line 661 can join the fluid path at a position prior to, within, or after the filtration subsystem. The filtration subsystem can include a sediment filter 155, for example, a 5-micron polypropylene cartridge filter. The filter typically requires replacement every 6 months. Based on the high capacity of the sediment filter and the relatively low flow rate through the filter, the life expectancy is estimated to be over 1 year based on the average municipal water quality in the US. A replacement interval of 6 months provides high assurance that premature sediment filter fouling should be rare. Also, expected to be a rare occurrence based on the construction and materials of the filter is a failure that results in unfiltered water passing through the filter. A post-sediment pressure sensor 2177 can measure the pressure drop across the sediment filter to monitor and identify when the sediment filter needs to be replaced. Should the sediment filter allow unfiltered water to pass the result would be fouling of the carbon filters which would be detected by a pressure drop at post-sediment pressure sensor 2177. If this pressure drop is the significant factor when the sensor drops to 5 psig, the system will require replacement of both the carbon filters and the sediment filters prior to initiating therapy.

The water can then flow through one or more carbon filters 110 (shown as CF-1 and CF-2) configured to filter materials such as organic chemicals, chlorine, and chloramines from the water. For example, the carbon filters 110 can include granulated carbon block cartridges having 10-micron filters. The carbon filters can be connected in series with a chlorine sample port 195 positioned in the flow path between the carbon filters. The chlorine sample port can provide a user with access (such as through the front panel of the system) to the flowing water such as for quality control purposes to ensure the total chlorine concentration level of the water is below a certain threshold (e.g., below 0.1 ppm). Additionally, a post-carbon pressure sensor 2179 can be placed after the carbon filter(s) to monitor the fluid pressure in the line after the sediment and carbon filtration.

FIG. 8 shows one embodiment of a pre-heating subsystem 156 of the water purification system. The pre-heating subsystem can be configured to control the temperature of water in the line to optimize RO filtration performance. The pre-heating subsystem can include one or more RO feed heaters 186, which can comprise, for example a thermoelectric device such as a Peltier heater/cooler. The RO feed heater 186 can be configured to regulate or adjust the temperature of the water before RO filtration. In one embodiment, the target temperature for reverse osmosis is 25 degrees C. for optimal RO filter performance. If the water is too cold the RO filters will have insufficient flow and the system will not make enough water. If the water is too warm the RO filters will allow more flow but also have reduced salt rejection. In one embodiment, 25° C. is the point at which flow and rejection are balanced to provide sufficient water volume with adequate rejection. The RO feed heater can be used to both heat or cool the fluid flowing through the heater. For example, in some embodiments, the RO feed heater can recover heat from waste water or used dialysate by way of the Peltier effect. In other embodiments, such as during a heat disinfect cycle, the RO feed heater can be placed in opposing polarity to negate Peltier effects. During water treatment, the incoming water flows through a titanium plate attached to the hot side of two thermoelectric wafers of the RO feed heater. Waste water can be directed through a separate titanium plate attached to the cold side of the wafers. Heat is therefore pumped from the waste water to the incoming water via the Peltier effect. At maximum power when the preheating system achieves a coefficient of performance of two, meaning half of the power heating the incoming water is recovered from waste water and the other half is from the electrical heating of the wafers. At lower power levels the coefficient of performance is higher meaning a higher percentage of the heat is recovered from the waste stream. During heat disinfect the thermoelectric wafers of the RO feed heater can be placed in opposing polarity. In this way both titanium plates are heated and the Peltier effect is negated. This ensures that the water is heated only and is always above the incoming temp on either side of the heater.

As shown in FIG. 8, the pre-heating subsystem 156 can include a process supply valve 188 in the line between the filtration subsystem and the RO feed heater, and a used dialysate return valve 190 for routing used dialysate to the drain. The RO feed heater can include a pair of temperature sensors 192 and 194 to measure the temperature of the fluid on either side of the heater. Water can flow from the pre-heating subsystem to the RO filtration subsystem, described next. In this embodiment, the PH control line 661 joins the fluid path between the process supply valve 188 and the peltier cooler 186. However it should be understood that the pH control line 661 can join the fluid path at a position prior to, within, or after the pre-heating subsystem.

FIG. 9 shows one embodiment of a RO filtration subsystem 158 of the water purification system. The RO filtration subsystem can receive pre-heated water from the pre-heating subsystem described above. The RO filtration subsystem can include a RO feed pump 142 that can drive water across one or more RO filters 112 (shown as RO-1 and RO-2) to produce a permeate flow and a concentrate flow. The concentrate flow can be filtered by more than one RO filter. In addition, the permeate flow can be combined with excess permeate and be recirculated back to blend with incoming water. In addition, each RO filter 112 can include a recirculation pump 200 to keep fluidic line flow velocity high over the RO filters. The recirculation pumps can run at a constant velocity, driving any flow emanating from the concentrate flow back into the inlet of the RO filters. Using a separate recirculation pump instead of recirculating through the RO feed pump lowers overall power consumption and keeps flow velocity over the RO membranes high to reducing fouling and allow for high water production rates. In some embodiments, the RO feed pump can be high pressure but relatively low flow pumps compared to the recirculation pump(s), which can be low pressure but high flow pumps.

The pressure created by the RO feed pump and a RO concentrate flow restrictor 2181 can control the flow rate of waste to the drain. To ensure that the restriction does not become fouled or plugged, the flow through the RO concentrate flow restrictor can be periodically reversed by actuating valves 180. In addition, to improve filter life and performance, recirculation pumps can be used to increase fluid flow rate in the RO filter housings. This increase in flow rate can serve to reduce a boundary layer effect that can occur near the surface of RO filters where water near the filter membrane may not flow. The boundary layer can create an area with a higher concentration of total dissolved solids that can build up over the surface of the RO filter and may collect and foul the RO filter.

The RO filtration subsystem can include on or more conductivity sensors 196 configured to measure the conductivity of water flowing through the subsystem to measure solute clearance, or per, pressure sensors 198 configured to monitor fluid pressures, and air separators 187 configured to separate and remove air and air bubbles from the fluid. Additionally, the RO filtration subsystem can include a variety of valves 180, including check valves, and fluid pumps for controlling flow through the RO filters and on to the pasteurization subsystem, back through the RO filtration subsystem for further filtration, or to the drain. In this embodiment, the PH control line 661 joins the fluid path between the first RO filter 112 and RO feed pump 142. However it should be understood that the pH control line 661 can join the fluid path at a position prior to, within, or after the RO filtration subsystem. Water can flow from the RO filtration subsystem to the pasteurization subsystem, described next.

Figure 10:
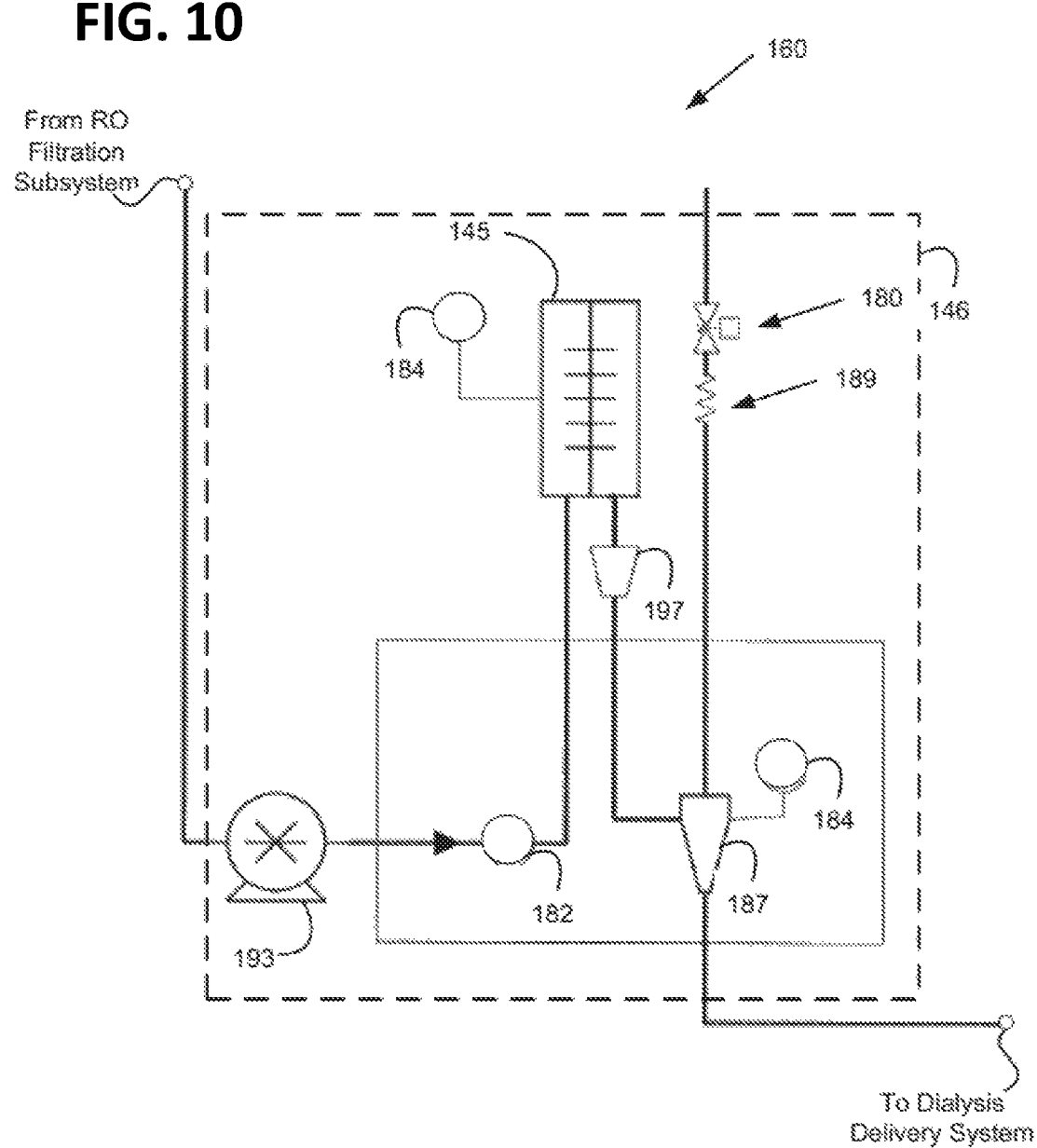
FIG. 10 illustrates one embodiment of a pasteurization subsystem of the water preparation system.

FIG. 10 illustrates one embodiment of an optional pasteurization subsystem 160 of the water preparation system. The pasteurization subsystem can be configured to minimize patient exposure to microbiological contamination by heating the fluid to eliminate microbiological contamination and endotoxins from the system. The pasteurization subsystem can include a heat exchanger (HEX) 145 configured to heat water to pasteurization temperature, allow the water to dwell at the high temperature, and then cool the water back to a safe temperature for the creation of dialysate.

In some embodiments, the HEX 145 can heat water received by the pasteurization subsystem to a temperature of approximately 148 degrees Celsius. The heated water can be held in a dwell chamber of the HEX for a time period sufficient to eliminate and kill bacteria and denature endotoxins. Endotoxins can be described as the carcasses of dead bacteria, characterized by long lipid chains. During water and dialysate preparation, endotoxins can be monitored along with bacteria to judge the purity of the dialysate. Endotoxins in dialysate can cause an undesirable inflammatory response in users. Therefore, it is desirable to minimize the levels of endotoxin in the dialysate. Endotoxins are not readily trapped by the pore size of typical ultrafilters. Instead, the endotoxins are stopped by ultrafilters through surface adsorption which can become saturated with endotoxins to the point that additional endotoxin will start to pass through. Heating endotoxins in superheated water to temperatures as low as 130 degrees C. have been demonstrated to denature endotoxins but the required dwell time is very long (many minutes). At these elevated temperatures, where the water remains in the liquid phase, water which is typically considered a polar solvent and begins to behave like a non-polar solvent to denature the lipid chains of the endotoxin. As the temperature increases to 220 degrees C. or higher, the denaturing of endotoxins occurs in seconds. The HEX of the present disclosure can run at 220 degrees C. or higher while maintaining a pressure (approximately 340 psi for 220 degrees C., but the HEX can withstand pressures of over 1000 psi) that keeps the water in liquid form. In one embodiment, a preferred temperature and pressure range of the HEX is 180-220 degrees C. and 145-340 psi. The water can then be cooled as it exits the dwell chamber. The HEX 145 is a self-contained counterflow heat exchanger that simultaneously heats incoming water and cools outgoing water to reduce energy consumption.

The pasteurization subsystem can include a HEX pump 193 configured to maintain a fluid pressure in the fluid line, to prevent the water from boiling. After the water passes through the HEX 145, a water regulator 197 can reduce the pressure of the water for use in the dialysis delivery system. One or more pressure sensors 182 or temperature sensors 184 can be included for measuring pressure and temperature, respectively, of the water flowing through the pasteurization subsystem. Furthermore, an air separator 187 can further remove air and air bubbles from the water. In one embodiment, a flow restrictor 189 and valve 180 can be used to limit water dumped to the drain when the HEX 145 is heating up. Once the water has passed through the pasteurization subsystem, it has traveled through the entire water purification system and is clean and pure enough to be used in dialysate preparation and delivery by the dialysis delivery system.

As is also shown in FIG. 10, an optional air separator 187 can be placed between the sediment filter and the carbon filter(s) to remove excess air and bubbles from the line. In some embodiments, each carbon filter can specified to have a service life of 2500 gallons producing water that has less than 0.5 ppm of free chlorine and chloramine when operating in high chlorine conditions and at a higher flow rate than the instrument supports so an expected life of greater than 2500 gallons is expected. Based on a maximum treatment flow rate of 400 mL/min through the carbon filters the expected for a single carbon filter is approximately 6 months to a year or more depending on incoming water quality. The system typically requires replacement of both filters every 6 months. Most carbon filters cannot tolerate heat or chemical disinfection, therefore a recirculation/disinfection fluid path, implemented by the water supply and drain systems, does not include the carbon filters (or the sediment filters). Since the chlorine absorption capacity of carbon filters is finite and dependent on the incoming water quality, a water sample from the chlorine sample port 195 can be taken to verify that the water has a free chlorine concentration level of less than 0.1 ppm. Using the two stage carbon filtration and verifying the "equivalent absence" of free chlorine after the first carbon filter ensures that the second carbon filter remains at full capacity in complete redundancy to the first. When the first carbon filter does expire, both filters are typically replaced. Water can flow from the filtration subsystem to the pre-heating subsystem, described next.

Figure 11:
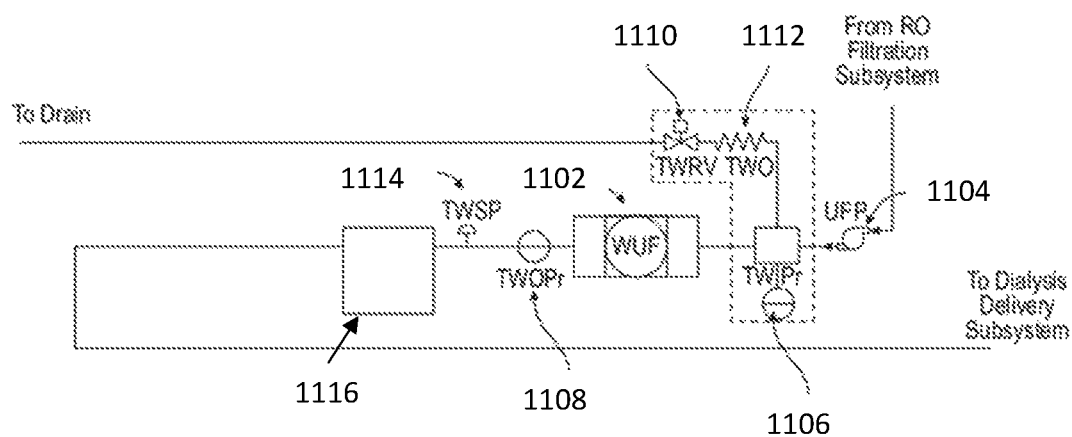
FIG. 11 illustrates a different embodiment of an ultrafiltration subsystem that may be used in place of pasteurization subsystem of FIG. 10.

FIG. 11 illustrates a different embodiment of an ultrafiltration subsystem that may be used in place of pasteurization subsystem of FIG. 10. This ultrafiltration subsystem uses a nanometer scale filter (ultrafilter) 1102 to remove microbiological contamination and endotoxins from the system. In some embodiments, the pore size of the ultrafilter is 5 nanometers. In some embodiments, the material of the ultrafilter is polysulfone, although the ultrafilter may comprise any material known in the art that may be fashioned into a filter structure of sufficient porosity. The ultrafiltration subsystem can include a booster pump 1104 to provide enough pressure to drive the flow of water through the ultrafilter. The pressure across the filter can be monitored by an upstream pressure sensor 1106 and a downstream pressure sensor 1108, which can alert the user of the filter has been clogged and needs to be changed. Flow maybe diverted to drain through a drain valve 1110 and restrictor 1112 if needed. The ultrafiltration subsystem also comprises a sample port 1114 accessible from the exterior of the system for drawing water to confirm proper functionality of the ultrafilter. In some embodiments, the ultrafiltration subsystem may comprise flow through a heat exchanger 1116 to facilitate cooling or heating of fluid paths elsewhere in the system architecture.

Figure 12:
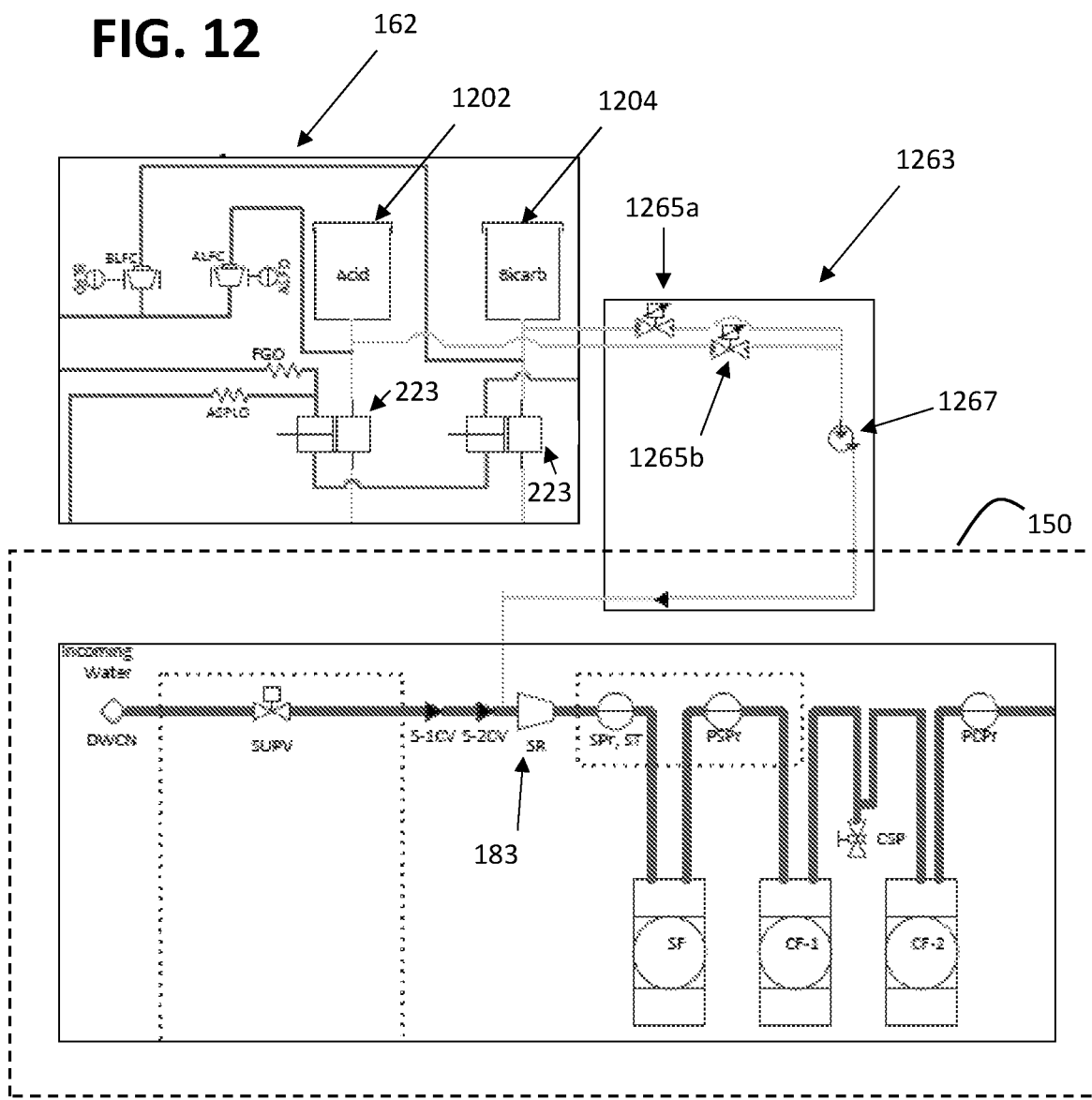
FIG. 12 illustrates a schematic of a mixing subsystem of the dialysis delivery system.

FIG. 12 illustrates a schematic of a mixing subsystem 162 and a pH control module 1263 of the dialysis delivery system. The dashed rectangle 150 represents water supply subsystem 150 from FIG. 6 above. Referring to mixing subsystem 162, acid concentrate and bicarbonate concentrates can be volumetrically proportioned into the fluid path from acid source 1202 and bicarb source 1204 by way of concentrate pumps 223 in order to reach the desired dialysate composition. The water and concentrates can be mixed in a series of mixing chambers (not shown) that utilize a time delay or volumetric mixing instead of in-line mixing to smooth the introduction of fluids.

In recent years more and more municipalities have transitioned from using chlorine to sanitize tap water to chloramines. Chloramines are formed when chlorine is bonded to an ammonia molecule. Initially this was to control ammonia in the tap water, but it was found that chloramines maintain a similar sanitizing property found in chlorine but do not evaporate as quickly. Due to its increased longevity chloramines have seen a rise in popularity as a sanitizing agent as it requires less cost to maintain. In a typical dialysis system, when the chloramines in the incoming tap water react with the carbon filters in the system, the chlorine is stripped off, freeing the ammonia. This can cause issues with post RO rejection rates. In high pH water, ammonia primarily exists as a non-ionized form $NH_3$, which makes it difficult for the RO membranes to filter out. RO membranes are known to increase in pore size at elevated pH, which causes an increase in dissolved salts to pass through them, resulting in lowered rejection. This decreases the filter efficacy. In thin film composite RO membranes, rejection performance may degrade as the pH rises above 9.0, and has optimal performance around pH 7.0. It is also known in the art that other chemical constituents of the water, such as weak alkaline species, act as buffering agents. In the presence of these buffering agents, substances introduced with a lower pH will have a smaller effect on the pH of the solution than in the absence of buffering agents.

However, the pH control module 1263 of FIG. 12 is configured to lower the pH of water coming into the dialysis system in the water supply subsystem 150 by ionizing the ammonia to ammonium $NH_4^+$ which is readily rejected by the RO membranes of the RO filtration subsystem described above. By modifying the incoming acidity of the incoming water, the RO subsystem is better able to remove contaminates and improve overall quality of the dialysate. In addition, the mixing subsystem 162 uses less acid concentrate than base concentrate on a per-volume basis.

The pH control module 1263 can be positioned in the fluid path between the mixing subsystem 162 and the water supply subsystem 150. Proportioning valves 1265a and 1265b can be coupled to the acid and bicarbonate concentrate containers and be configured (via a controller of the dialysis system) to allow measured amounts of acid and bicarbonate to be introduced to the incoming water in the water supply subsystem 150 to lower or adjust the pH of the incoming water, at a point in the fluid path just before the supply regulator 183. In other embodiments the concentrates may be introduced immediately prior to the RO membranes, after the carbon and sediment filters. In other embodiments, the concentrates may be introduced in between two of the sediment or carbon filters. A gear pump 1267 or other type of pump known in the art can be configured to generate the needed pressures to move the concentrates from the mixing subsystem 162 into the water supply subsystem 150. In some embodiments, a check valve can be inserted into the fluid path to prevent back flow. The concentrate supply lines for can be tied to the current acid and bicarb lines and be configured to empty into the supply water by tying into the system before the filter block. In some embodiments, the pH and chemical content of the incoming water is measured externally, either at installation, or at some interval. Based on the pH and amount of buffering capacity (typically weak alkaline species) in the water, a set flow rate of concentrate can be calculated to mix with the incoming water to adjust the pH to a desired level. This value can then be stored electronically within the system and be used to provide a constant concentrate flow. In some embodiments, the pH or other characteristics of the incoming water may be measured by one, or a plurality of sensors internal to the system. These sensors may be used as an input to a feedback control loop via the electronic controller to adjust the flow of concentrates as required, if incoming water characteristics change. In some embodiments, additional sensors located at a point downstream of the concentrate introduction point can serve as an additional input to the control loop.

Figure 13:
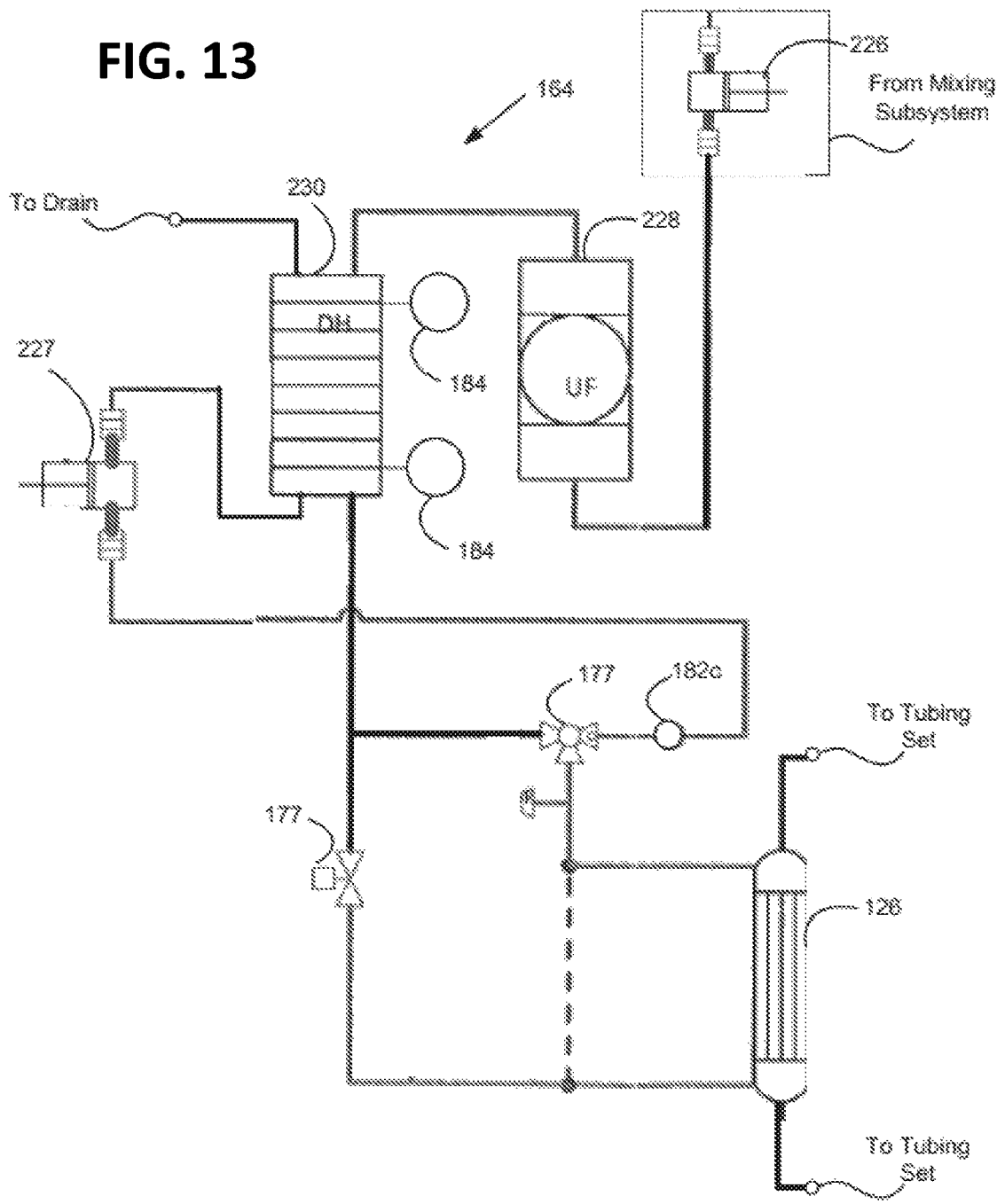
FIG. 13 illustrates an ultrafiltration subsystem of the dialysis delivery system which can receive the prepared dialysate from the mixing subsystem.

FIG. 13 illustrates an ultrafiltration subsystem 164 of the dialysis delivery system which can receive the prepared dialysate from the mixing subsystem. The ultrafiltration subsystem is configured to receive prepared dialysate from the mixing subsystem 162. Dialysate pump 226 and used dialysate pump 227 can be operated to control the flow of dialysate through the ultrafiltration subsystem. The pumps 226 and 227 can control the flow of dialysate to pass through an ultrafilter 228 and a dialysate heater 230 before entering dialyzer 126. Temperature sensors 184 can measure the temperature of the dialysate before and after passing through the dialysate heater 230. The dialysate heater can be user configurable to heat the dialysate based on the user's preference, typically between 35-39 degrees C. After passing through the dialyzer, the used dialysate can flow through a used dialysate pump 230 and back through the dialysate heater 228 before returning to drain. The ultrafiltration subsystem can include one or more actuators or valves 177 that can be controlled to allow dialysate to pass through the dialyzer 126, or alternatively, to prevent dialysate from passing through the dialyzer in a "bypass mode". A pressure sensor 182c disposed between the dialysate pump 226 and the used dialysate pump 227 can be configured to measure a pressure of the dialysate between the pumps when dialysate is prevented from passing through the dialyzer in the "bypass mode".

Figure 14:
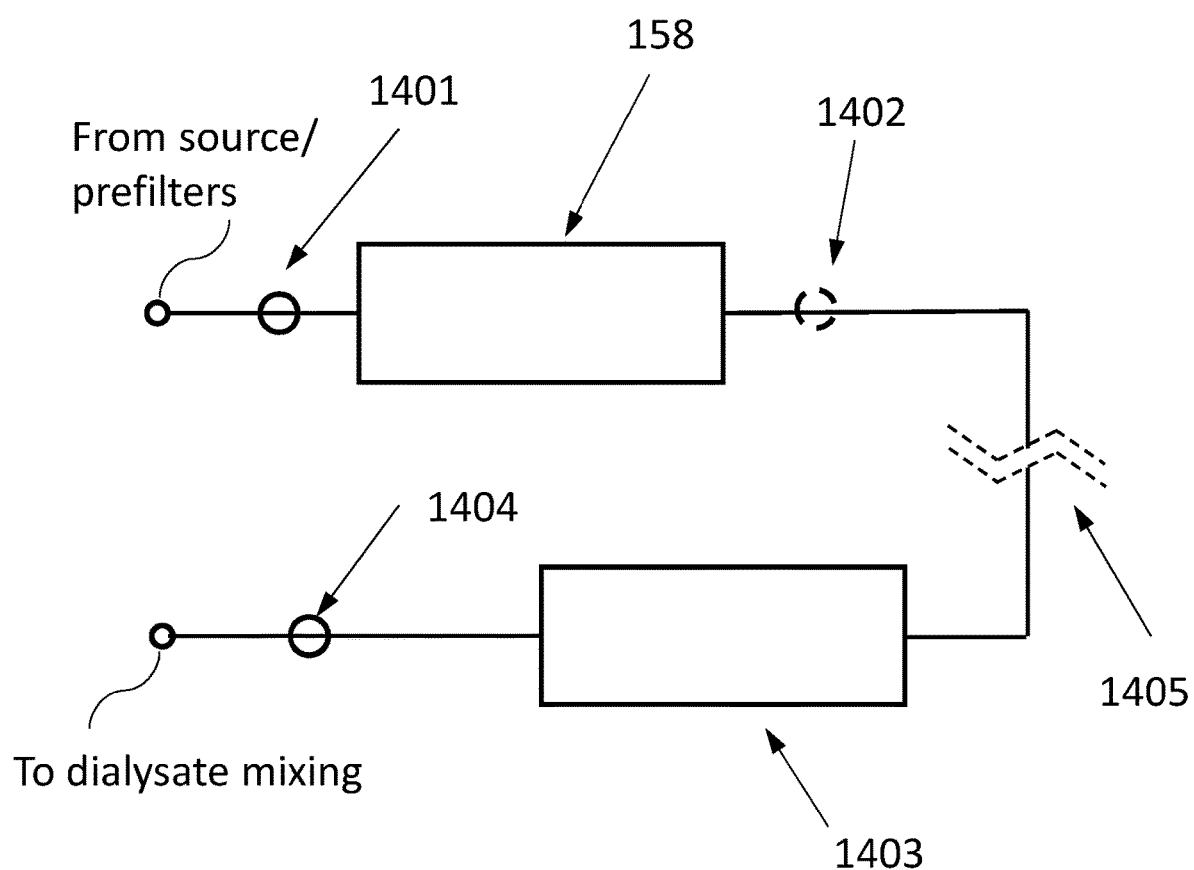
FIG. 14 illustrates an enhancement in measuring the percent rejection in a reverse osmosis system that is integrated into a dialysis machine.

FIG. 14 illustrates an enhancement in measuring the percent rejection in a reverse osmosis system that is integrated into a dialysis machine. Typically, percent rejection is calculated by measuring the conductivity of feed water (ROFC) at position 1401, entering RO filtration subsystem 158 as well as the conductivity of the product water leaving the system (ROPC) at position 1402 immediately following RO filtration subsystem 158, and then establishing a fractional relationship between the two numbers, 1−(ROPC/ROFC). In instances where there are significant amounts of dissolved gases such as ammonia or carbon dioxide in the feed water, these gases are able to pass freely through the reverse osmosis membranes, due to their lack of charge. However, the chemistry of the water changes as it passes through the membrane, and in some cases the pH of the water may shift to a state where dissolved uncharged gas may be kinetically favored to change into an ionic charged species; for example ammonia NH3 to ammonium NH4+. These ionic species, while benign to the patient, will increase the measured product water conductivity, and therefore lower the apparent rejection. In dialysis applications, it is common to flow water through a degassing chamber 1403 prior to mixing with the concentrates. This is accomplished by either heating the water and/or applying a negative pressure to it. In some embodiments, the heating is accomplished by a heat exchanger which simultaneously heats water entering the degas chamber and cools water leaving the degas chamber. If the product water conductivity ROPC is instead measured post-degas at position 1404, the degassing chamber 1403 will remove a large portion of the dissolved gases, and therefore the formation of ionic species will be suppressed. This will provide a more accurate measurement of the performance RO filtration subsystem 158 in rejecting metal salts and other chemicals which are of concern. In conventional dialysis applications, the RO rejection and degassing/dialysate mixing systems are on separate pieces of equipment, as depicted by break point 1405, so this opportunity is not feasible.

The present disclosure further provides for physiological monitoring of absolute blood volume, vascular access status (flow and recirculation) and other parameters with no workflow impact. This is achieved by integration of a single suite of sensors into a hemodialysis system. Mating of the sensor to the blood tubing set is achieved with the singular action that the user performs to mount the cartridge-based blood tubing set to the device. Any actions needed to perform measurements (introduction of indicator, blood flow control, ultrafiltration status) is timed and automated by the device, eliminating the need for user intervention and associated user-based error. Eliminating reliance on trained operators allows these important measurements to better complement care delivery models such as in-home and in-center self-care hemodialysis and drive patient engagement.

In some embodiments, a dialysis system is described that can provide acute and chronic dialysis therapy to users. The system can include a water purification system configured to prepare water for use in dialysis therapy in real-time using available water sources, and a dialysis delivery system configured to prepare the dialysate for dialysis therapy. The dialysis system can include a disposable cartridge and tubing set for connecting to the user during dialysis therapy to retrieve and deliver blood from the user.

Figure 15:
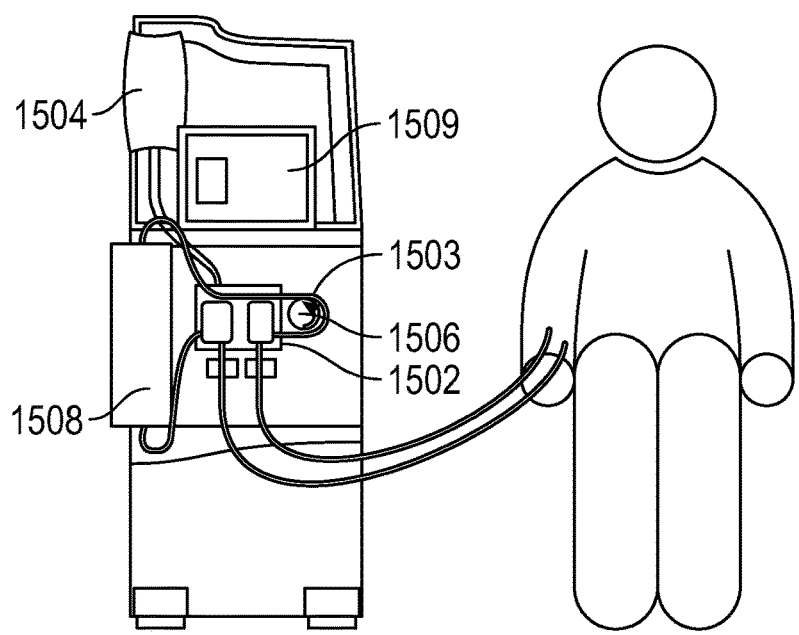
FIG. 15 shows one embodiment of a dialysis system.

FIG. 15 illustrates one embodiment of a dialysis system 1500 configured to provide dialysis treatment to a user in either a clinical or non-clinical setting, such as the user's home. The dialysis system 1500 can comprise a water purification system and a dialysis delivery system disposed within the housing. The water purification system can be configured to purify a water source in real-time for dialysis therapy. For example, the water purification system can be connected to a residential water source (e.g., tap water) and prepare pasteurized water in real-time. The pasteurized water can then be used for dialysis therapy (e.g., with the dialysis delivery system) without the need to heat and cool large batched quantities of water typically associated with water purification methodologies.

Dialysis system 1500 can also include a cartridge 1502 which can be removably coupled to the housing of the system. The cartridge can include a patient tubing set 1503 attached to an organizer, or alternatively comprise a consolidated cassette structure with built-in flow paths attached to a tubing set. The cartridge and tubing set, which can be sterile, disposable, one-time use components, are configured to connect to the dialysis system prior to therapy. This connection correctly aligns corresponding components between the cartridge, tubing set, and dialysis system prior to dialysis therapy. For example, the tubing set is automatically associated with one or more pumps 1506 (e.g., peristaltic pumps), clamps and sensors for drawing and pumping the user's blood through the tubing set when the cartridge is coupled to the dialysis system. The tubing set can also be associated with a saline source 1504 of the dialysis system for automated priming and air removal prior to therapy. In some embodiments, the cartridge and tubing set can be connected to a dialyzer of the dialysis system. In other embodiments, the cartridge and tubing set can include a built-in dialyzer that is pre-attached to the tubing set. A user or patient can interact with the dialysis system via a user interface including a display.

The dialysis delivery system can be configured to automatically prepare dialysate fluid with purified water supplied by the water purification system. Furthermore, the dialysis delivery system can de-aerate the purified water, and proportion and mix in acid and bicarbonate concentrates from dialysate containers. The resulting dialysate fluid can be passed through one or more ultrafilters to ensure the dialysate fluid meets certain regulatory limits for microbial and endotoxin contaminants, as described above.

Dialysis can be performed in the dialysis delivery system of the dialysis system 1500 by passing a user's blood and dialysate through the dialyzer. The dialysis system 1500 can include an electronic controller configured to manage various flow control devices and features for regulating the flow of dialysate and blood to and from the dialyzer in order to achieve different types of dialysis, including hemodialysis, ultrafiltration, and hemodiafiltration.

FIG. 15 shows one example of a front panel of the dialysis delivery system which can include cartridge 1502 and its associated tubing set 1503 to the dialysis system 1500 and to the patient. The dialysis delivery system can be configured for monitoring and controlling fluid flow along the tubing set of the cartridge. The front panel of the dialysis delivery system can include, among other features, a saline source 1504 configured to infuse saline into the tubing set, a blood pump 1506 configured to control the speed and direction of blood flow, and an ultrafiltration system 1508 configured to filter the blood in the tubing set. The dialysis system can further include an electronic controller or computing system 1509 configured to control all aspects of the system before and during treatment, including operation of the blood pump and infusion of saline from the saline source into the tubing set.

Described herein is a hemodialysis system with a custom cartridge-based blood tubing set that is configured to be mounted onto the dialysis machine for treatment. The tubing set itself is configured such that the mounting process is easy to perform, and creates interfaces between the tubing set and the dialysis system, including with the blood pump, pinch valves, and sensors. In one example, the dialysis system can include one or more transit-time ultrasound probes, one that is mated to the venous line, and the other that is mated to the arterial line. The sensors can alternatively comprise, for example, doppler shift sensors.

Figure 16:
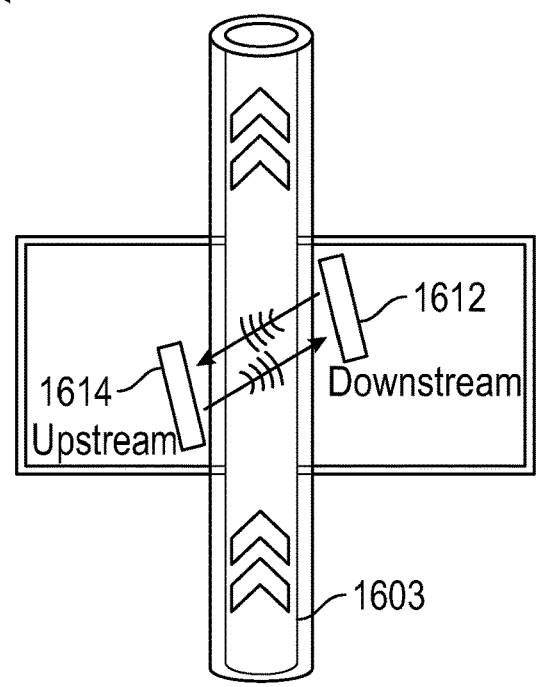
FIG. 16 illustrates an embodiment of a transit-time ultrasound probe.

FIG. 16 illustrates a transit-time ultrasound probe 1610 according to the present disclosure. Each transit-time ultrasound probe can include a plurality of ultrasound transducers 1612 and 1614 which are configured to propagate ultrasound energy into a flow vessel, in this case the blood or patient tubing set 1603 described above. One of the transducers 1614 can be positioned upstream of the flow direction, and the other transducer 1612 can be positioned downstream of the flow direction as indicated by the arrows within the patient tubing set. Each transducer can be configured to both transmit and receive an ultrasound signal. When the upstream transducer transmits, the speed of propagation through the tubing will be increased by the flow velocity of the tubing. Conversely, when the downstream transducer transmits, the speed of propagation through the tubing will be reduced. Regardless of which transducer transmits, the propagation speed is also affected by composition of the media, e.g., the relative water content of the blood, air bubbles and/or gas in the blood, etc. The transit time of both the upstream and downstream ultrasound pulses can be measured and processed by the electronic controller of the dialysis system. In one embodiment, the electronic controller can be configured to summate the signals, causing the flow velocity component to disappear, which therefore allows the electronic controller to infer the fluid composition component of the fluid within the tubing set. In another embodiment, the electronic controller can be configured to subtract the two signals, causing the fluid composition component to disappear, which allows the electronic controller to measure the flow velocity of the fluid within the tubing set.

The novel approach described herein integrates the ultrasound sensors onto a hemodialysis machine, allowing full automation of the ancillary tasks needed to take measurements and adding the capability of measurements continuously throughout the course of treatment.

Much of the transit-time ultrasound probe's potential, as described herein, is unlocked by providing seamless integration into a dialysis system, which includes the extracorporeal blood tubing set, or circuit (cartridge) which routes the patient's blood to and from his or her body. At a minimum, this cartridge can comprise an arterial blood line blood line blood from the patient) and a venous blood line (carrying blood back to the patient). The cartridge can further comprise a section of tubing (preferably integrated into the arterial line) that interfaces with a non-contact blood pump. The distal end of the arterial line connects into one end of a blood filter, such a dialyzer, while the distal end of the venous line connects to the other end of the filter. Fluid removal from the blood will occur through the blood filter, along with solute clearance.

Preferably, the dialysis machine, when the cartridge is attached, will comprise features (such as mechanical, electrical, hydraulic, or pneumatic pinch valves) to independently occlude the arterial and venous lines for safety and flow control. The cartridge can also comprise at least one fluid source for introducing saline, or other fluid suitable to serve as a dilution bolus. In some embodiments, a saline bag is connected to the arterial line in two places via two lines; one immediately upstream of, and one immediately downstream of the blood pump segment. These two saline lines may be independently occluded, for example by mechanisms similar to those that occlude the venous and arterial lines. During treatment when no saline is being delivered, both saline lines can be occluded. To introduce saline during antegrade flow, the arterial line can be occluded, and the pre-pump saline line can be unoccluded, which effectively changes the inflow of the blood pump from the patient to the saline bag. After the desired volume is introduced, the occlusion states can return to their previous states. Alternatively, to achieve mixing of the saline with the blood, the pre-pump saline line may be unoccluded while not occluding the arterial line. To introduce saline during retrograde flow, the venous line can be occluded, and the post-pump saline line is unoccluded. Analogous to the antegrade case, mixing can be achieved by unoccluding the post-pump saline line while leaving the venous line unoccluded as well.

The volume status of the patient (either as determined by blood volume monitoring, impedance, or simple weight measurement) serves as an input to the mechanical function of ultrafiltration, or fluid removal, for the dialysis treatment. The transit-time ultrasound probes of the present disclosure provide a robust, intelligent linkage to allow sensor input to adjust ultrafiltration rate. The requirements of ultrafiltration accuracy are very high. For example, over the course of a 4-hour treatment at a 400 mL/min blood flow rate, 96 liters of blood in total will have passed through the circuit. The treatment goal might be to remove 2 liters of fluid from the patient, and an allowable error tolerance on that fluid volume might amount to ±250 mL, a figure equivalent to 1 mL/min, or 0.25% of the blood flow rate. Such accuracy is generally not possible with a single flow probe.

Figure 17:
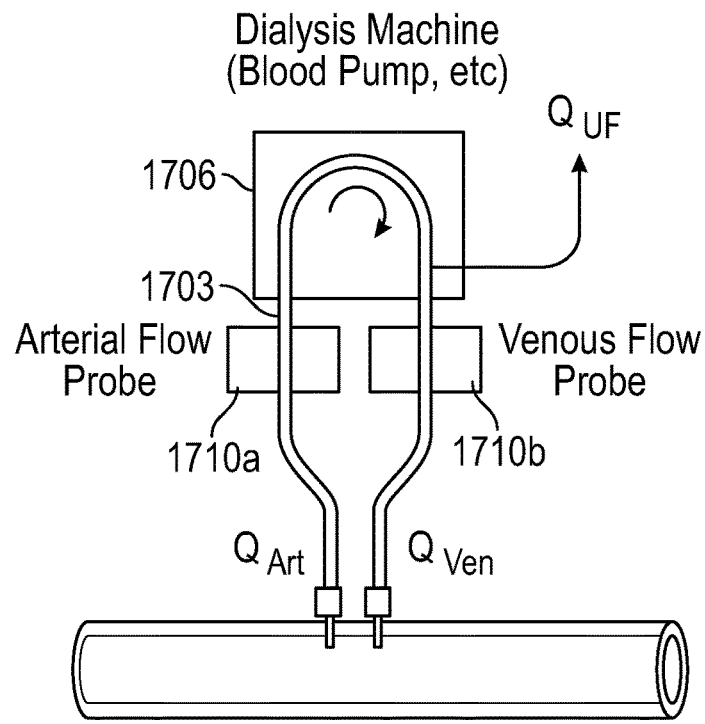
FIG. 17 is a schematic diagram illustrating a technique of determining an ultrafiltration rate with a pair of transit-time ultrasound probes.

FIG. 17 illustrates a schematic diagram of a technique for performing ultrafiltration monitoring with the transit-time ultrasound probe of FIG. 16. FIG. 17 shows a tubing set 1703 mounted to a dialysis system including a blood pump 1706, with a pair of transit-time ultrasound probes 1710a and 1710b positioned on the arterial line and venous line, respectively. The arterial probe 1710a, measuring $Q_{art}$, is positioned upstream of the dialyzer where $Q_{UF}$ from the blood will occur, while the venous probe 1710b measuring $Q_{ven}$ is downstream of the dialyzer. The relationship between these terms may be simply expressed as $Q_{art} = Q_{ven} + Q_{UF}$.

Also, when the blood volume is measured, the fluid removal rate can be adjusted based on these measurements. Operationally, at the beginning of treatment, an injection bolus can be infused into the patient, the volume of which can be monitored with the flow sensors, and physiological parameters such as active circulating blood volume is measured. Subsequently, a fluid removal rate can be established by the dialysis system that takes into account at least some of these factors: A) Initial volume of priming fluid in the patient tubing set that is infused into the patient, B) Volume of injection bolus needed to perform physiological measurement (A & B may be the same) and C) Result of physiological blood volume measurement.

Then, periodically throughout treatment, a regimen for regularly timed injection boluses can be provided. These can serve up to three purposes: 1) Flushing of the blood circuit to reduce clotting; 2) Loading additional fluid into the blood circulation, in order to enable subsequent higher fluid removal rates, driving improved convective clearance (push-pull hemodiafiltration), and 3. Allowing for physiological measurements. After each of these periodic boluses, the new fluid removal rate can be adjusted based on volume of injected bolus, and result of physiological blood volume measurement. Because the injection bolus, just by its nature, increases the overall blood volume, the fluid removal rate can be set higher, which increases convective transport of solutes across the dialyzer, thereby fulfilling the objective of purpose 2 above. In some embodiments, the source of injection bolus may come from filtered dialysate, which can be added to the blood circuit by running a used dialysate pump slower than a new dialysate pump for a period of time. This can cause the excess dialysate flow to cross into the blood side of the dialyzer, effectively the opposite of what happens during normal ultrafiltration. Alternatively, injection boluses may be supplied from a sterile saline bag attached to the blood circuit, whose flow can be controlled by the pinch valves.

Accuracy of the probes can be further enhanced by characterizing sensor response curves at time of manufacturing, and installing sensors with matching response curves on each machine. If necessary, a recalibration event can occur periodically during treatment, where ultrafiltration is stopped for a time and blood flow balance is reestablished.

The transit-time ultrasound probes can also be used in a dialysis system for vascular access surveillance. Vascular access dysfunction is a leading cause of missed treatments. There are a number of methods to perform surveillance and provide early warning if a patient's vascular access shows signs of stenosis. The ideal surveillance method would provide high quality data, allow for frequent measurements (ideally every treatment) and minimize burden of care staff. The approach described herein allows vascular access surveillance using saline dilution to be completely automated. Briefly, there are two parameters which can be measured by the transit-time ultrasound probes; 1) access recirculation (the percentage of processed blood from the machine that is subject to re-uptake, reducing treatment efficiency), and 2) volumetric access flow through a vascular access shunt (either a fistula or a graft).

Figure 18A:
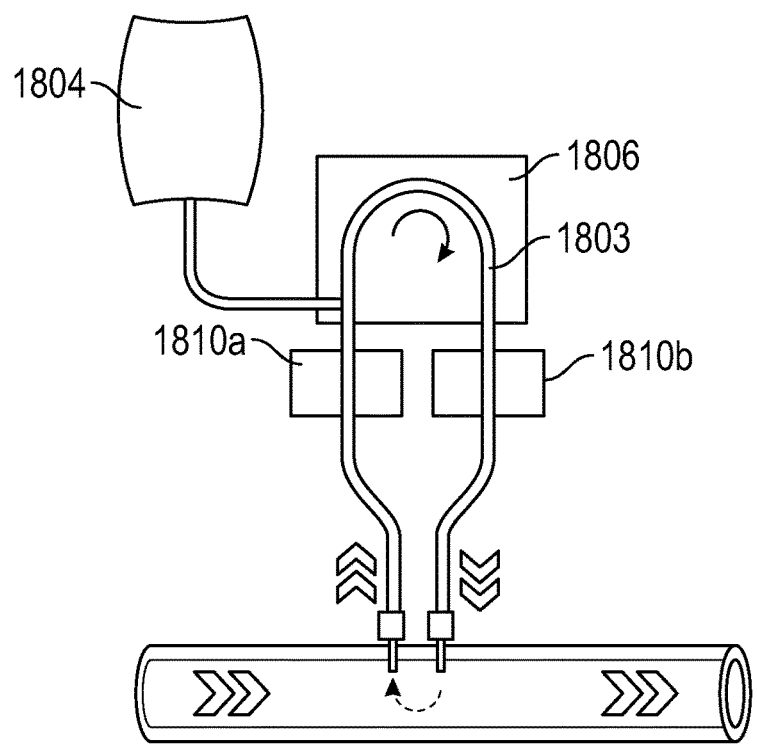
FIGS. 18A-18B are schematic diagrams of techniques for monitoring a patient's vascular access site.
Figure 18B:
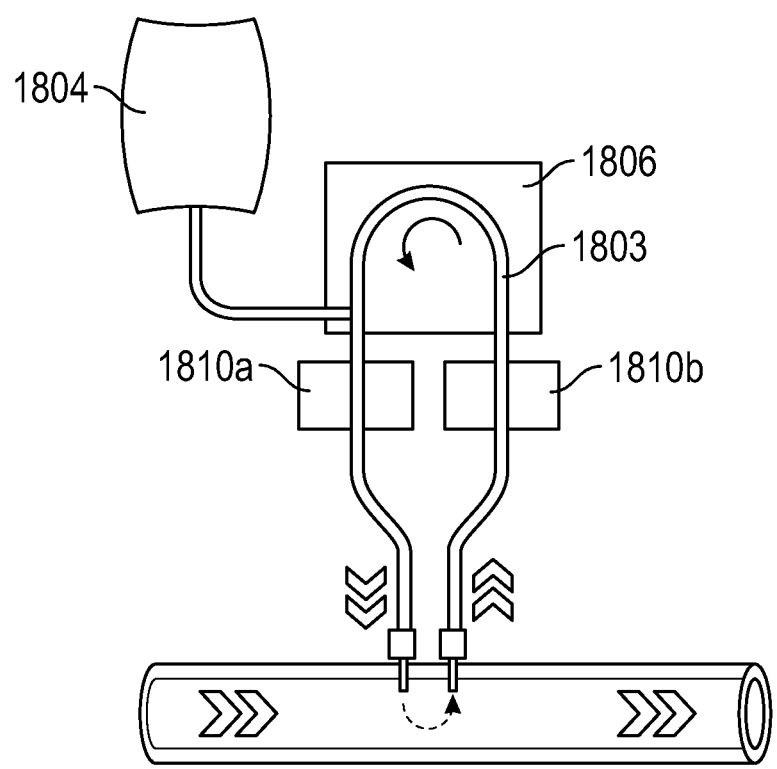

FIGS. 18A-18B illustrate a technique for using transit-time ultrasound probes for vascular access surveillance. The dialysis system illustrated in FIGS. 18A-18B can include a blood tubing set 1803, saline source 1804, a blood pump 1806, and transit-time ultrasound probes 1810a and 1810b on the arterial and venous flow lines, respectively. To measure recirculation, a small bolus of saline (dilution indicator) can be introduced from the saline source 1804 into the blood tubing set 1803. This causes a change in fluid composition, which can then be detected by the venous probe 1810b to establish a baseline dilution curve. The dilution indicator then exits the blood tubing set and enters the patient's vascular access via the venous needle. If any recirculation is present, a proportional amount of dilution indicator will be taken up by the arterial needle and detected by the arterial probe 1810a. The flow direction through the tubing set in this technique is shown with the arrows.

Even a miniscule amount of recirculation is indicative of an access with potentially critically-low flow, so the complete automation of this function performed every session, or even multiple times within a session, allows for detection much sooner than possible with current methods. Specifically, the method can include connecting arterial and venous lines of a blood tubing set to a patients vascular access site, introducing a bolus of saline into the blood tubing set, determining a baseline dilution curve of the patient's blood and the bolus with a transit-time ultrasound probe on the venous line of the blood tubing set, and, if a proportional amount of the bolus is detected with a transit-time ultrasound probe on the arterial line of the blood tubing set, determining that recirculation is present.

Conceptually, measurement of access flow is very similar, as illustrated and described in FIG. 18B. The same process described above repeats, except that blood is withdrawn from the venous needle and re-introduced by the arterial needle. If flow through the access is very high, then the vast majority of the indicator dilution will be carried past the venous needle in a very low concentration causing the venous probe to detect very little. Conversely, if the access flow is relatively low, a higher concentration of the saline dilution indicator will enter the venous needle and be detected by the venous probe. In the proposed technique, flow reversal is accomplished by causing the machine to reverse the direction of the blood flow. The flow direction through the tubing set in this technique is shown with the arrows. The design of the cartridge blood set may be amenable to this ability, featuring, for example, the ability detect air and small clots on the arterial line and prevent them from reaching the patient. Specifically, the method can include connecting arterial and venous lines of a blood tubing set to a patients vascular access site, reversing a flow direction of fluid within the tubing set, introducing a bolus of saline into the blood tubing set, determining a baseline dilution curve of the patient's blood and the bolus with a transit-time ultrasound probe on the arterial line of the blood tubing set, determining an access dilution curve with a transit-time ultrasound probe on the venous line of the blood tubing, and comparing the baseline dilution curve to the access dilution curve to determine a measurement of access flow.

The transit-time ultrasound probes can also be used in a dialysis system for blood volume monitoring. One of the key objectives of any renal replacement therapy is removal of excess fluid from the patient. In hemodialysis, this fluid comes from the patient's circulation, and, in theory, fluid lost from the circulation is replenished from the patient's fluid overloaded tissues. A large proportion of patients undergoing hemodialysis treatments exhibit hypotensive symptoms due to excessive depletion of blood volume. Aside from the immediate symptoms, depletion of fluid volume during dialysis and subsequent overload during the intradialytic period has been linked with long-term cardiac and cerebral tissue impairment, as well as increases in morbidity and mortality. The traditional method to establish this fluid removal target has been subtracting the patient's pre-dialysis weight from a "dry weight" of the patient. This approach is often imprecise and does not take into account other factors (feces, distribution of fluid, clothing differences) that impact weight unrelated to accessible excess fluid volume. Some current hemodialysis machines are equipped with sensors that detect the hematocrit or total blood protein concentration in an attempt to address these confounders. As fluid is removed, the blood becomes more concentrated, from which it is possible to infer the relative change in blood volume. Drawbacks to this technique include inability to establish an actual baseline blood volume and sensitivity to factors that impact blood concentration (such as erythrocyte release) unrelated to volume change. It has been suggested that measuring the patient's absolute blood volume rather than the relative change in blood volume could be a clinically valuable metric in establishing or altering fluid removal parameters. Several methods have been proposed, including radioisotope labeling, blood dilution and UF shifting. In practice however, there has yet to be a method established to measure absolute blood volume during every hemodialysis treatment session that is cost- or workflow-effective.

Blood volume measurements (absolute and relative) can be performed with the same two transit-time ultrasound probes described above. As stated earlier, the flow probes can detect changes in flow media composition, which is how they are able to pick up the saline dilution indicator. Simplistically, as treatment progresses and fluid is removed from blood, it becomes more concentrated, subject to effects such as vascular refilling. The probes can be configured to detect change, which can be correlated with relative blood volume.

Figure 19:
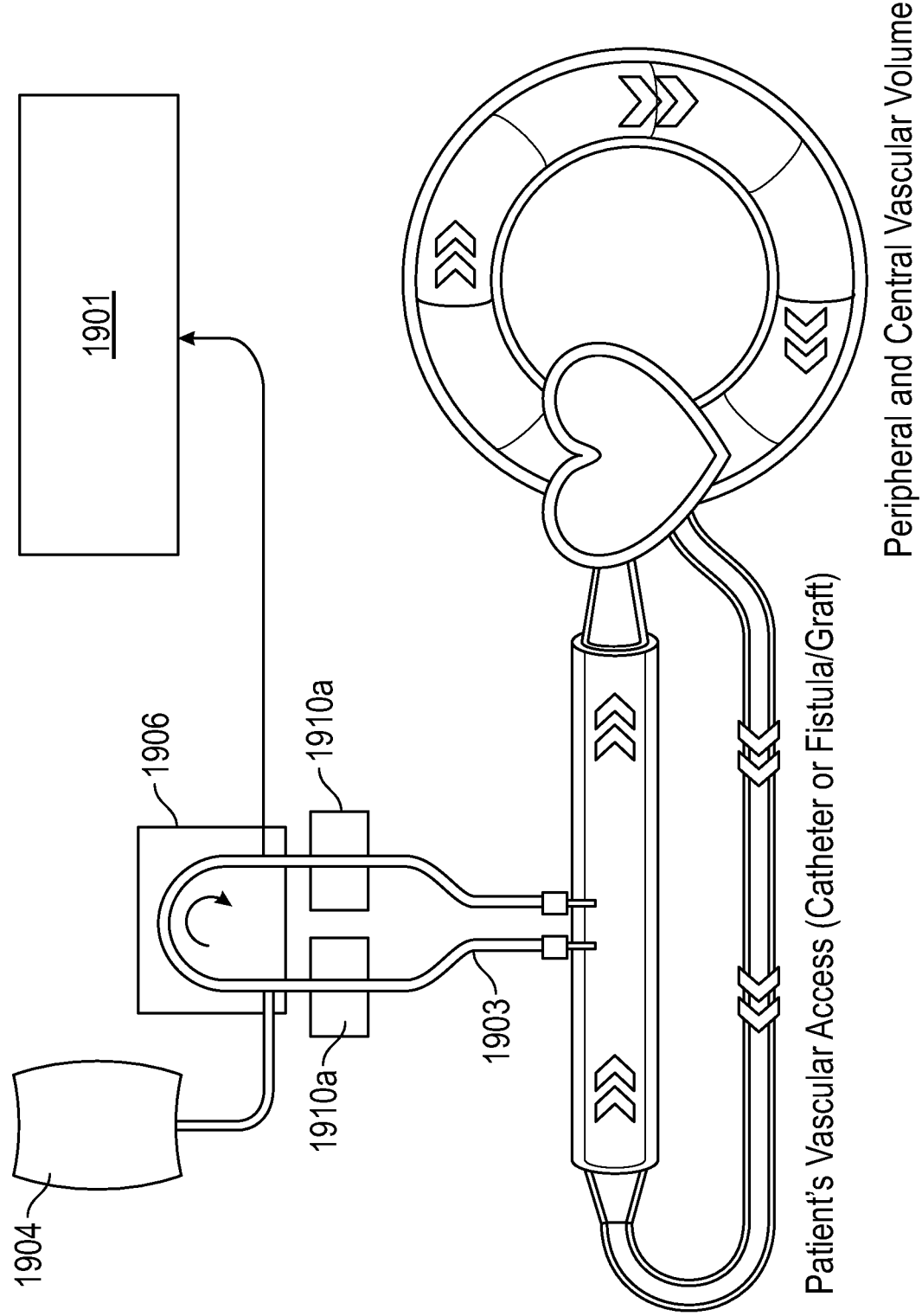
FIG. 19 is a schematic diagram illustrating a technique of determining a patient's blood volume.

FIG. 19 illustrates a system and method for measuring absolute blood volume during dialysis therapy, and can include the system components described above, including an electronic controller 1901, blood tubing set 1903, saline source 1904, a blood pump 1906, and transit-time ultrasound probes 1910a and 1910b on the arterial and venous flow lines, respectively. Referring to FIG. 19, absolute blood volume can be measured using the following automated technique: While the circuit is in normal flow, a relatively large (60-100 mL) dilution bolus of saline is introduced from the saline source 1904 over the course of several seconds. The bolus can be released, for example, via the controller actuating valves to allow saline to flow from the saline source into the blood tubing set. The transit-time ultrasound probe 1910b on the venous line can determine a baseline dilution curve of the patient's blood and the bolus (e.g., determining the water content of the blood). The dilution bolus will then enter the patient's bloodstream and move into the heart and lungs where it is homogenously mixed.

From there, it is distributed to the remainder of the circulation, a portion of which, along with the patient's blood, will return to the blood tubing set with each heartbeat. After a desired measurement window, this remaining portion of the dilution bolus can then be detected by the transit-time ultrasound probe 1910a on the arterial line, and the distribution volume of the blood can then be inferred from the time course of that signal.

It may seem counterproductive to infuse fluid when the goal of therapy is to remove excess fluid. However, the infused fluid may improve hemodynamic stability and provide information as to whether any instability encountered is due to volume depletion or vascular tone. This information can be used, for example, to personalize treatment profiles for particular patients or patient populations. Once the desired measurement window has elapsed (a dilution bolus has a half-life of approximately 10-15 minutes), the ultrafiltration rate of the system may be increased to gradually remove the infused volume. As a synergistic benefit, periodic infusion of saline boluses has also been shown to be beneficial in reducing clotting in the extracorporeal circuit and reducing anticoagulation use. These can be used as opportunities to acquire absolute blood volume measurements. With the increased ultrafiltration rate to remove the volume introduced by the bolus, solute clearance may also improve by increased convection.

In accordance with the current disclosure, several novel features of this cartridge are described herein. In traditional hemodialysis therapy, it is common practice to monitor the extracorporeal pressure in the venous and arterial lines. Large fluctuations in pressure could be indicative of events such as kinked tubing or acute vascular access dysfunction, which either prevent the flow of blood and/or cause flow conditions that mechanically damage the blood (hemolysis). Extracorporeal pressures are influenced by the state of the patient's vascular access, length of tubing used and needle size. It is known in the art to use a non-contact mode of pumping blood to minimize machine contamination, such as a peristaltic roller pump, which rotates at a given rotational speed. Alternatively, a linear non-contact peristaltic pump may be used.

Delivering consistent blood flow rate is an important clinical consideration in delivering hemodialysis therapy. For a given blood pump speed, a lower (more negative) arterial pressure will result in a lower blood flow rate. It is also known that over the course of several hours of a hemodialysis treatment, the temperature of the pumped blood and mechanical wear of the tubing section within the peristaltic roller will cause the flow rate to decrease for a constant rotational speed. This can be expressed in the following generalized equation:

$$Q_b = f(C_1 P_{art}, C_2 t, V_{pump})$$

where $Q_b$ is the actual blood flow rate, $P_{art}$ is the arterial pressure, t is the time in treatment, $V_{pump}$ is the rotational speed of the pump, $C_1$ and $C_2$ are generalized weighting constants and f( ) is a linear, exponential or other mathematical equation known in the art. In the idealized blood pump, $C_1$ and $C_2$ would be zero, and therefore the same blood flow rate is generated by the pump under all conditions for a given rotational speed. In practice, it is often a design goal of a blood pump system to achieve a values of $C_1$ and $C_2$ as close to zero as possible, thereby minimizing the variation of flow rate due to time and arterial pressure. This can be achieved by material selection of the tubing, dimensions of the tubing, roller geometry and number of rollers. The rationale behind selecting designs which minimize $C_1$ and $C_2$ are that in the prior art, blood flow rate is generally not known. Arterial pressure is generally known, due to transducers and sensors built into the blood tubing set and hemodialysis machine. Since arterial pressure is known, along with time in treatment, it is known in the art to use these factors to apply a correction factor to blood pump speed and maintain an actual blood flow rate close to the target.

Non-contact means of measuring extracorporeal pressure within the blood tubing set are well known in the art. One such method comprises maintaining an air gap over a specialized chamber, and measuring the pressure of the air within the gap. Another method comprises a flexible diaphragm in contact with the blood which is able to transmit pressure to a sensor on the other side, either via a sealed pneumatic chamber or through force transduction. These methods involve specialized chambers within the blood tubing set which add cost to both the blood set itself, as well as to the hemodialysis machine itself. They are also prone to introduce inconsistencies in the blood flow path, increased blood contact surface area and/or contact between the blood and air, which may promote thrombogenic pathways and lead to clotting of the blood tubing set or dialyzer.

In the present disclosure, since $Q_b$ is a measured quantity, it enables a novel method of algorithmically determining the arterial pressure, without the need for additional flow chambers or hardware. At a high level, the equation may be re-arranged algebraically to change $P_{art}$ from a known value to the value being solved for, and $Q_b$ from the value being solved for to a known value:

$$P_{art} = f(C_3 Q_b, C_2 t, V_{pump})$$

Figure 20:
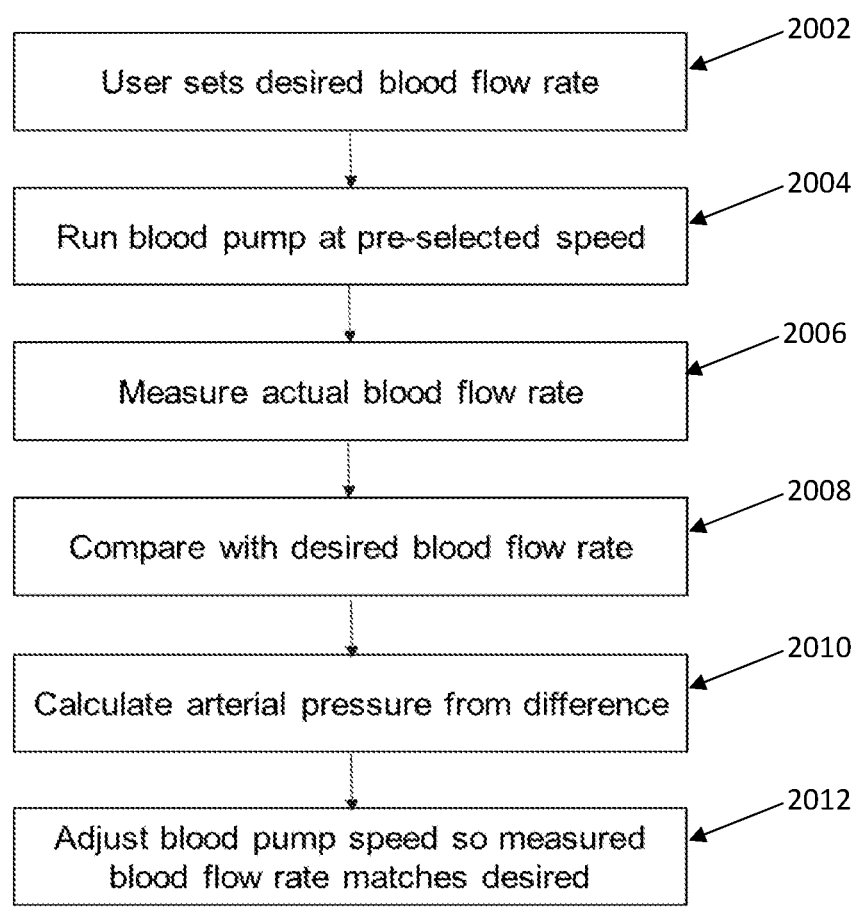
FIG. 20 is a flowchart for determining an arterial pressure in a dialysis patient.

From a design perspective, a blood pump system with a higher dependence on the arterial pressure (larger $C_1$ or equivalently larger $C_3$) would be better suited to this invention, contrary to the ideal pump in the prior art. FIG. 20 is a flowchart describing a method of calculating the arterial pressure during dialysis treatment. In operation, at step 2002, the user and/or electronic controller sets the desired blood flow rate. At step 2004, the controller will set the blood pump speed to a nominal value that will achieve a blood flow rate close to the set rate, at an assumed arterial pressure. Throughout this process, at step 2006, the blood flow rate is monitored via flow sensors disposed within the dialysis system. At step 2008, the measured flow rate is compared to the desired flow rate, and the difference between the measured blood flow rate and desired blood flow rate will be due to the arterial pressure and/or other factors which can be measured or accounted for, such as time into treatment. From this difference, at step 2010, the controller is able to algorithmically infer the arterial pressure, and display it for the user. Finally, at step 2012, the controller can make an adjustment to the blood pump speed to match the actual blood flow rate to the desired blood flow rate. Assuming that the blood pump speed is maintained constant, any fluctuation in the measured blood flow rate would be indicative of a change in the arterial pressure, which can lead to an update to the measured and displayed value. The controller can adjust the blood pump speed (within given parameters) to compensate and maintain the desired blood flow rate through, for example a PID control scheme.

While it could be theoretically possible to derive the extracorporeal pressure downstream of the blood pump (i.e., venous pressure) by a similar method, in practice the equation becomes underconstrained. Therefore the preferred embodiment comprises other techniques for measuring the venous pressure. In the current art, it is known to have a flow chamber where there is a layer of air above a layer of blood. The flow of blood may enter from the top of the chamber, dripping down onto the surface, or from the bottom. Typically the blood flow leaves from an aperture connecting to a tubing at the bottom of the chamber. In the case of a top-entry chamber, any air that is part of the incoming flow is separated as the blood flow contacts the air as a downward stream or as droplets. In the case of a bottom-entry chamber, a vertical septum is positioned between the entry and exit apertures, such that the flow must rise over the septum before proceeding to exit. The buoyancy of any air that is part of the entrapped air will cause it to continue rising after the bulk flow has crested the septum, separating it. The presence of the air layer also enables measurement of the pressure within the chamber without the pressure sensor needing to touch the blood, since the pressure of the air layer will equal the pressure of the blood below it, minus any minor compliance factors. To protect the machine from contamination in the case that the blood level rises uncontrollably, typically a hydrophobic filter, or transducer protector, is placed in the line leading from the flow chamber to the pressure measurement hardware. When it is not wetted and exposed to only air, it allows free passage of air and transduction of pressure. Should the blood level rise, the transducer protector will be wetted and the hydrophobic membrane will seal off, preventing blood from rising any further. While this is an important feature that mitigates contamination risk, when the transducer protector is wetted, the ability of the pressure sensor to detect pressure disappears. Therefore, in these configurations, the maintenance of the blood level within the flow chamber is of paramount importance. This can be done manually, by periodically inspecting the level within the chamber visually, and then performing a manual aspiration or injection of air with a syringe to correct the level. However this requires attention of staff or other uses.

This monitoring and adjustment can also be done via sensors and actuators; for example an ultrasonic, optical or other sensor automatically monitors the blood level within the chamber, and in response to the level exceeding predetermined limits, an air pump integrated into the machine and connected to the flow chamber can be used to aspirate or inject air to correct the level. This adds cost and complexity to the system and is dependent on the reliability of the level sensor and pump.

Prior to beginning treatment, it is necessary to fill the extracorporeal circuit with priming fluid, typically saline or dialysate, and remove all of the air from within the interior volumes. In the preferred embodiment of the invention, during priming the arterial and venous lines are connected together to form a continuous loop, and therefore it is necessary to provide for a point of escape for the air somewhere in the fluid path. Furthermore, after treatment has commenced, there are instances when air may be introduced into the fluid path. This can happen when the arterial needle becomes temporarily dislodged, or a very low arterial pressure is generated transiently, causing dissolved gas in the blood to be pulled out of solution and form an air bubble. Since it is undesirable due to risk of air embolism to introduce this air into the patient via the venous flow, there exists a need to remove this air from the blood flow before it reaches the patient, or at the very least entrap it and prevent it from flowing to the patient.

Another aspect of the disclosure is a flow chamber with different embedded membranes that provide for these three needs—measurement of pressure, removal of large amounts of air during priming, and removal or entrapment of smaller amounts of air during treatment. FIGS. 21A-21D illustrate a flow chamber integral to the flow path of the extracorporeal cartridge, preferably positioned immediately downstream of the dialyzer, although other positions are possible. The flow enters from the bottom of the chamber, crests a vertical septum 1201, and exits from a different outflow aperture on the bottom of the chamber.

Figures 21C, 21D:
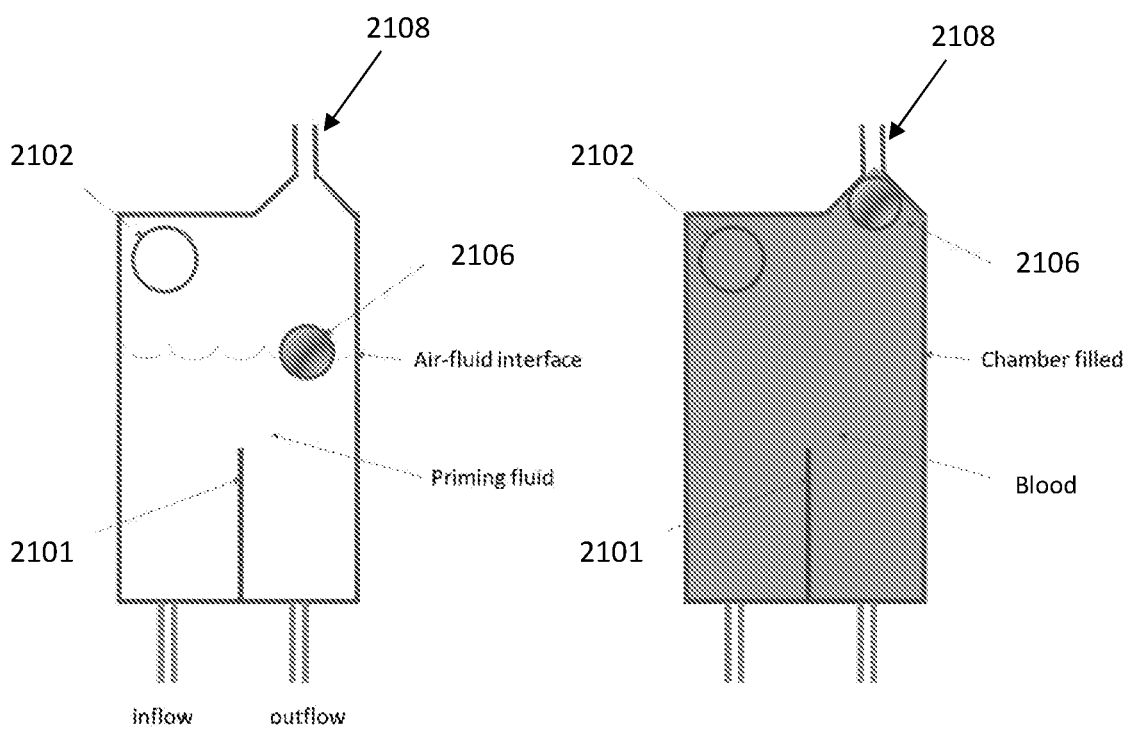

The flow chambers illustrated in FIGS. 21A-21D comprise a flexible elastomeric diaphragm 2102, through which pressure is transduced and sensed. This diaphragm does not permit liquid flow nor significant gas flow through it. Therefore, a separate mechanism is provided to evacuate the air during the pre-treatment priming. This mechanism may comprise a hydrophobic filter membrane 2104 integral to the chamber, but separate from the flexible elastomeric membrane 2102 (as shown in FIGS. 21A-21B), or alternatively, a float ball valve 2106 at the top of the chamber (as shown in FIGS. 21C-21D). In either embodiment, the intent during priming is to maintain a layer of air between the priming fluid and the top of the chamber. Thus, during priming, air would be able to escape through either the hydrophobic membrane, or ball valve mechanism. The evacuation of air could be driven by either internal pressure within the chamber and circuit, a negative pressure applied to the chamber by a pump, or a combination of both. After priming is complete, the residual air layer is then completely evacuated out. The hydrophobic membrane would be wetted (in the embodiment of FIGS. 21A-21B), or the float ball valve would seal an upper outlet 2108 (in the embodiment of FIGS. 21C-21D). Treatment is then run with the chamber completely full, without an air-blood interface layer. The ability to sense pressure is no longer integrally coupled with the need to maintain a level of an air-blood interface within the flow chamber.

If the flexible elastomeric diaphragm 2102 is fluidically coupled to a sealed chamber on the non-blood side to detect pressure, pressure on both sides equalizes. In this case, a third mechanism, such as a degassing membrane 2110, may be incorporated into the flow chamber of FIGS. 21A-21B. This can be a highly gas-permeable, thin membrane, such as a membrane comprising polydimethysiloxane, with a blood facing side, and an atmospheric-facing side. Since the pressure in the flow chamber is generally positive, air bubbles will kinetically diffuse towards the lower pressure atmosphere through this degassing membrane, and be removed from the flow path. If the flexible elastomer diaphragm used to measure pressure is not fluidically coupled to a sealed chamber, and instead uses a means of force-based transduction to measure pressure, then it can also serve as the degassing membrane. Because there is no fluidic seal, there will be the desired pressure gradient across the membrane. Force transduction would work as follows: a force sensor can be positioned on the non-blood contact side of the diaphragm. A greater pressure on the blood side of the diaphragm would cause the diaphragm to distend further, and exert more force, which is detected by the force sensor. Negative pressure can be measured by applying a pre-load to the diaphragm, essentially having the force sensor distend it inward.

A cartridge with these features is uniquely suited to enable the automated measurement features of the sensors described herein. For example, flow reversal with the patient connected is conceptually easy to grasp. However, it is not typically used in dialysis treatment for several reasons: First, most dialysis machines have an air detector on the venous line, but not on the arterial line. Therefore, there is air embolism protection on the antegrade flow direction, but not in the retrograde flow direction. Another feature of the flow probes is that they are able to detect air, and therefore since the proposed embodiment has a flow probe on both the venous and arterial lines, retrograde air embolism protection is inherently provided. Another reason is the potential risk of small thrombi that form within the extracorporeal circuit being dislodged during flow reversal and carried back toward the patient. This is of special concern if there is a flow discontinuity in the fluid path, particularly upstream of the dialyzer (relative to antegrade flow) to support features to measure arterial pressure, such as a pressure pod which is known in the art. In the described invention, no such flow discontinuity exists, as the flow probe can be used to determine arterial pressure without the need for such hardware. This risk can be further mitigated by directing flow reversal measurements to be performed during the first few minutes that a patient is connected, where the likelihood that a significant, dislodgeable thrombus has formed is low. If a thrombus were present in the flow chamber described, and somehow were to be dislodged during retrograde flow, it would flow into the dialyzer and not be able to pass its small, hollow fibers.

Figure 22A:
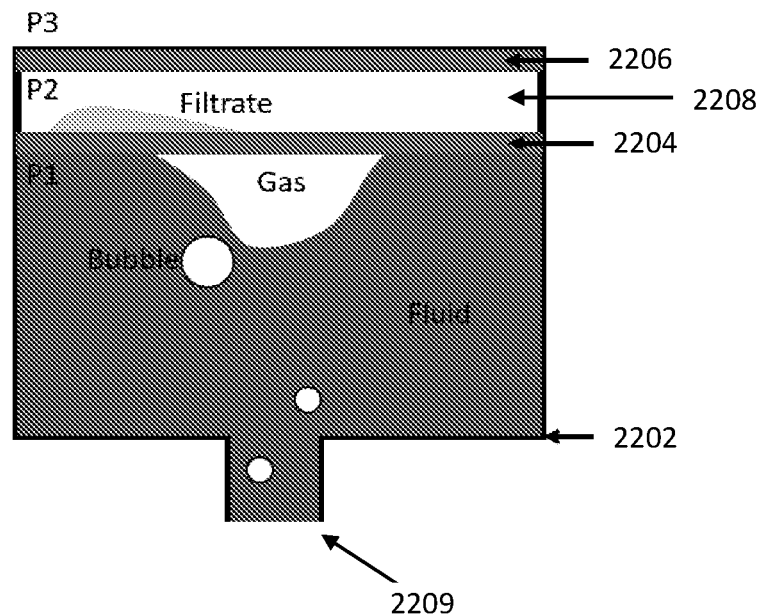
FIGS. 22A-22B illustrate one embodiment of a flow chamber for a dialysis system.
Figure 22B:
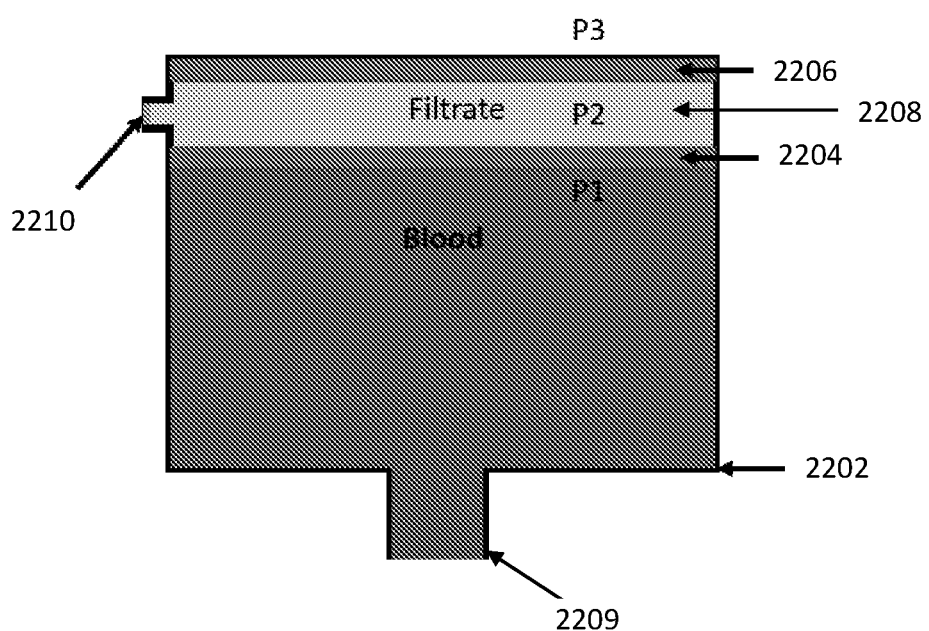

Alternative designs of air removal chambers or drip chambers are also provided herein. During the normal course of both dialysis treatment and dialysis circuit priming the need to remove air while retaining the fluid bulk is desired. In one embodiment, as shown in FIGS. 22A-22B, an air removal chamber 2202 comprises a primary chamber configured to be filled with fluid such as saline or blood, and further includes a primary membrane 2204 and a secondary membrane 2206, separated by a secondary chamber 2208. The air removal chamber can include at least one inlet/outlet 2209 to allow blood/fluid to enter and exit the chamber. In this example, the membranes are positioned perpendicular to the general plane of flow paths through the chamber. Although a single inlet/outlet 2209 is illustrated in FIGS. 22A-22B, it should be understood that separate (i.e., two or more) inlet/outlets can be implemented. A multi-filter/membrane approach is utilized in this embodiment. Each membrane creates a pressure drop across the filter path and thus the driving pressure subsequently decreases for each filter. While the primary membrane is designed to prevent blood from passing, during the course of dialysis treatment, small amounts of filtrate and/or blood plasma can pass through the membrane and collect in the secondary chamber 2208. If enough filtrate or blood plasma is collected within the secondary chamber as to completely fill it, in some embodiments the design can include a third chamber as a backup.

To achieve a selective permeability that allows air and gas but not blood to pass, a material with sufficiently small porosity to retain cellular material but allow the free passage of air and a sufficiently low surface energy to repel blood plasma is required. Such a membrane can be employed on the air removal chamber 2202 to maintain an airless blood cartridge as well as facilitate cartridge priming by the efficient removal of air. The multi-stack approach illustrated in FIGS. 22A-22B further improves the usable life of the cartridge.

While the dynamic viscosities of air and blood are vastly different, they are both still fluids and thus subject to the same laws. A sufficiently small porosity and low filter surface energy will lend itself to resist blood flow, it will not stop it. With sufficient time and/or pressure, blood plasma will perfuse through the filter as a rate that is a function of the mechanisms involved. The multi stack filter configuration of FIGS. 22A-22B includes a secondary membrane 2206 to prevent contamination and a secondary chamber 2208 to contain any unwanted blood plasma. In some embodiments, the size/volume of the secondary chamber is chosen based on the volume of blood plasma that passes through the primary membrane during a typical dialysis treatment.

In the embodiment of FIG. 22B, the secondary chamber 2208 can include a tap 2210 to allow for blood plasma sampling/harvesting during dialysis therapy. Similar to embodiment of FIG. 22A, this embodiment can include multiple filters (a primary and a secondary membrane). However, in this embodiment the primary membrane 2204 can include pores sized and configured to allow for the free movement of blood plasma while retaining RBC, WBC's and platelets to the blood facing size. The secondary membrane 2206 can have pores much smaller than the primary membrane as to allow for the free passage of gases but not liquids. Over the course of a treatment several milliliters or plasma can be collected for sample analysis in the secondary chamber. During or at the end of treatment this sample can be withdrawn either by manual or automated methods. The sample could then be transported to a blood plasma/serum analyzer. For example, a sample can be manually withdrawn from the tap 2210 and transported to a plasma/serum analyzer, or alternatively, the tap could be connected (via a tube) directly to the blood plasma/serum analyzer for automated sampling and analysis. The analyzer can employ the use of spectrum analysis (UV-Vis) assay testing for specific proteins or molecules.

Figure 23A:
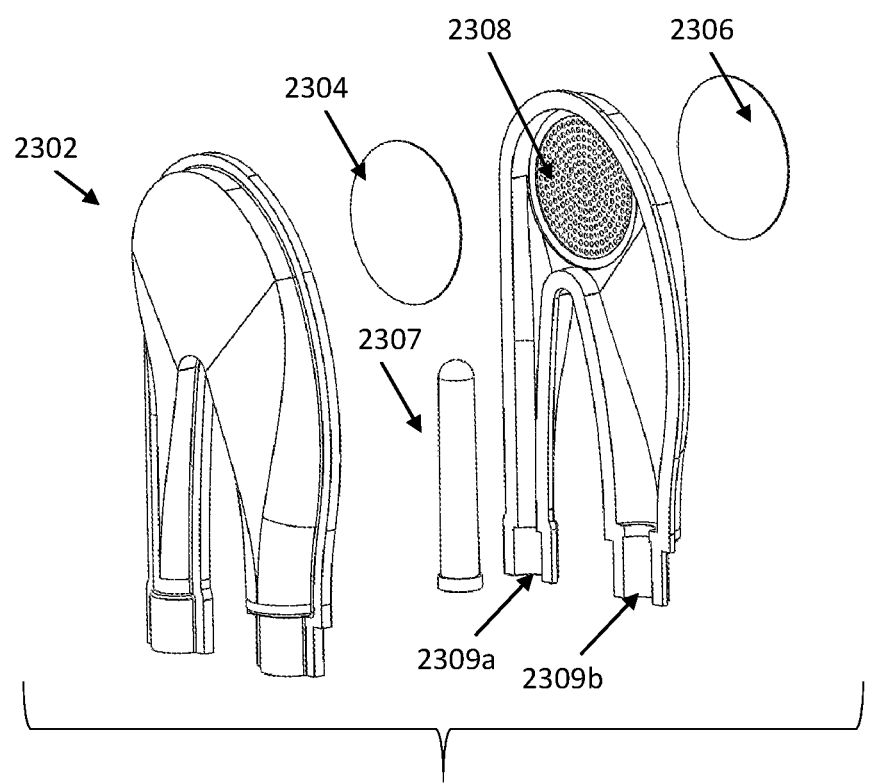
FIGS. 23A-23B illustrate another embodiment of a flow chamber for a dialysis system.
Figure 23B:
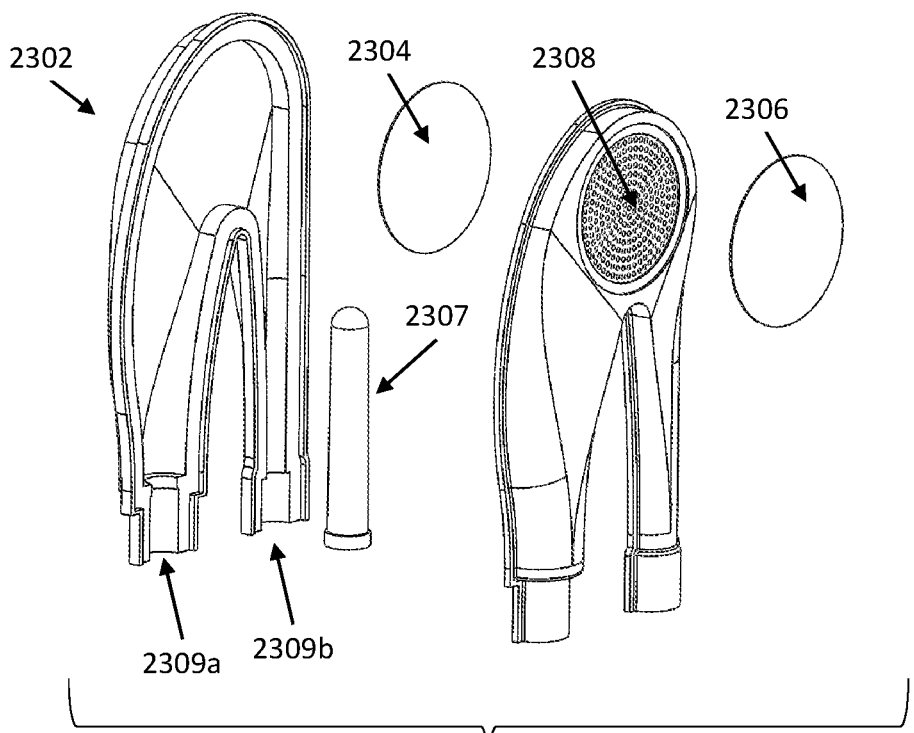

FIGS. 23A-23B are exploded views of an alternate embodiment to the air removal chamber of FIGS. 22A-22B. Air removal chamber 2402 includes many of the same features as air removal chamber 2202 described above, including a primary chamber, a primary membrane 2304, a secondary membrane 2306, and a secondary chamber 2308 disposed between the primary and secondary membranes. The air removal chamber 2402 can further include a clot filter 2307 configured to prevent clots from traveling downstream towards the patient. As illustrated in FIGS. 23A-23B, the secondary chamber 2308 can further include a perforated support structure such as a mesh, honeycomb, or porous substrate, the perforated support structure designed and configured to provide mechanical support and separation between the two membranes. The porosity of the perforated support structure still allows for the collection and storage of blood plasma during the course of treatment. As further illustrated in FIGS. 23A-23B, the air removal chamber can include an inlet 2309a and an outlet 2309b. The inlet and outlet allow fluid, such as saline or blood, to flow in and out of the air removal chamber. Unlike the air removal chamber of FIGS. 22A-22B, in which the membranes are perpendicular to the flow path, the embodiment of FIGS. 23A-23B includes membranes that are positioned parallel to the general plane of the flow path through the primary chamber.

Pore filtration is a common method for removing particulate of a given size. To pass a fluid through a given orifice size a pressure gradient is required. The pressure required to move the fluid through the pore is a function of the pore size, the fluid viscosity, the pressure gradient. Surface tension and surface energy of the filter may also play a role as it establishes the contact angle that must be created within the pore space as the fluid proceeds. While both the pore size and the pressure are constant, the dynamic viscosity of a gas an air are different by orders of magnitude, thus the pressure requiring flow will be lower for the fluid with a lower viscosity. This allows a gas to pass through the filter, when the internal pressure of the system ($P1$) is greater than the cracking pressure or minimum pressure required for gas to flow through. For fluid to effectively flow through, a higher pressure is required for a given time scale. However over time, due to the microfluidic interactions of capillarity and microchannel flow, small volumes of liquid may pass through the filter. The purpose of the secondary chamber between the two membranes, as well as the volume of the secondary chamber, is to both contain the filtrate/plasma as well as allow enough of a buffer to accumulate the filtrate/plasma over a given duration of treatment.

The volume of the secondary chamber between the two membranes is both a function of the volume of fluid it contains as well as the separation distance between the two filters. The volume of fluid it contains is a function of how much fluid passes through the primary membrane over a period of time. The height of the secondary chamber is a function of the puddle height of the fluid. The puddle height of the fluid is a function of the surface tension of the fluid itself as well as the surface energy of the fluid. A distance can be set as to allow the fluid to puddle up but without touching the secondary membrane. By setting this distance appropriately the life of the cartridge can be extended while also minimize cartridge size. The effusion rate of a particular membrane is established. This allows for a volume estimation on how much filtrate should be contained within this secondary chamber to maximize cartridge life. The containment volume combined with the desired puddle height information allows for an optimal design to be created in which allows for both an efficient use of space as well as maximizing on board cartridge time.

For standard blood serum/plasma collection the blood must be manipulated to separate the plasma from the cellular material and then again to get the blood serum. Conventional methods employed the use of a centrifuge to spin down the sample. Centrifugal motion will cause the heavier material to move to the bottom of the test tube. The plasma will form as layer at the top in which it can be removed by either automated or manual methods. The clear and colored plasma can be analyzed be spectroscopy as it is free of debris that would scatter the light. The spectral absorbance of this fluid is unique to the spectral absorbance of the proteins, ions, and molecules that form the plasma and thus can be measured. The present disclosure advantageously provides an apparatus and that can separate cellular material from blood automatically during a dialysis treatment, without the need to use a centrifuge to spin down the sample.

Figure 24:
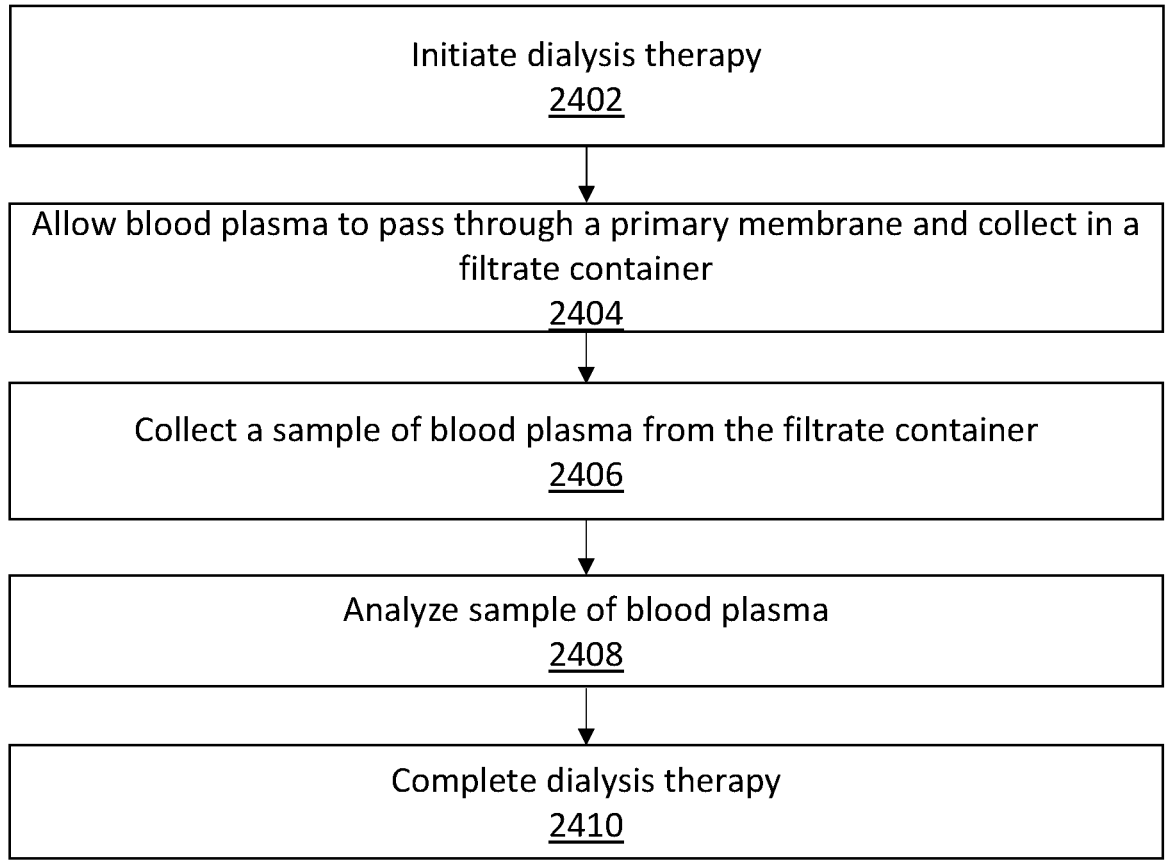
FIG. 24 is a flowchart illustrating a method of collecting blood plasma during dialysis therapy.

FIG. 24 is a flowchart illustrating a method of performing dialysis therapy. At step 2402 of FIG. 24, dialysis therapy can be initiated. In some examples, as described above, blood flows from a patient through the dialysis system and is returned to the patient. During the course of therapy, the blood can pass through a drip chamber or air removal chamber, such as the chambers described above in FIGS. 22A-22B and 23A-23B. At step 2404 of FIG. 24, the dialysis system can allow blood plasma to pass through a primary membrane of a drip or air removal chamber and collect in a filtrate container. For example, blood plasma can pass through primary membrane 2204 and collect in secondary chamber 2208 of the embodiment of FIGS. 22A-22B. In some embodiments, the treatment begins with the filtrate container. As the dialysis treatment progresses this filtrate container begins to fill up with blood plasma. Next, at step 2406 of FIG. 24, a sample of the blood plasma can be collected from the filtrate container. This sample can be collected during the course of the dialysis therapy (e.g., at a predefined time), or alternatively, can be collected after the therapy has completed. In one example, the sample can be withdrawn through a port or tap (such as tap 2210 in FIG. 22B) in which sample sterility and integrity is maintained. Next, at step 2408, the sample can be transported to a blood plasma/serum analyzer and the blood plasma can be analyzed. As described above, the sample can be manually withdrawn from the chamber and transported to the analyzer, or alternatively, can be automatically transported and analyzed. This analysis could occur during the course of the dialysis therapy, or alternatively, after the therapy has completed. With standard spectrometers, the analysis vessel stays in place while a diffraction gradient passes light of various frequencies through the vessel to a detector. Finally, at step 2410, the dialysis therapy can be completed. All materials that came in physical contact with the sample would be disposed of at the end of the treatment session.

Figure 25:
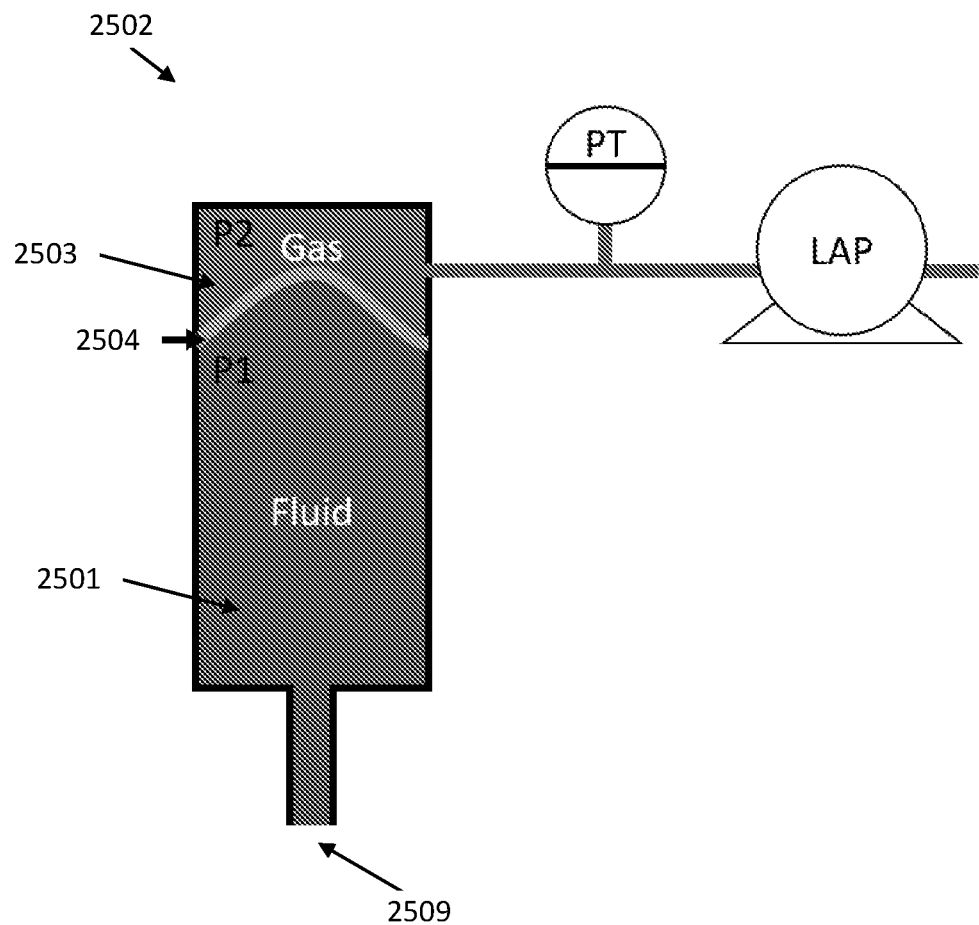
FIG. 25 is another embodiment of a flow chamber for a dialysis system.

Yet another embodiment of an air removal chamber is shown in FIG. 25. The air removal chamber 2502 can include a primary chamber 2501 and a gas removing chamber 2503, separated by a deformable ventable membrane 2504. The chamber can include fluid inlet/outlets 2509, illustrated as a single tube in this example, but it should be understood that the inlet and outlet can be separate as described above. The air removal chamber can further include a pressure transducer PT and a level adjusting pump LAP, both being fluidly connected to the gas removing chamber 2503 as shown. The gas removing chamber can vent to atmospheric pressure via the pressure transducer and the level adjusting pump for the removal of air/gas from the air removal chamber. While the embodiment of FIG. 25 includes an air removal chamber with only two chambers and a single membrane or filter, it should be understood that the pressure transducer and LAP of FIG. 25 can be used with other air removal chambers described herein, such as the air removal chambers of FIGS. 22A-22B.

Extracorporeal circuit gas removal as well as leak detection is critical for safe and effective treatment. To remove gas across the selectably ventable filter, a pressure differential is required. Gas will move across this membrane proportional to the pressure gradient driving it. If faster rates of flux are required either the surface area of the filter needs to be increased or the pressure gradient does. A larger filter will require more space and only serves the purpose of efficiently venting gas during priming but then the added area is wasted for the remainder of priming and treatment, thus a larger filter is not an efficient use of material.

The ventable membrane of the air removal chamber allows for the free passage of gas. When one portion of the air removal chamber is open to atmosphere via the pressure transducer/level adjust pump, the driving pressure across the membrane can only be as large is the pressure within the primary chamber 2501. By attaching the secondary chamber 2503 to a level adjusting pump LAP, several new functions can be employed such as an adjustable pressure gradient for efficiently removing air when desired as well as circuit leak detection.

The ability of the LAP to detect and control the pressure gradient across the membrane is balanced between the system blood pump's ability to create an internal pressure within the air removal chamber, the LAP's ability to remove air, and the membrane's ability to retain liquid. As the blood pump of the dialysis system pushes fluid out the venous side of the patient tubing set, the internal pressure on the venous side will be positive and the ventable membrane will distend with the pulsatile nature of the pump. A vacuum created by the LAP on the gas removing side of the membrane will be at a steady state until air passes through the filter from the primary chamber side, thus increasing the mass density of the air on the dry side thus raising the pressure the LAP sees.

To facilitate a priming process the LAP can be employed to look for leaks as well as determine if the system has been fully primed. If higher rates of air removal are desired, a higher vacuum level can be created by the LAP thus increasing the pressure gradient across the filter. During operation, the LAP can be periodically cycled to maintain a vacuum on the dry side. If air passes across the filter this will be detected as a rise in pressure and the LAP can either by cycled to facilitate a quicker removal of air or maintain a predetermined pressure.

Figure 26:
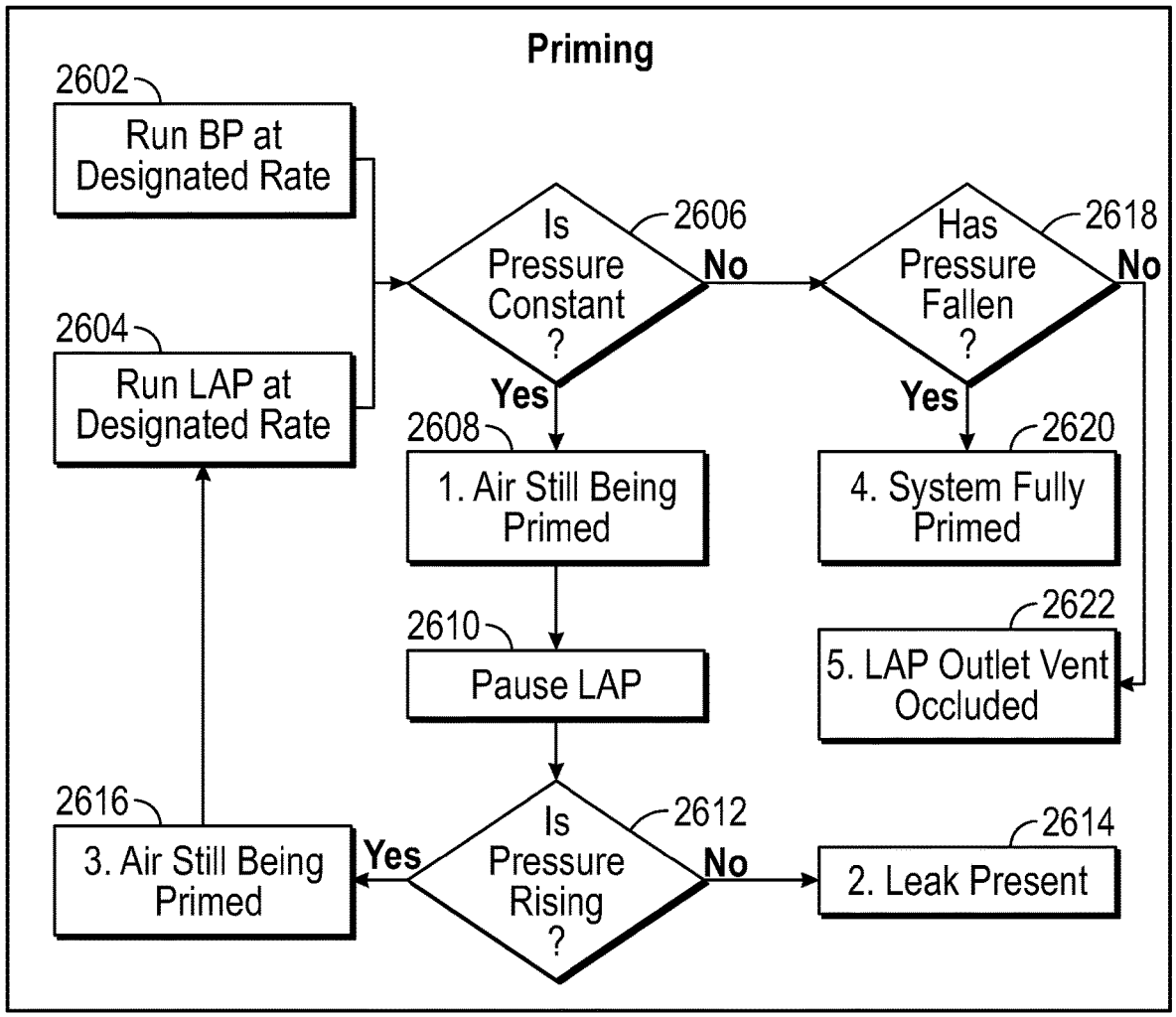
FIGS. 26 and 27 illustrate flowcharts describing methods of using the flow chamber of FIG. 25.

FIG. 26 is a flowchart describing a method of priming an extracorporeal blood circuit or patient tubing set prior to dialysis therapy. The flowchart can refer to hardware described above, particularly the dialysis systems described above and the air removal chamber of FIG. 25. Referring to the flowchart of FIG. 26, at the start of a priming sequence, at step 2602 a blood pump of the dialysis system can operate at a designated flow rate to cause saline or another priming fluid to flow into the patient tubing set, thus displacing air from the patient tubing set via the air removal chamber. During this stage, at step 2604, the level adjust pump LAP can also be operated at a designated rate to create a vacuum above the ventable filter (such as in the gas removing chamber 2503 of FIG. 25). This vacuum increases the pressure seen across the ventable filter, thus expediting the rate at which air passes through the filter and reducing the time required for priming. While the blood pump and level adjust pump are running, the dialysis system can continuously monitor a pressure within the system, such as within the blood chamber or within gas removing chamber (e.g., the dry side of the ventable filter in the air removal chamber). If, at step 2606, the monitored pressure is relatively constant (e.g., the pressure in the blood chamber is relatively consistent with the pressure in the gas removing chamber, or alternatively, the pressure in the gas removing chamber remains relatively constant/stable), then at step 2608, the system determines that air is still being primed from the blood tubing set, and at step 2610 the operation of the level adjust pump can be stopped (e.g., the pump can be turned off). Step 2608 in the flowchart of FIG. 26 can occur because the rate at which air is being pumped through the ventable filter from the blood pump matches the rate at which it is being cleared by the level adjust pump. At step 2612, the system can continue to monitor the pressure to determine if the pressure is rising. If the pressure is not rising with the LAP disabled, then at step 2614 the system can determine that a leak is present due to air being pumped in via the blood pump, indicating the air must be escaping from somewhere else in the system. Instead, if the pressure is rising, then at step 2616 the system can determine that air is still being primed. In this scenario, air is being forced into the LAP chamber and has nowhere to escape because the LAP is paused, indicating that no detectable leak is present. At this point the control loop can return to running LAP at a predefined rate (e.g., returning to step 2604).

If, instead, at step 2618 the monitored pressure is not constant, when both the LAP and the blood pump are running, a second decision point can be reached by the system. If the pressure is falling (e.g., the pressure in the blood and/or gas removing chamber substantially drops from the previously constant pressure, or alternatively, the pressure lowers or begins to approach a vacuum), then at step 2620 the system can determine that the extracorporeal circuit is now fully primed as no more air can pass through the ventable filter to replenish the air that LAP is removing. If, instead, the pressure is rising, then at step 2622 the system can determine that the LAP vent is occluded as it is not able to expunge air from the system.

Figure 27:
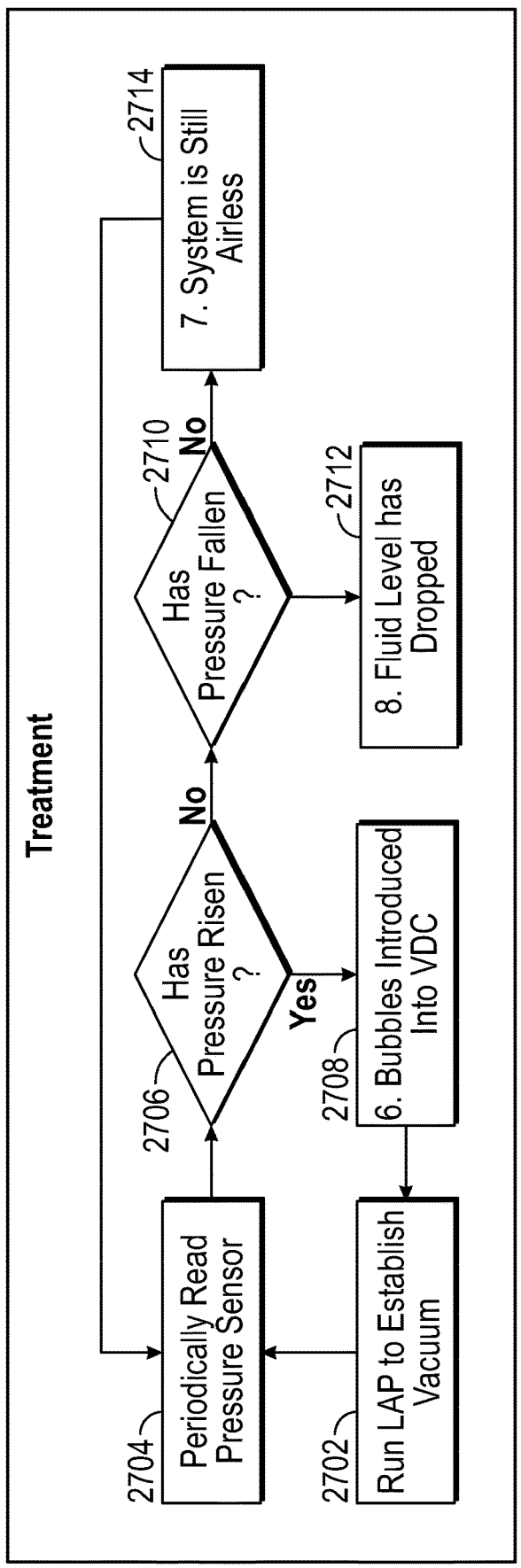

The level adjust pump of the air removal chamber of FIG. 25 can also provide useful features during treatment. Referring to FIG. 27, the level adjust pump can enhance the removal of unwanted air, gas, or bubbles from the system. First, at step 2702, the LAP would be operated periodically during dialysis therapy to maintain/establish a predefined vacuum in the gas removing chamber (e.g., the dry side of the ventable filter of FIG. 25). At step 2704, the system can monitor a pressure within the gas removing chamber (e.g., at the pressure transducer PT in FIG. 25). If the internal pressure has risen (at step 2706) the system can then determine at step 2708 that there has been an increase in the air mass of the gas removing chamber, and therefore either air, gas, or bubbles are passing through the ventable filter or a leak has occurred in the gas removing chamber. The flowchart can return to step 2702, in which the level adjust pump can continue to operate to increase the vacuum, thus expediting the rate at which air, gas, or bubbles are removed from the system. If the pressure has fallen (at step 2710) the system can determine at step 2712 that the fluid level in the air removal chamber has dropped and therefore the air, gas, or bubbles have moved freely across the ventable filter. If the pressure has neither risen or fallen, then at step 2714 the system can determine that the extracorporeal circuit is in an airless state.

Figure 28:
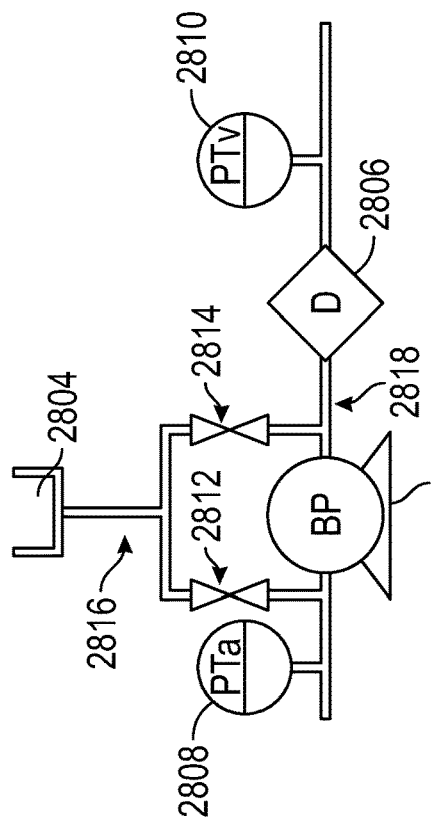
FIG. 28 is a schematic diagram of a fluid flow path of a dialysis system.

FIG. 28 is a schematic diagram of one configuration of a dialysis system, including a blood pump 2802, a saline source 2804, a dialyzer 2806, an arterial pressure transducer 2808, a venous pressure transducer 2810, an arterial saline pinch valve 2812, a venous saline pinch valve 2814, and a patient tubing set 2816. Dialyzer clotting is a problem associated early termination of dialysis treatments. A system and method is disclosed herein to detect dialyzer clotting by measuring the pressure drop across the dialyzer at the beginning of treatment and then periodically throughout the treatment. As clotting begins to form, the pressure drop across the dialyzer will increase as the flow becomes more restricted due to the accumulation of clotted material. The present disclosure utilizes the preexisting saline lines which by nature create a second closed fluidic pathway between preexisting arterial and venous pressure measurement points, the pressure post blood pump but pre-dialyzer can be inferred without the need for additional hardware or costly sensors.

To infer the post blood pump but pre-dialyzer line pressure (located at position 2818 in the patient tubing set) two prior measurements must first be made. The first measurement is a baseline pressure measurement on the arterial side, which will always be negative during treatment. This measurement is taken with both the arterial saline pinch valve 2808 and the venous saline pinch valve 2814 closed, thus only measuring the negative pressure produced by the blood pump 2802. The second measurement is the hydrostatic pressure applied by the height of the fluid level in the saline bag. To measure this, the arterial saline pinch valve 2808 is opened. This pressure is negative so the added pressure from the hydrostatic pressure head will cause the arterial pressure to rise. Subtracting the baseline pressure measurement from the hydrostatic pressure head will give the positive hydrostatic pressure from the saline bag. To then measure the pressure at position 2818, both saline pinch valves can be opened. The positive pressure from position 2818 will cause the arterial pressure to rise. The rise of the arterial pressure subtracted from the hydrostatic contribution of the saline bag height will be the line pressure at position 2818. If the arterial line pressure is sufficiently negative to allow the saline bag fluid level to drop with the venous saline pinch valve open, the post blood pump, pre-dialyzer line pressure can be inferred by the system.

Figure 29:
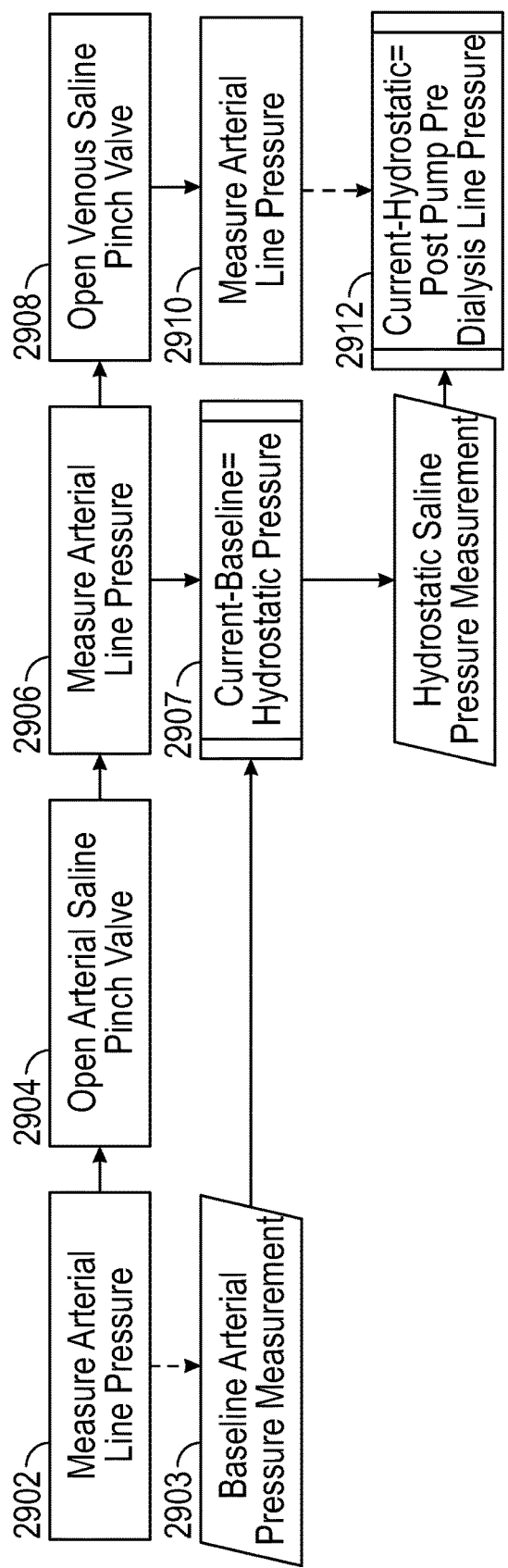
FIGS. 29 and 30 are flowcharts describing methods of using the dialysis system of FIG. 28.

FIG. 29 illustrates a method of using the system described above to infer the post blood pump pressure. During all the steps described, a blood pump of the dialysis system will be operating. As described above, at step 2902, the dialysis system can measure an arterial line pressure, such as with an arterial pressure sensor. This measured pressure can be the baseline arterial pressure measurement at step 2903. Next, at step 2904, the arterial saline pinch valve can be opened, and at step 2906, the arterial line pressure can again be measured by the system. At step 2907, the hydrostatic pressure of the saline bag can be calculated by subtracting the baseline arterial pressure measurement from the arterial pressure measured at step 2906 (the current pressure measurement). Next, at step 2908, the venous saline pinch valve can be opened, and at step 2910 the arterial line pressure can be measured again by the system. Finally, at step 2912, the hydrostatic saline pressure measurement from step 2907 can be subtracted from the arterial line pressure measured at step 2910 (the new current pressure measurement) to determine the line pressure at the point in the patient tubing set after the blood pump but before the dialyzer (e.g., at position 2818 in FIG. 28).

Figure 30:
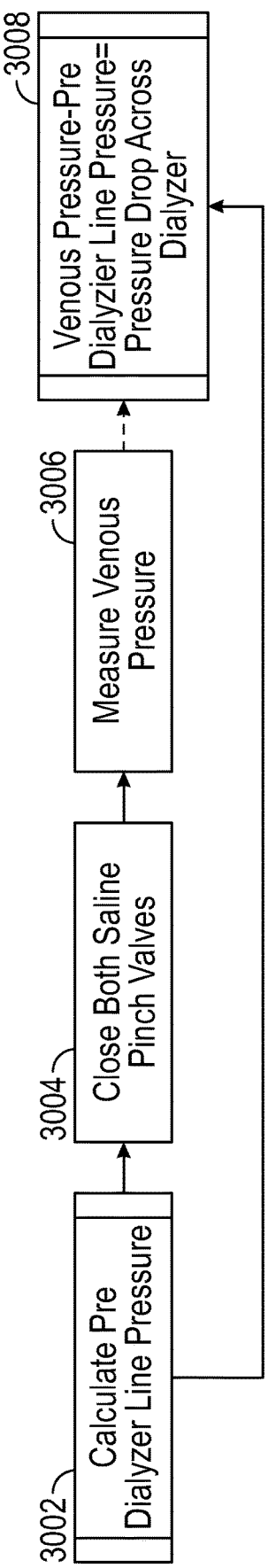

FIG. 30 illustrates a method for measuring a dialyzer pressure drop, using the post blood pump, pre-dialyzer pressure calculated using the method of FIG. 29. At step 3002, at the start of treatment, the post blood pump pre-dialysis line pressure (e.g., the line pressure calculated at step 2912 of FIG. 29) can be calculated and recorded. Next, at step 3004, both the arterial and venous saline pinch valves can be closed, and at step 3006, the venous pressure can be measured (such as with a venous pressure sensor). Finally, at step 3008, the pre-dialyzer line pressure from step 3002 can be subtracted from the venous pressure measured at step 3006 to establish pressure drop across the dialyzer.

At periodic cycles during the treatment the dialyzer pressure drop can be calculated and recorded according to the technique described above. Based on previously established values (lab testing) a critical pressure limit could be established for each dialyzer type. This could serve to let the system know how much of a pressure drop is acceptable before clearance is adversely impacted.

During a normal treatment the system can constantly monitor the state of the system and the patient. When the pressure drop across the dialyzer exceeds a clearance threshold where the efficacy of the treatment has been compromised, the system can produce an alert, popup, or audible alarm would. This can allow the user to continue treatment until clotting physically disrupts the process. At this point, the user can: 1) change the cartridge/dialyzer set to allow the patient to continue to have an efficient treatment; or 2) back flush the dialyzer with saline to free any clotted material and allowing the patient to resume treatment. The pressure drop seen with each type of dialyzer maybe slightly different therefore reference studies can be performed to establish the acceptable limits of pressure drop for each dialyzer type. At the start of treatment, the specific dialyzer type can be entered into the dialysis system, thus allowing the system to set a tailored pressure limit to the unique hardware on the system at the time of treatment.

Systems and methods are also provided herein for producing dialysate in real time either prior to or during a dialysis treatment, directly on the dialysis machine. Bicarbonate-based dialysate requires three components: purified water, acid concentrate, and bicarbonate concentrate. The acid concentrate is a heterogenous mixture, and contains the majority of the sodium, as well as other constituents such as calcium, potassium, magnesium, dextrose and an acid component, usually acetic acid. In contrast, the bicarbonate concentrate is typically a homogenous solution of sodium bicarbonate. Both concentrates may be provided as pre-mixed liquids, which are proportioned by a dialysis machine with water to create dialysate of the desired composition. Because of its homogenous nature, it is possible and known in the art to provide bicarbonate in the form of sodium bicarbonate powder in a container with sufficient quantity to provide one treatment worth of bicarbonate. Purified water is then added to this container by the dialysis machine, and a saturated solution of sodium bicarbonate is produced. The advantage to this approach is a smaller package, which is logistically easier and cheaper to ship and store. Some dialysis machines are able to support both liquid and powdered bicarbonate formats. However, due to their differing requirements, the physical hardware to interface with either a liquid bottle, or a canister of powdered bicarbonate is different and separate, adding size and complexity to the machine.

When using a powdered bicarbonate canister, it can be advantageous to withdraw the saturated concentrate solution from the bottom of the canister, once the purified water is added. This is due to gravity, as any air that may be in the canister, either from packaging or from the chemical reaction of dissolving bicarbonate will tend to rise to the top of canister. As water starts to be added to the canister, to prevent overpressurization of the canister, the air within the canister must be allowed to leave the canister. If this air exits via the outlet that draws out the fluid for further proportioning, there must exist mechanisms downstream, within the dialysis machine to remove this air. This increases internal complexity of the machine. Aggressively degassing the saturated bicarbonate solution with techniques such as elevated temperature or negative pressure is not advisable, as the bicarbonate within solution will enter gaseous state as carbon dioxide and leave the solution.

The present disclosure includes a dialysis system including a dialysate delivery subsystem that can perform three functions related to dialysate production and delivery: (1) create liquid bicarbonate concentrate from a canister of powdered bicarbonate to deliver for proportioning, (2) deliver pre-mixed liquid bicarbonate concentrate for proportioning, and (3) provide a rinsing function to rinse all internal concentrate lines with purified water. The dialysate delivery subsystem can include a number of components depending on the configuration.

Figure 31A:
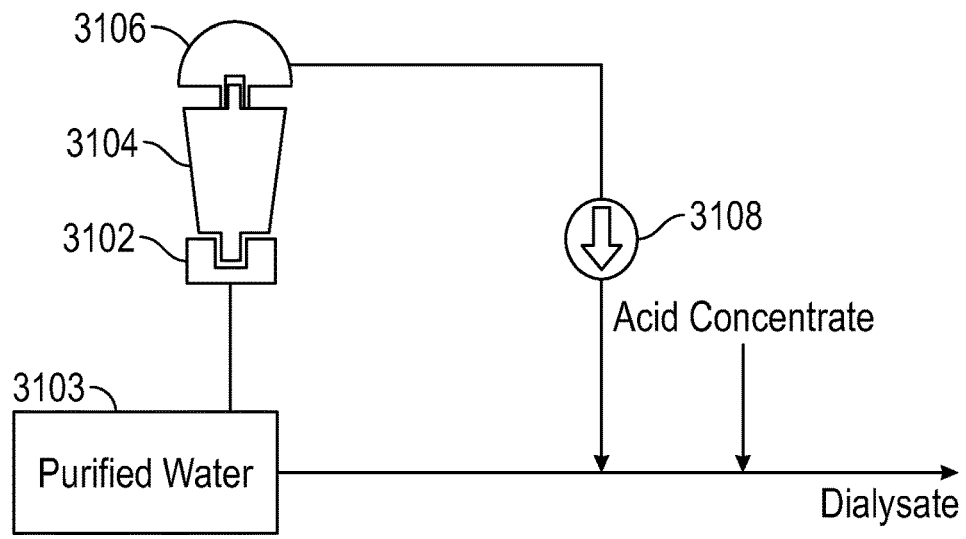
FIGS. 31A-31C illustrate various configurations of a dialysis system for preparing and/or delivering a dialysate solution.

In a first configuration, referring to FIG. 31A, the dialysate delivery subsystem is designed and configured to produce dialysate from a powdered bicarbonate canister. This configuration can include a water supply port 3102 which is in fluid communication with a source of purified water 3103. The water supply port 3102 can be disposed on or within a dialysis system, such as the dialysis systems described above. The water supply port can include a selectively openable/closable valve mechanism which will be described in more detail below. Still referring to FIG. 31A, the dialysate delivery subsystem can further include a bicarbonate canister 3104 configured to mate with the water supply port, thereby opening the valve mechanism of the water supply port. The dialysate delivery subsystem can further include a concentrate connection cap 3106 configured to mate with the bicarbonate canister 3104. In another configuration, described below in FIG. 31C, the concentration connection cap mates directly with the water supply port. A pump 3108 of the dialysis system can be connected to an outlet of the concentrate connection cap. The pump can be operated both to pull purified water into the canister to mix with the concentrate, and also to pull mixed bicarbonate solution from the canister into the patient tubing set of the dialysis system, where it can be later mixed with an acid concentrate to produce dialysate.

Figure 32A:
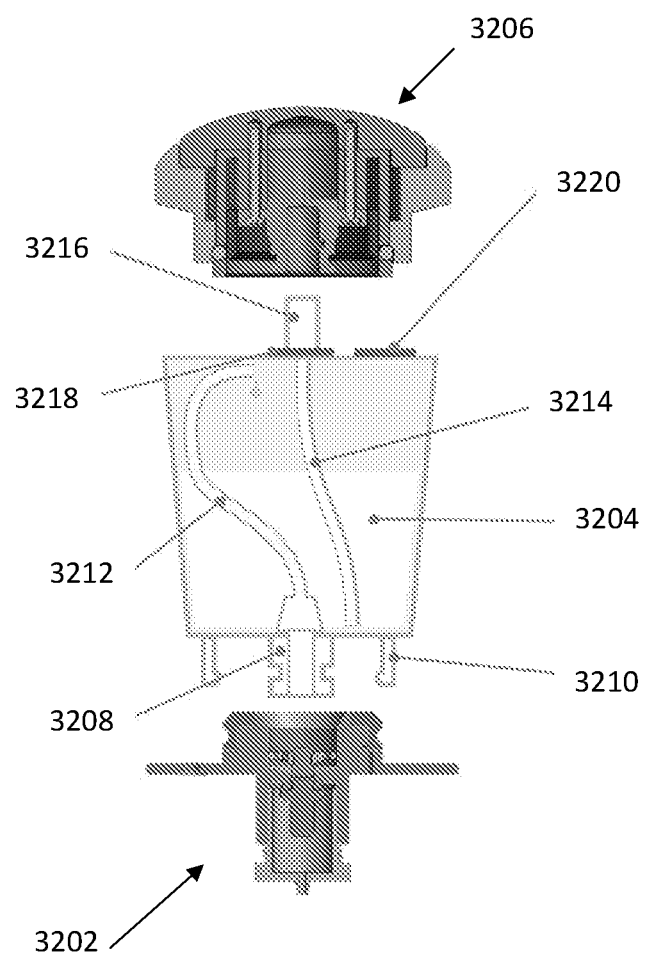
FIGS. 32A-32D illustrate configurations of a dialysis system for preparing dialysate from a powdered bicarbonate canister.

FIG. 32A is a detailed view of the dialysate delivery subsystem in the configuration of FIG. 31A. As described above, the dialysate delivery subsystem can include a water supply port 3202, a powdered bicarbonate canister 3204, and a concentrate connection cap 3206. The powdered bicarbonate canister can include a docking protrusion 3208 configured to mate with the water supply port, and can optionally include mechanical fixation devices 3210 such as snap fingers to cause the canister to remain connected to the water supply port. The canister can further include an inlet conduit 3212 configured to deliver purified water from the water supply port into the canister. The canister can further include an outlet conduit 3214 configured to deliver the mixed bicarbonate solution out of the canister through an outlet 3216 into the concentrate connection cap 3206. The outlet 3216 can include an outlet filter 3218 and a hydrophobic filter 3220 for venting.

In the configuration of FIG. 31A and FIG. 32A, the powdered bicarbonate canister plugs into or mates directly with the water supply port, opening the shutoff in the water supply port, and the concentrate connection cap mates with the bicarbonate canister. The pump can be operated to cause water from the purified water source to flow into the powdered bicarbonate canister and through the inlet conduit of the canister. Preferably, the purified water is of known temperature, as the solubility of bicarbonate in water is temperature dependent. At the terminus of the inlet conduit, the purified water is allowed to drip into the bicarbonate powder solution within the canister. As more water enters, air within the canister escapes through the hydrophobic filter at the top of the canister, displaced by the water. During this filling phase, the dialysis system pump is connected to an outlet of the canister (via the concentrate connector cap). The hydrophobic filter is configured to prevent spillover, as it will seal off when fluid rises to the point where it contacts the filter. Once the filing phase is complete, and when bicarbonate is demanded of the canister, the dialysis system pump can be operated to pump bicarbonate solution out of the canister. As shown in FIG. 32, the outlet conduit 3214 reaches down towards the bottom of the canister. This ensures that any liquid drawn up through this outlet conduit will have substantially traveled throughout the bulk of the bicarbonate powder, causing it to fully saturate. Because the temperature of the fluid is generally known, as well as the saturation concentration of sodium bicarbonate, a desired flow rate by the dialysis system pump can be set to proportion a given quantity of bicarbonate into the dialysate. The pH, or conductivity or other properties of the created concentrate, partially or fully mixed dialysate may be checked by sensors to ensure proper composition.

Figure 31B:
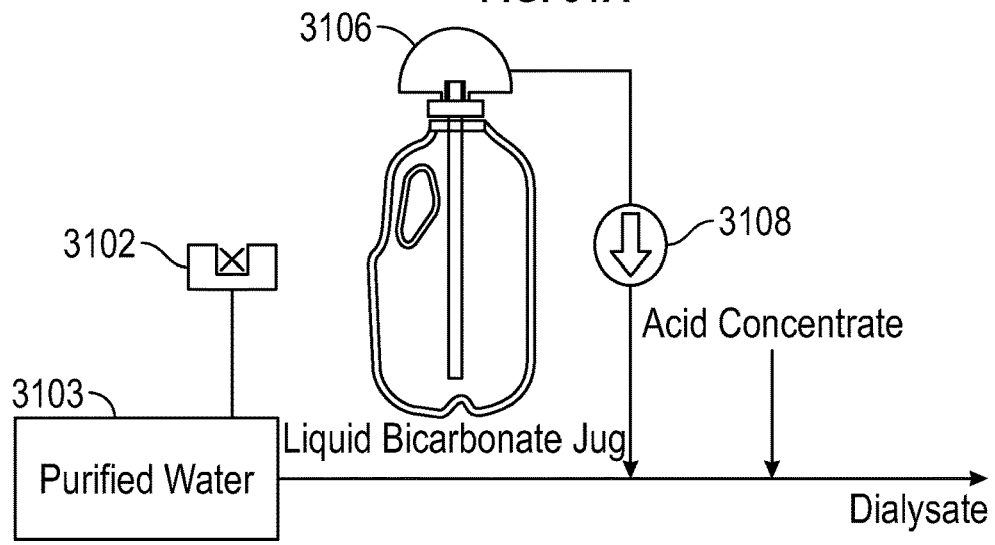
Figure 31C:
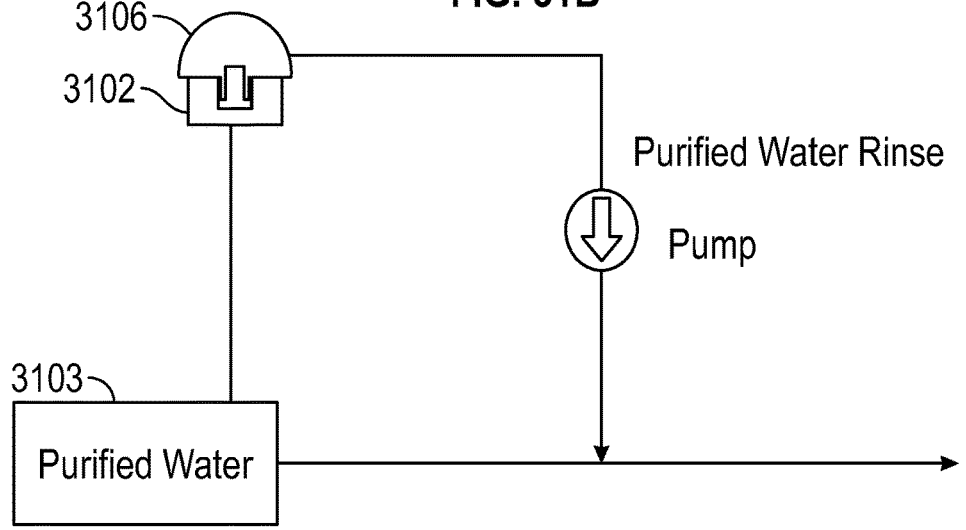
Figure 32B:
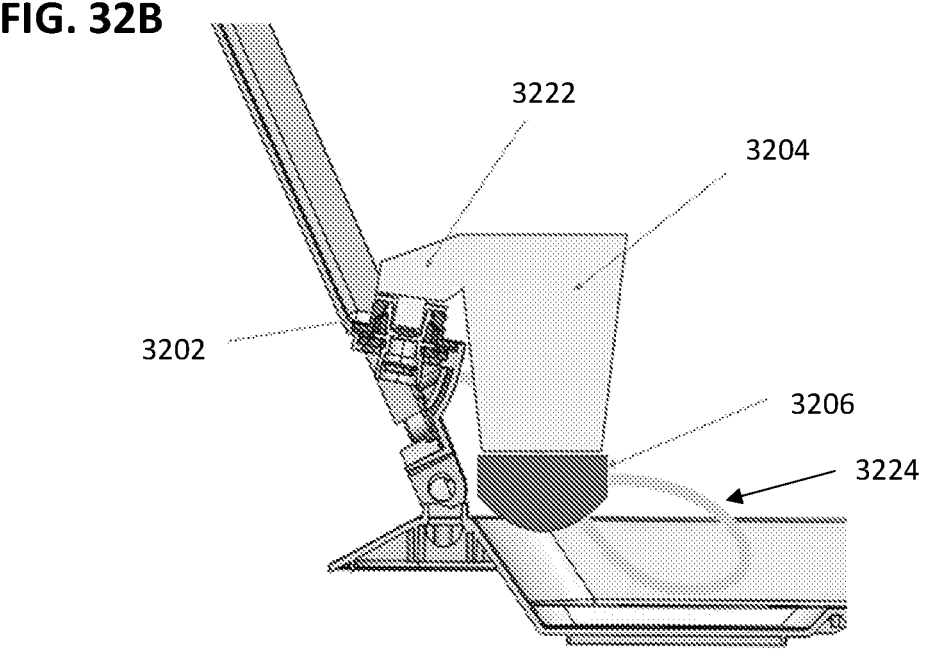
Figure 32C:
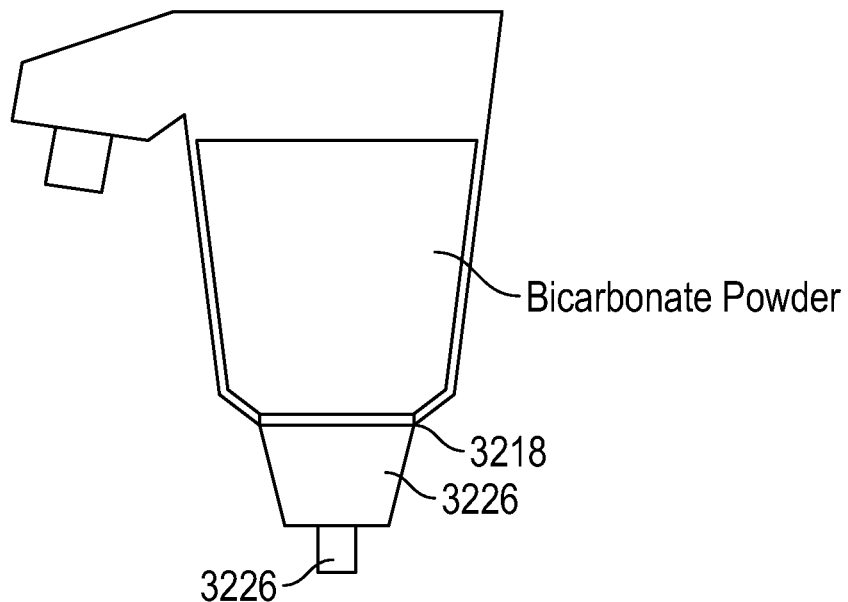
Figure 32D:
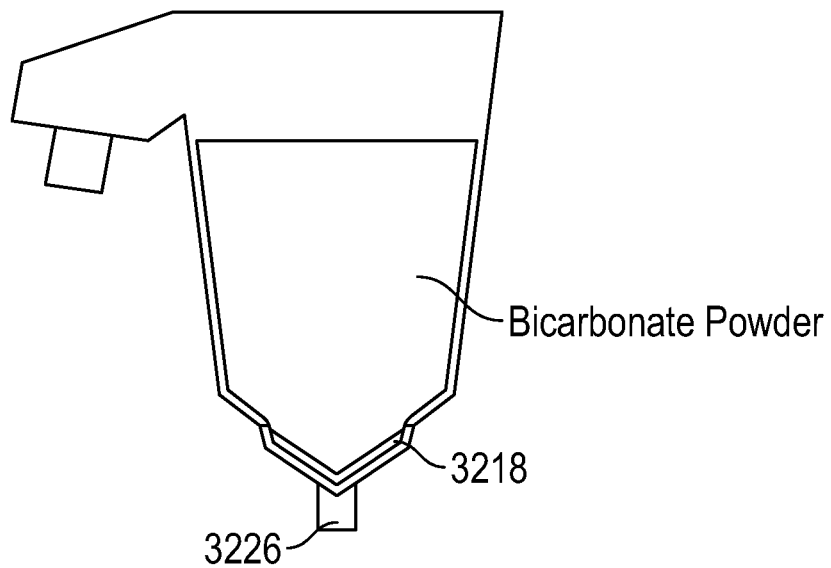

FIGS. 32B-32D are alternate embodiments of the configuration of FIG. 31. In these embodiments, the concentrate connection cap 3206 attaches to the bottom of the bicarbonate canister 3204, which includes a lateral extending section 3222 to cause the canister to extend away from the water supply port 3202. The line 3224 connecting the cap 3206 to the dialysis system (and therefore the dialysis system pump) is also shown.

The embodiment of FIG. 32B provides some unique solutions for managing air infusion into the canister. In the embodiment of FIG. 32C, a filter 3218 can be placed under the bicarbonate powder within the canister such that the filter prevents passage of undissolved powder, but allows liquid in which the contents of the canister have dissolved through. A defined empty volume 3226 can exist under the filter. When the canister is filled with water, the air in this volume 3226 is not able to completely escape, either through the bulk powder, or through the outlet 3216 and concentrate connector cap. As liquid passes through the filter, it must pass through this air column in the volume 3226, which acts like an air removal chamber, separating air from the liquid before it passes through the outlet 3216.

Similarly, in FIG. 32D, an alternate strategy for managing air infusion is to minimize the air volume beneath the filter 3218. The intent of this embodiment is to fully displace the air beneath the filter with fluid, and not have air from that volume itself enter the line. This can be achieved by shaping the filter as a conical surface, with the apex of the conical surface pointing down, and having the filter nest in a cavity that follows the same contour. The outlet 3216 in this embodiment is located at the apex of the conical surface. Compared to the substantially flat filter described above, this design has the advantage of having the outlet be at the substantially lowest point of the canister. Any air would tend to, by buoyant force, collect around the edges of the filter, which would be higher than the exit point, and thus tend not to enter the outlet. In some embodiments, there are no pathways for fluid to pass the filter in the area immediately around its center/apex, therefore forcing fluid and/or air to travel a somewhat tortuous path around the filter, separating air from fluid.

Referring back to FIG. 31B, a second configuration of the dialysate delivery subsystem is provided in which it is configured to deliver pre-mixed liquid bicarbonate concentrate for proportioning. As with the embodiment of FIG. 31A, this configuration includes a water supply port 3102, a purified water source 3103, a concentrate connection cap 3106, and a pump 3108. However, in this second configuration, the powdered bicarbonate canister is replaced with a liquid bicarbonate container 3110. In this example, a straw or cap conduit 3112 is connected to the concentrate connection cap, and the straw or cap conduit is then inserted into the liquid bicarbonate container. With nothing connected to the water supply port, the port itself can be automatically closed. The liquid bicarbonate can then proportioned into the purified water, along with acid concentrate to form the dialysate.

FIG. 31C illustrates a third configuration in which there is no powdered bicarbonate canister or liquid bicarbonate container. This can be referred to as a "Rinsing" configuration, and can also be how the system is stored when not in use. The concentrate connector cap 3106 can be mated to the water supply port 3102, which allows purified water to flow from the purified water source 3103 throughout all the lines in the dialysate deliver subsystem, thereby washing out any residual concentrates.

Figure 33A:
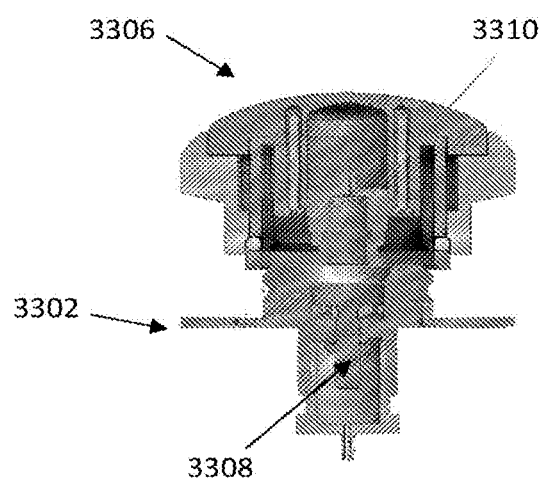
FIGS. 33A-33B illustrate detailed views of a concentrate connection cap of a dialysis system.
Figure 33B:
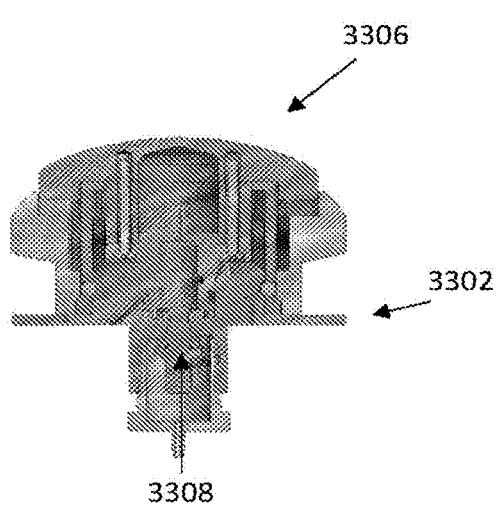

FIGS. 33A-33B illustrate how the concentrate connector cap 3306 mates with and interacts with the water supply port 3302. FIG. 33A shows the concentrate connector cap in which it hasn't yet been mated to the water supply port. It can be seen that the valve mechanism 3308 is in a fully extended position so as to seal off the water supply port with, for example, an o-ring. In the example of FIG. 33B, however, the concentrate connector cap 3306 is pressed down and mated with the water supply port, causing the valve mechanism 3308 to press down and allow a flow of fluid from the purified water source to flow into the concentrate container cap. As is also shown in FIG. 33A, a receptacle 3310 within the concentrate connector cap is shown, which is used to connect to the straw or cap conduit as described above when used with a liquid bicarbonate container.

Systems and methods are also provided herein in which a single dialysis system can be used for both hemodialysis and peritoneal dialysis. Traditionally, hemodialysis (an extracorporeal therapy) and peritoneal dialysis (an intracorporeal therapy) have required different machines and disposables to deliver. While peritoneal dialysis can be convenient from a lifestyle perspective, it may not be efficacious long-term for a large number of patients, and ultimately those patients may need to switch to hemodialysis. PD has also traditionally required large quantities of pre-mixed fluids to be delivered to a patient's home, which introduces high shipping costs and storage issues. The ability to conduct therapy at home, or other patient empowered settings has been shown to improve outcomes. For patients transitioning from peritoneal dialysis (which is often done at home) to hemodialysis, having continuity of equipment is beneficial from a psychological as well as logistical standpoint. Additionally, there is evidence that performing both hemodialysis and peritoneal dialysis on the same patient can be beneficial. Therefore, it would be advantageous to provide a dialysis device which can prepare dialysate from tap water and concentrates that could be used to provide both hemodialysis and peritoneal dialysis modalities.

Within extracorporeal renal replacement therapies, there is further modality stratification. In addition to the location of therapy (home, clinic or hospital), there are modalities such as high-convective therapy (push-pull hemodiafiltration), extended therapies for continuous renal replacement, or pediatric therapies. Each of these therapies may require different configuration on the disposable or machine settings. For example, high-convective therapies require dialysate to be infused into the patient's blood, so the microbial and endotoxin requirements of dialysate used may be higher. Pediatric therapies require much smaller extracorporeal volumes, and therefore maximum pump speeds on a machine should be lower. Therefore, it would be advantageous to produce a single dialysis device that accepts a plurality of disposable configurations, the various disposable configurations each bearing a unique identifier read by the machine which changes features in the machine that are enabled or disabled in software.

Figure 34A:
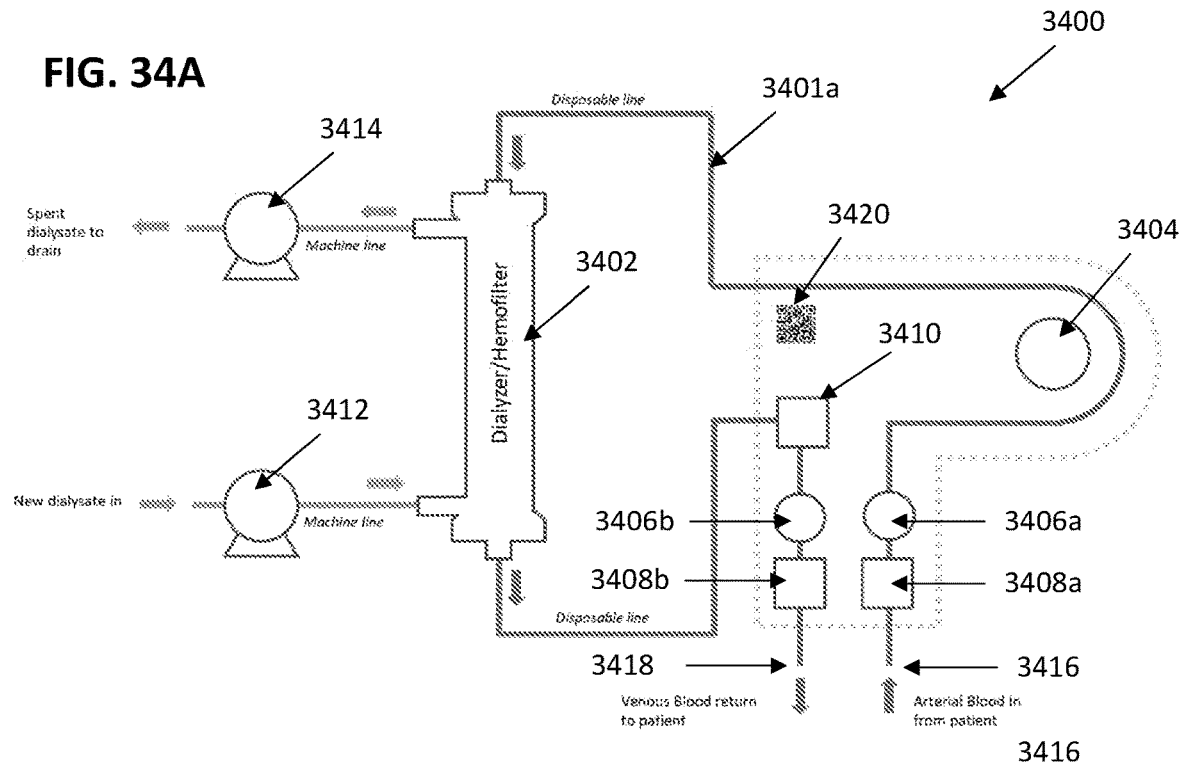
FIGS. 34A-34B illustrate schematic diagrams of an extracorporeal circuit of a dialysis system.

FIG. 34A illustrates a standard configuration of a dialysis therapy system for delivering hemodialysis to a patient. As shown in FIG. 34A, the dialysis system can include an extracorporeal therapy circuit 3400, which can include an extracorporeal patient tubing set 3401a, dialyzer 3402, a blood pump 3404, arterial pressure sensor 3406a, venous pressure sensor 3406b, arterial flow sensor 3408a, venous flow sensor 3408b, air removal chamber 3410. The dialysis machine-side of the system can include a first dialysis pump 3412 configured to pump new dialysate into the dialyzer, and a second dialysis pump 3414 configured to pump old or used dialysate from the dialyzer out of the system to a drain. As is known in the art, arterial blood flows into the extracorporeal therapy circuit 3400 at arterial access point 3416, flows through the circuit including through the dialyzer, and is returned back to the patient at venous access point 3418.

The circuit 3400 of FIG. 34A allows the dialysis system to operate in a standard extracorporeal therapy mode, such as delivering a typical hemodialysis therapy. This mode can also be used to deliver isolated ultrafiltration, where the new dialysate in is zero, but the spent dialysate out is fluid pulled from the blood side of the circuit. An identification mechanism 3420 can be disposed on a cartridge of the circuit, such as a 1D barcode, 2D barcode, RFID tag or other mechanism. In some embodiments, when the cartridge and patient tubing set are installed on the dialysis machine, the identification mechanism is automatically aligned in proximity to a reader on the dialysis. This reader is configured to detect and decode information stored in the identification mechanism, and once mounted, certain features controlled by the software of the machine are enabled or disabled. For example, for a standard extracorporeal therapy cartridge, the machine is configured to set parameters on maximum blood pump speed, treatment time or other parameters, while disabling intracorporeal therapy mode and high convective push-pull mode. If another cartridge, configured for lower extracorporeal volume and thus smaller tubing with its identification mechanism, is detected, then the maximum flow rate settings may be reduced to ensure safe treatment with the smaller flow paths. Since the setup steps for different cartridge configurations could be different, the guided graphical user interface (GUI) setup steps that would then be presented to the user would be different, based on the decoded identification mechanism data. Similarly, data, graphs, alerts, alarms, responses, or other user interface elements presented on the screen after setup, while treatment is active and during takedown may differ based on the same data.

Figure 34B:
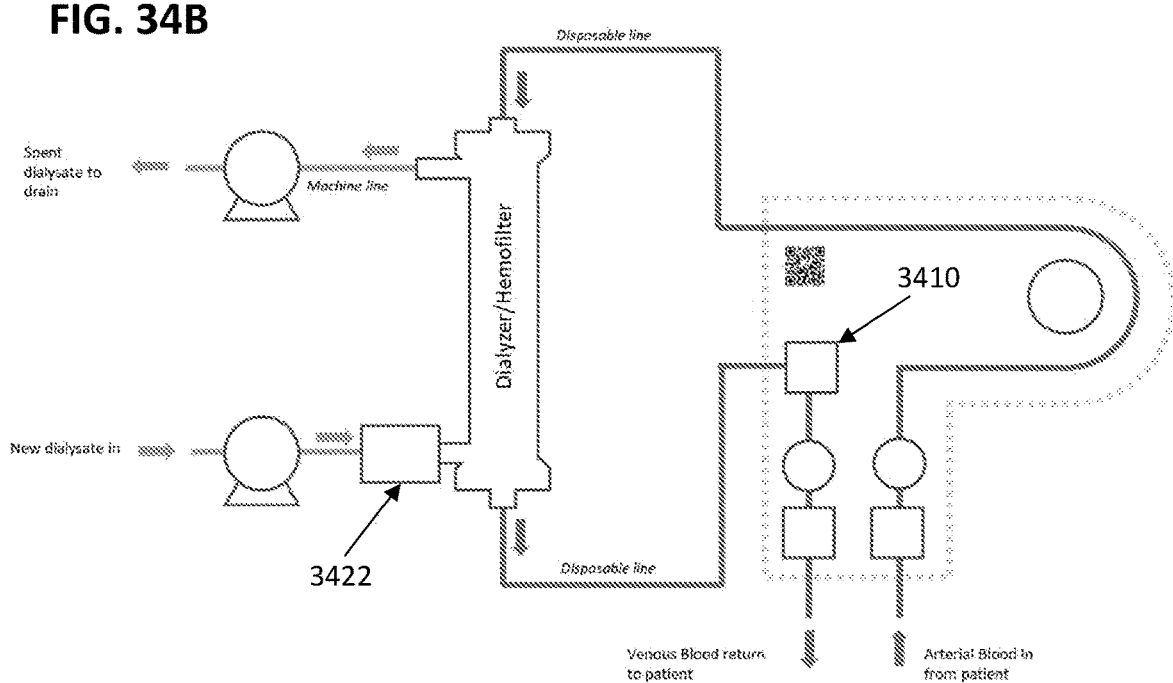

FIG. 34B illustrates one embodiment of an extracorporeal therapy circuit 3400, which includes all the features described above in the embodiment of FIG. 34A, but also adds a disposable, single-use microbe/endotoxin filter 3422. In the illustrated example, this filter is provided on the inlet of the dialyzer/hemofilter where it connects to the machine to receive a flow of dialysate. By providing a single-use microbe/endotoxin filter that is changed every time a new treatment is initiated, high confidence can be provided that the filter is functional and has not been degraded by excess use or disinfection cycles that traditional machine-side filters are subject to. Downstream of the filter, all the fluid paths of the extracorporeal therapy circuit are terminally sterilized before use. For machine-side filters, there is always at least a small portion of fluid path that exists between the filter and any other structure of fluid path that it delivers fluid to. While this line is typically disinfected periodically, assurance of sterility of all downstream fluid paths in the disposable filter arrangement is an improvement. In one embodiment, this filter can be used in conjunction with machine-side filters to produce a double or triple-filtered dialysate stream that is acceptable to infuse into a patient's blood. Preferably, this cartridge has a dialyzer pre-attached to its tubing set, with the single use microbe/endotoxin filter integrated into dialyzer.

Figure 35A:
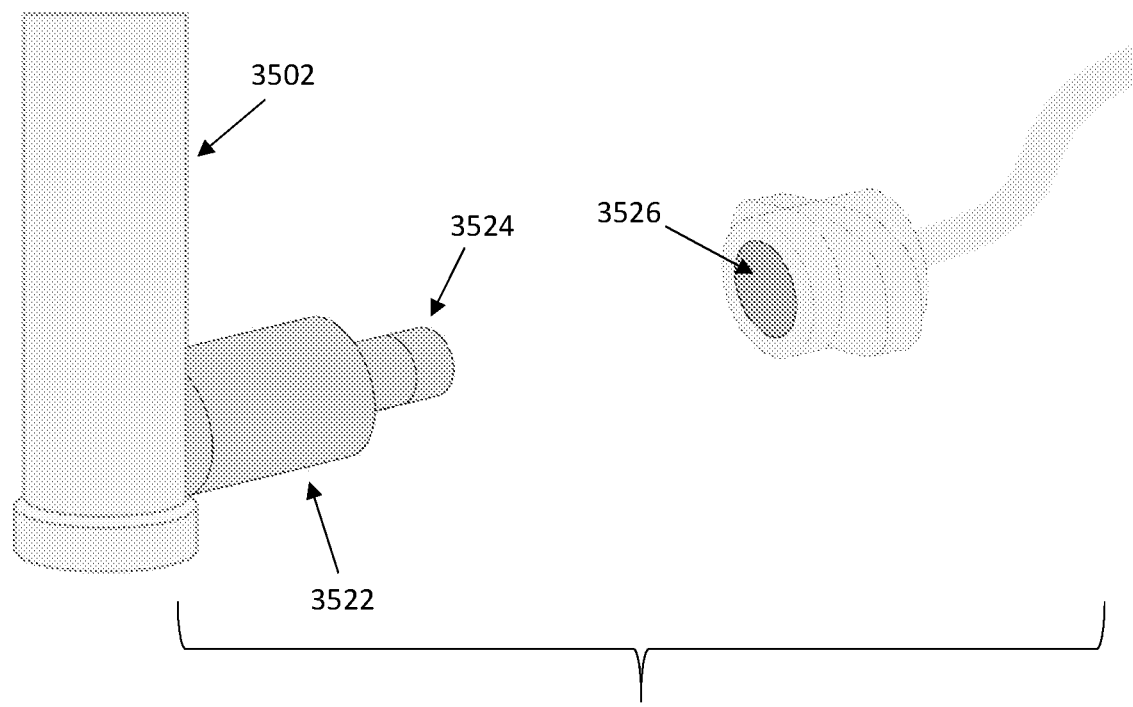
FIGS. 35A-35B illustrate two embodiments of a single-use filter for use with a dialysis system.
Figure 35B:
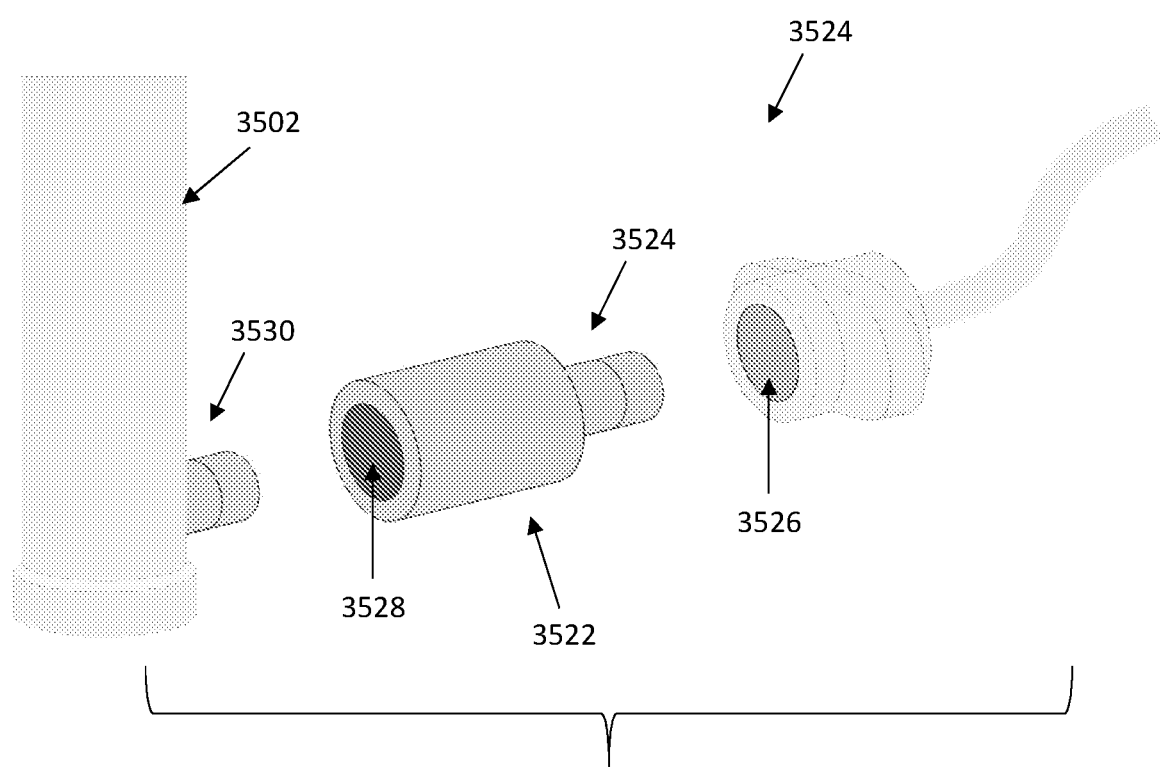

FIGS. 35A and 35B are close up views of two variations of a single-use microbe/endotoxin filter 3522. This can be the same filter as described above in FIGS. 34A-34B. Referring to both FIGS. 35A and 35B, the filter 3522 can include a male Hansen-style fitting 3524 configured to mate with a female Hansen fitting on the dialysis machine to receive the new dialysate flow from the dialysis machine. In the embodiment of FIG. 35A, the filter 3522 is integrated with or incorporated within the dialyzer 3502. In the embodiment of FIG. 35B, however, the microbe/endotoxin filter is a standalone unit that is configured to mate with both the dialyzer 3502 and the dialysis machine. Thus, referring to FIG. 35B, the filter can include a female Hansen-style fitting 3528 on a first side (e.g., to interface with a corresponding male Hansen-style fitting 3530 on the dialyzer)

and a male Hansen-style fitting 3524 on the other side (e.g., to interface with the dialysis machine).

Pre-treatment self-tests (such as looking for a known pressure drop across the dialysate flow caused by the filter) can be conducted by the dialysis machine to ensure that the filter is installed correctly. In either the integrated or stand-alone case, the dialysis machine can be configured to detect the configuration of the filter installed. In addition to enabling standard extracorporeal therapy mode, the dialysis machine can then enable features such as priming the blood set with dialysate (rather than an external sterile saline bag), and enable high-convective therapy where dialysate is sequentially infused into, and withdrawn from the blood in the dialyzer.

Figure 36:
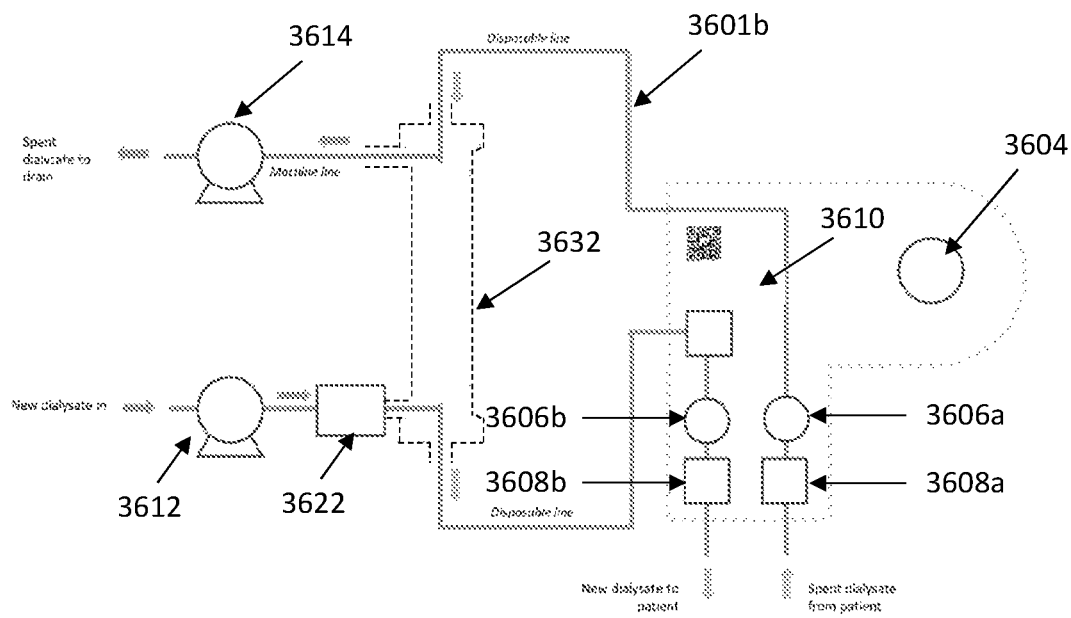
FIGS. 36 and 37 illustrate embodiments of an intracorporeal circuit of a dialysis system.

While FIGS. 34A-34B above describe the use of the dialysis system for providing extracorporeal dialysis therapy, the system can also be configured to provide intracorporeal dialysis therapy. FIG. 36 illustrates a schematic diagram of the dialysis system configured for intracorporeal dialysis therapy. As described above in the extracorporeal configuration, many of the same or similar system components remain in the intracorporeal configuration, including an intracorporeal therapy tubing set 3601, a first dialysis pump 3612, a second dialysis pump 3614, a single-use microbe/endotoxin filter 3622, a blood pump 3604, arterial pressure sensor 3606*a*, venous pressure sensor 3606*b*, arterial flow sensor 3608*a*, venous flow sensor 3608*b*, and air removal chamber 3610. While the blood pump 3604 remains on the dialysis system, it is not used in the intracorporeal configuration and the intracorporeal therapy tubing set 3601*b* bypasses or avoids the pump. Furthermore, with intracorporeal dialysis therapy, a dialyzer is not required since dialysate is infused directly into the patient. However, in some embodiments, a "dummy" or placeholder dialyzer 3632 can be used or incorporated into the tubing set or dialysis system to facilitate mounting and connections with the machine. In one example, the dummy or placeholder dialyzer can comprise a shell that mounts on the dialysis system in the place where the dialyzer mounts (for the extracorporeal configuration). In yet another embodiment, the single-use filter 3622 can be included or incorporated within this dummy dialyzer shell.

The configuration of FIG. 36 facilitates intracorporeal therapy by essentially taking the tubing and flow paths of the extracorporeal therapy tubing set, which are intended to convey blood, and instead using them to convey filtered dialysate. All of the sensor interfaces within the tubing flow path are still functional, and can be used to monitor and meter the delivery of dialysate to the patient. In this configuration, the new and spent dialysate flow are directly connected to the fluid paths of the intracorporeal therapy tubing set. Terminal filtration using a disposable microbe/endotoxin filter can still be highly preferred in this configuration.

As described above, the physical shape of a hemofilter/dialyzer and the associated mounting mechanisms are present on the machine and serve as convenient, familiar methods to organize the fluid connections between the tubing set and the machine. In some embodiments, the intracorporeal therapy tubing set further comprises a shell in the general shape of a hemofilter or dialyzer, which provides the correct fluidic connections for the intracorporeal therapy mode, and further comprises the microbe/endotoxin filter within the volume of the shell. In one embodiment, this shell is pre-connected to the patient tubing lines. When this cartridge is installed, a reader on the dialysis machine can be configured to detect this intracorporeal configuration and the system can automatically configure the setup guidance and machine settings appropriately, such as by disabling the blood pump. This configuration can be configured to support both continuous flow intracorporeal therapies (such as continuous flow peritoneal dialysis), or tidal intracorporeal therapies, such as automated peritoneal dialysis, in which volumes of dialysate are sequentially delivered to, and withdrawn from the patient, typically while asleep. For tidal therapies, which only have a single access point, it would be beneficial to combine the two lines from going to the patient into a single line, for example, with a wye-style connector. Such a distinction could further be encoded into the identifier mechanism of the intracorporeal therapy tubing set, which would allow the machine to enable the correct therapy mode for the cartridge.

Figure 37:
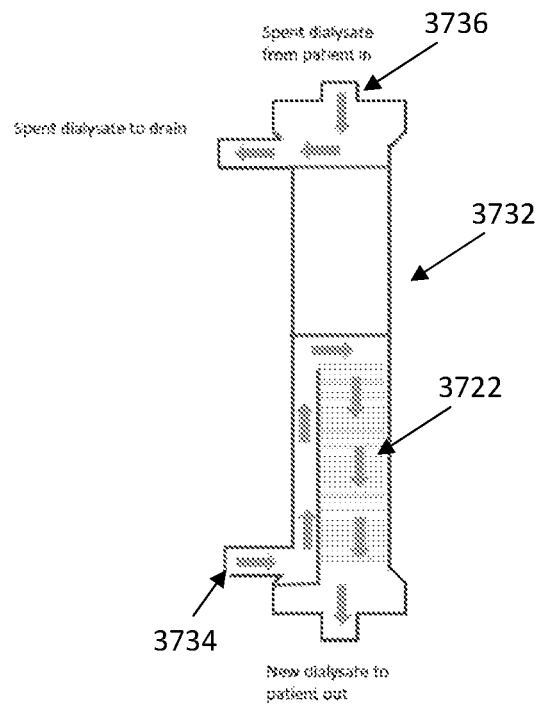

FIG. 37 illustrates one example of a dialyzer shell 3732 for use in the intracorporeal configuration described above. As described above, while a physical dialyzer isn't necessary for intracorporeal therapy, a shell dialyzer can be used to interface with the dialysis machine to enable all the proper fluidic connections in that configuration. Referring to FIG. 37, the dialyzer shell 3732 can include a new dialysate inlet 3734 configured to receive new dialysate from the dialysis system. In the illustrated example, the dialyzer shell can further include an integrated microbe/endotoxin filter 3722. However it should be understood that in other embodiments, the filter is not integrated into the shell, but instead is externally mounted like the example in FIG. 35B. Spent dialysate returns from the patient into the patient tubing set and back into the dialyzer shell at spent dialysate inlet 3736, where it can then be drained from the system.

As described above, the dialysis systems herein utilize pressure measurements on both the arterial and venous patient lines for a variety of functions and features. Described herein are novel and unique pressure measurement devices for accurately and conveniently measuring these pressures during treatment. These pressure measurement devices are configured to measure a pressure within a blood tubing set without the need to form fluidic seals between the dialysis machine and the blood tubing set. In some embodiments, the pressure measurement devices herein use a flexible diaphragm that the blood flows through on one side, and a pressure transducer configured to measure the physical deflection of the diaphragm which correlates to the pressure within the blood tubing set. Additionally, in some embodiments, the diaphragm can be constrained in space in a low-displacement state, and the physical force the diaphragm is measured by the pressure transducer. Such a configuration overcomes both the need for a fluidic seal and concerns about manufacturing tolerances.

If the diaphragm is constrained in a low-displacement state, as described above, the vast majority of the force to maintain equilibrium against the blood pressure is now applied by the constraining member. By quantifying the force in the constraining member, for example, with a load cell, the pressure in the blood can be measured. Furthermore, the pressure measurement device can be configured to measure both positive and negative gauge pressure in the blood. Measuring positive gauge pressure is straightforward, as this would cause the diaphragm to push against the constraining member. However, negative gauge pressure would typically cause the diaphragm to pull away from the constraining member. In one embodiment, the constraining member is configured to apply a preload to the diaphragm as the cassette-based blood tubing set is mounted to the dialysis machine. In this manner, when a negative pressure is produced, it merely reduces the force felt by the constraining member, rather than decoupling from it.

The present disclosure includes a pressure measurement device that includes a flow channel (such as a flow channel of a patient tubing set) with a flexible membrane coupled to a pressure sensing assembly. The pressure sensing assembly can be integrated with a temperature sensor configured to measure a temperature across the membrane. In some embodiments, the flow channel membrane is coupled to the pressure sensing assembly with magnetic coupling. The pressure measurement device can further include a physical shielding and/or preloading displacement absorption mechanism.

Figure 38A:
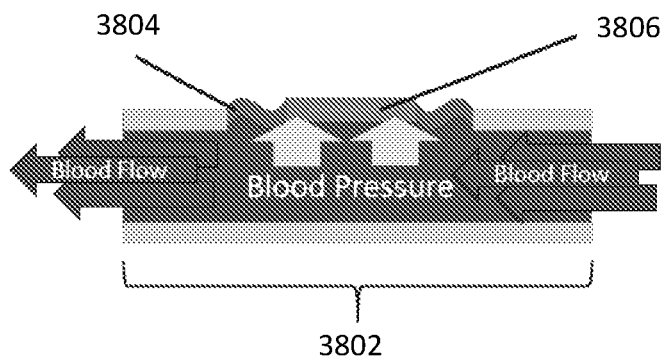
FIGS. 38A-38C illustrate one example of a pressure measurement system for measuring the pressure of a fluid within a patient tubing set.

FIG. 38A illustrates one example of a flow channel 3802 of a pressure measurement device. The flow channel can comprise, for example, a section of a patient blood tubing set of a dialysis system. In the illustrated example, the flow channel 3802 includes a section comprising a flexible diaphragm 3804. At least a portion of the flexible diaphragm 3804 can include an integrated magnetic core 3806. The flexible membrane positioned across the flow channel allows a displacement of the membrane to bring about a correlation between pressure within the flow channel and displacement due to the low modulus of elasticity of the membrane. The flexible diaphragm can be a small area to accommodate a stiffer membrane structure or it can be a more corrugated design to accommodate a structure with more compliance. The corrugated design is more forgiving and adds more compliance to the membrane to accommodate a high-pressure flow channel. Therefore, a balance in the design structure can be made to accommodate the most ideal configuration. The magnetic or ferrous core can be integrated within a central portion of the flexible diaphragm to create a ferrous base and a stiff flat surface for which to couple to the pressure transducer of the pressure measurement device. The stiff flat surface of the magnetic core gives the flexible membrane a more repeatable measurement of the displacement of the membrane due to the pressure fluctuations.

Figure 38B:
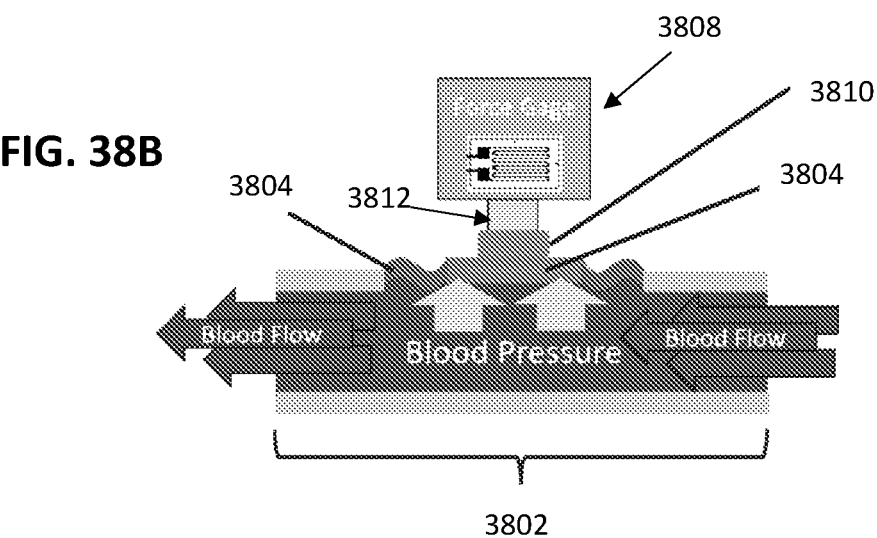

FIG. 38B illustrates an example of a pressure sensing device including a pressure transducer or force gauge 3808 magnetically coupled to the flexible diaphragm 3804 described above. As shown, the pressure measurement device can include a magnet 3810 configured to mate with the magnetic core 3806 of the flexible diaphragm 3804. The magnetic coupling mechanism is configured to translate displacement of the flexible membrane into a force reading by the pressure transducer. The pressure sensing device can further include a temperature sensor, such as a RTD, coupled to the interface between the flexible diaphragm and the shaft.

The force gauge or force transducer can include a threaded shaft 3812 disposed between the magnet and the transducer to act as a primary mounting mechanism that will accommodate both compression and tension operation. Once the fluid starts flowing through the flow channel, it is expected to create a negative and positive pressure within the flow channel that is to be translated into a force reading at the force transducer. The equilibrium point of the flow channel can be calibrated to be close to having a zero reading at rest to take advantage of the full-scale operation of the force gauge. The resulting force reading can then be input into a transfer function which can be converted into a pressure reading. In addition, the net zero reading of the pressure transducer can be directly compared to other pressure measurements of other sections of the dialysis system when the system is at rest. This can also be used as a redundancy check for the pressure measurements throughout operation.

Figure 38C:
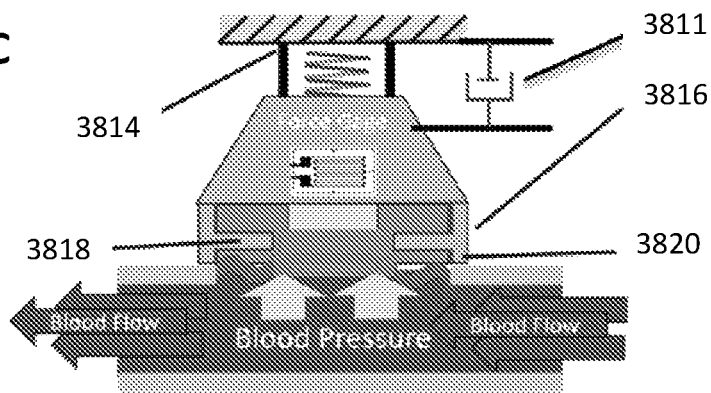

FIG. 38C is yet another embodiment of the pressure measurement device that further includes a compliant mount 3814 configured to stabilize and maintain a consistent amount of attachment between the pressure transducer and the flexible diaphragm, independent from the rest of the dialysis system. The compliant mount 3814 is configured to reduce any negative influences with neighboring components in patient tubing set/cartridge and front panel assembly of the dialysis system. This embodiment can further include an abutting member 3816 will have structural extensions 3818 (radial) and 3820 (axial) configured to mechanically attach to the flow channel as shown. The abutting member 3816 is designed and configured specifically to contact and hold the ends of the flow channel that connect to the flexible diaphragm. Additionally, the ends of the abutting member can also match the shape of the structure of the flexible diaphragm in order to secure the pressure transducer in translational directions.

The abutting member can be flush or slightly protrude the plane of the pressure transducer so as to put any structural strain of the structure onto the housing of the assembly, rather than on the force transducer itself. This also prevents damage to the threaded shaft due to user handling or cleaning. Furthermore, the abutting member can also absorb structural forces being applied onto the compliant mount which, in turn, would be adding to noise into pressure transducer. The goal is to make pressure readings from the flow channel onto the force transducer be independent of structural forces or adjacent mechanisms that may affect the reading.

The compliant mount 3814 can comprise, for example, a spring or other mechanism known in the art to produce a mechanical force bias, and can be configured to maintain a constant force strong enough to keep the flow channel coupled to the force transducer. It can include aligning pins to properly align and mount the abutting member described above. The compliant mount and the abutting member can be configured to restrain movement of the pressure transducer in a single translational degree of freedom to only allow for axial movement. For example, the compliant member can be mounted with two to three pins so as to constrain the other two translational and the three rotational degrees of freedoms. This allows pressure fluctuations to act only in the axial degree of freedom to allow for maximum sensitivity to force gauge readings.

The magnetic coupling of the device can create an attenuation due to the forces being applied onto the compliant mount and onto the flow channel. In one embodiment, an optional dampener 3811 can be used in conjunction with the compliant mount. As the pressure from the flow channel applies pressure on the compliant mount, the dampener can be configured slow the rate at which the compliant mount is being compressed. This would in turn, condense and attenuate the frequency response and help make the noise much more trivial to the pressure transducer. Because the dampening force is proportional to the rate of change of displacement, there would still be some slight attenuation, but the window of time and frequency amplitude becomes much more subdued with this embodiment.

Figure 39A:
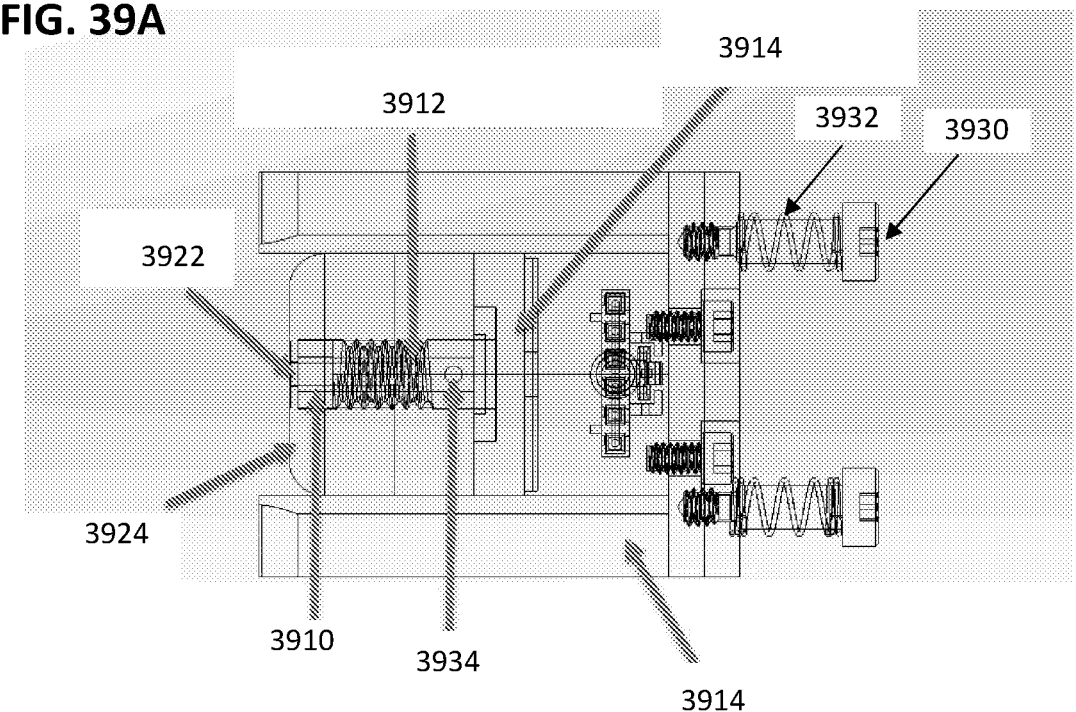
FIGS. 39A-39B illustrate two views of a pressure measurement device.
Figure 39B:
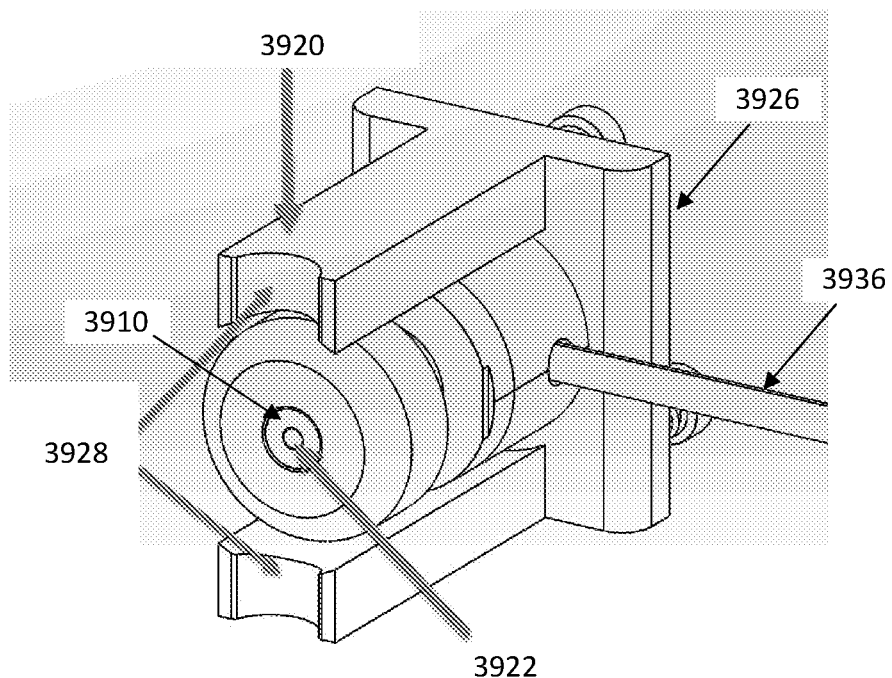

FIGS. 39A-39B illustrate another embodiment of a pressure sensing device including a compliant member. Referring to FIG. 39A, the pressure sensing device can include many of the same components as described above, including a force transducer or force gauge 3908, a threaded shaft 3912, a magnet 3910, and a compliant mount 3914. The pressure sensing device can further include a temperature sensor 3922 configured to contact the flexible diaphragm of the flow channel, and a shaft housing 3924 configured to surround and protect the threaded shaft. In the example of FIG. 39B, the temperature sensor 3922 can be disposed concentrically within the magnet 3910. A temperature sensor wire exit hole 3934 and conduit 3936 can be seen in FIGS. 39A and 39B, respectively.

As can be seen in FIG. 39B, the compliant mount can include a backing plate section 3926 and a plurality of axial extensions 3920. As described above, the axial extensions of the compliant mount can be configured to contact/hold portions of the flow path adjacent to the flexible diaphragm (e.g., normal tubing of the patient blood tubing set). The axial extensions can optionally include a cutout our shape 3928 configured to conform to the shape of the flow path (e.g., a concave surface configured to conform to the shape of a patient tubing set).

Referring back to FIG. 39A, the compliant mount can include one or more shoulder screws 3930 with springs 3932 coiled around the outer diameter of the screws. The spring is then be naturally compressed against the screw when mounted up against the backing plate 3926. The alignment of the shoulder screw to the backing plate hole (with the spring forces on the OD of the shoulder screws) can be tightly controlled to properly control the plane that the pressure transducer travels along. The movement of any direction outside the axial direction of the pressure transducer can therefore be virtually eliminated.

Figure 40A:
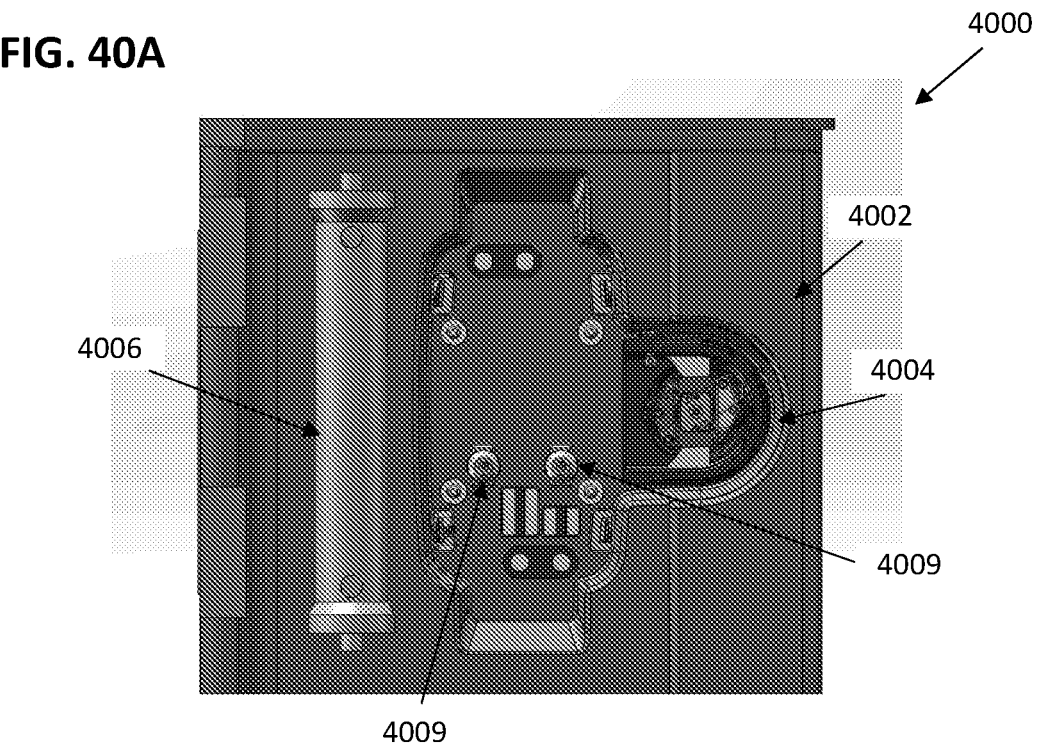
FIGS. 40A-40B illustrate the interface between a dialysis system and a cassette and patient tubing set.
Figure 40B:
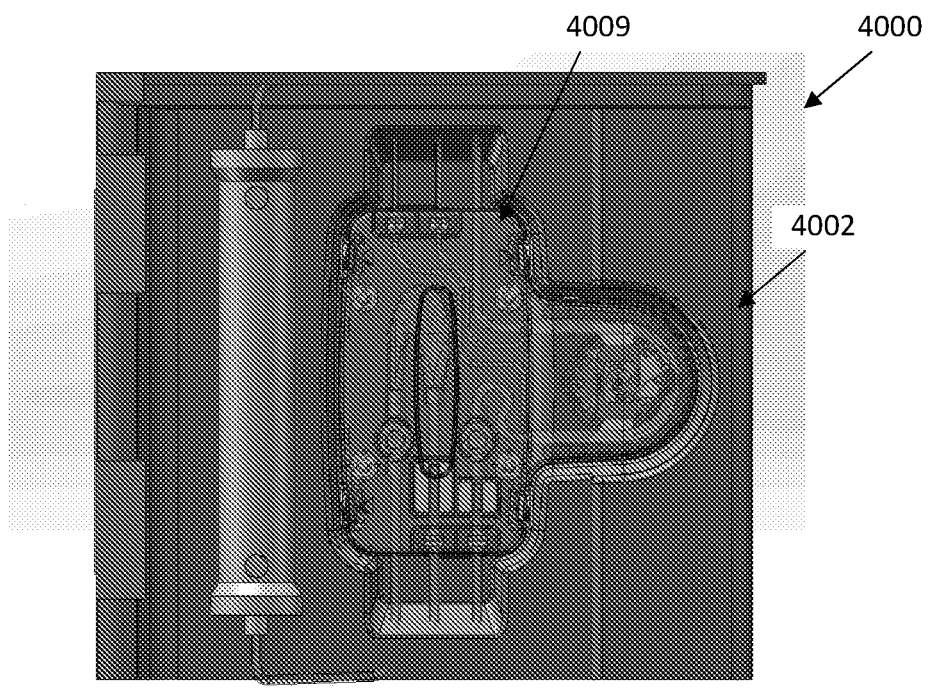

FIGS. 40A-40B illustrate two views of a cassette interface panel 4002 of a dialysis system 4000. The cassette interface panel provides the connections between the components of the dialysis system and a single-use cassette and patient tubing set which is used during dialysis therapy. FIG. 40A shows the cassette interface panel 4002 without the cassette and patient tubing set installed, and FIG. 40B shows the cassette and patient tubing set 4008 installed on the cassette interface panel. As shown in FIG. 40A, the dialysis system can include a blood pump 4004, a dialyzer 4006, and one or more pressure measurement devices 4009, such as the pressure measurement devices described above. As shown in FIG. 40B, the cassette and patient tubing set 4008 can including the blood tubing lines that interface with the dialysis system during therapy, and can further include other features described above such as an air removal chamber or air removal chamber.

The force transducer full scale range can be in the lower kg range. A full-scale range (including both tension and compression) can utilize up to 1-5 lbf range for the current application dialysis therapy with an extracorporeal therapy tubing set. This makes the pressure transducer very sensitive to any electrical noise, shift in center of gravity (CG), and installation orientation. To counteract this, an asymmetric three-hole bolt pattern will be utilized to mount the pressure sensing device. This can minimize impact to the center of gravity of the pressure transducer relative to the diaphragm. In addition, the asymmetric mounting pattern can reduce any type of error in installation that will negatively impact the force transducer.

Blood clotting is always a potential issue with dialysis using an extracorporeal circuit. Blood by nature is a complex colloidal, non-Newtonian, fluid that serves a variety of functions, one of which is to effectively clot when triggered to do so. With enough time in any extracorporeal circuit, even minor clotting effects could turn into treatment ending thrombosis. As the shift in dialysis moves towards home care, these treatments see a higher influence from clotting due to the increased time scale alone.

While the clotting cascade is complex as are the Naiver-Stokes equations, there are a few first order approximations that can be made to optimize blood flow conditions for reducing unwanted clotting. Controlling the blood flow profile to minimize clot forming conditions is one that can be aided by computational fluid dynamics (CFD). Stagnation point flow is defined as a flow region near a point in a flow field where the flow vectors diverge. These diverging vectors can produce regions of unwanted slow flow or areas vorticity. Low flow conditions will always be present due to the no-slip condition in fluid dynamics, however stagnation points in a flow field can be greatly reduced. These stagnation points come from a myriad of places, largely when flow field serves some alternate purpose such as being measured, diverted, or treated. In the past, the blood pathways were largely seen as subservient to the overall medical device such that the flow was optimized to the device's needs instead of the contrary.

The pressure measurement devices described above, particularly the location in the flow path with a flexible diaphragm, provide a place within the extracorporeal circuit that could be prone to initiating clothing. This is due to the need for an interface zone between the patient tubing line and the pressure transducer. As described above, the flexible diaphragm moves as a function of the circuit pressure, the pressure transducers on the other side are able to then measure line pressure. Specific design choices went into the size and shape of the flow channel in the pressure measurement devices to reduce flow recirculation below detectable limits. To achieve this, two factors were considered: maintaining the flow area while compensating for the effects of the boundary layer. A power function was used to balance the rate at which the flow path widens (to accommodate the pressure sensors) to estimate the rate at which the flow path height decreased while accounting for boundary layer effects. If the channel was narrowed too abruptly a back-pressure wave would be created and artificially restrict the flow as the fluid encountered a non-equivalent restriction. If the flow channel was narrowed too gradually excessive space and material would be required creating a larger cartridge and hence requiring more of the patient's blood for treatment. Internal geometric features have been further added to smooth out the internal surface transitions in the flow cannel to redirect any potential orthogonal flow vectors that may occur due to flow separation at the wall due to the expansion. This further helps reduce potential spots of flow recirculation. Due to the inertial effects of a fluid, flow channel aspect ratios were modified to compensate for the bends in the flow path that tended to cause the flow through the pressure zone to become off center thus creating local vortices.

A measure of improvement can be seen by looking at the reduction of the volume of fluid moving at a given rate. Fluid that is that is caught in vortex flow has no appreciable net velocity as does fluid that is subject to flow near stagnation points. By comparing slow moving volumes in the measurement area (excluding flows at or near the wall), the degree of improvement can be expressed in numbers. The pressure measurement channels of the present disclosure can have a slow flowing volume of 0.08 milliliters compared to upwards of 2 milliliters of slow flowing fluid in conventional designs. This represents over a 20 times reduction in the volume of at-risk fluid in the pressure measurement zone. By tailoring the dialysis circuit to the inherent properties of the blood, a flow path has been optimized to minimize clotting without the need for additional coatings decreasing cartridge volume and maintaining the same level of care as before.

FIG. 41 provides a detailed view of a cassette and patient tubing set 4102 installed on a dialysis system, and includes a view of components such as the cassette shell 4103, pressure sensing devices 4104, air removal chamber/venous drip chamber 4106, blood lines 4108, flow sensor(s) 4110, and pinch valves 4112. In some embodiments, the cassette and patient tubing set can include tubing couplers 4114 to join different types of tubing together.

The cassette and patient tubing set 4102 can include an asymmetrical clamshell design with two or more clamshell sections. In the illustrated example of FIG. 41, the cassette can comprise two clamshell sections, with a first clamshell section 4116 (illustrated as the dark boundary in FIG. 41) being larger than the second clamshell section 4118 (illustrated as the dotted line in FIG. 41). The second clamshell section 4118 can include molded flow channels, or potentially flow channels comprising tubing to direct the flow of blood or other fluids in the cassette. If molded flow channels are used, then when the clamshell sections are joined together by ultrasonic welding, thermal welding, laser welding, adhesion or any other process known in the art, the channels are fully formed and sealed. Along the boundary of the second clamshell section, the tubing can be joined or welded to the end of each of the internal flow paths. When the two clamshell sections are joined, sections of the larger clamshell section can overhang the tubing that is joined to the boundary of the smaller half. It should be understood that the flow channels may exist in either the small clamshell section or large clamshell section, or a partial section of the flow channels may be contained within each half. It should be further to understood that the smaller or larger clamshell sections may be further sub-divided into smaller sections, so long as the general structure, once assembled, still complies with this general description.

Features located at the boundary of the larger clamshell section may be used to capture the blood tubing as it exits the overall boundary of the cassette, to hold it in place. The sections of the larger clamshell section that overhang the tubing may be positioned over various interfaces between the tubing within the cassette and the dialysis system, such as the blood pump, pinch valves and flow sensors. For such interfaces, engagement sections on the engagement section may be incorporated to assist in tasks such as properly loading tubing into sensors, providing surfaces or features for which the valves can shut off flow, or provide protection to user's extremities from mechanical motions such as pinch valve actuation and blood pump motion. Other interfaces, such as the air removal chamber and pressure sensors, may be preferentially incorporated within the molded flow channels of the smaller clamshell section.

FIG. 42A illustrates a second (smaller) clamshell section 4218 of a cassette and patient tubing set 4202, and FIG. 42B illustrates a first (larger) clamshell section 4216 of the cassette and patient tubing set. The stars 4220 in FIG. 42A illustrate the transition between patient tubing and a molded flow path within the smaller clamshell section. In some embodiments, the cassette and patient tubing set can include tubing couplers 4214 to join different types of tubing together.

FIG. 42B illustrates engagement sections 4222, 4224, and 4226 within the first (larger) clamshell section 4216. These engagement sections can correspond with pinch valves and flow sensors of the dialysis system, for example. The tubing, generally contained under the engagement sections that are intended for interfacing, may be of special material or dimensions. For example, the tubing that interfaces with the blood pump of the dialysis system may be of larger inner and outer diameter than the tubing that comprises the majority of the flow path. In the configuration illustrated in FIGS. 42A-42B, the tubing that interfaces with the flow sensors and pinch valves is the same section of tubing, and may be engineered for properties that would make it suitable for such interfaces, such as ultrasound transmission properties, lubricity, and low force occlusion. The longer sections of tubing that carry fluid through the rest of the circuit, including to and from the patient, have different performance constraints, such as the need for higher kink resistance and cost per length. Therefore, two different types of tubing may be joined by couplers 4214 at or near the boundary of the larger clamshell section. The overall advantage and intention of this design is that all interfaces—sensors, valves and blood pump, can be made with a single motion, when the Cartridge is installed onto a mating panel of the dialysis equipment.

The engagement sections of the large clamshell section can serve the purpose of applying compressive force to tubing or sensors positioned below them. This compressive force can be tightly controlled. In theory, it is simple to use the top surface of a sensor channel to register a lid, or other structure, used to compress the tubing within the channel. This is practical when the motion of a hinged lid is relatively small compared to the size of the sensor, and it is possible to design precise latching mechanisms to hold the lid in place. However, in the application of the illustrated cassette, the pushing element, such as a ridge located on the engagement section that abuts the tubing, is more difficult to align because the approach motion is much larger, and the scale of a latching mechanism to hold the entire cassette in place may not have the same tolerancing capabilities as a lid directly mounted to the sensor itself. To overcome this limitation, instead of relying on precise positioning of a rigid lid, some compliance is introduced to the system, such that even with the gross positioning available during cassette installation, a consistent force of relatively small range can be applied to the tubing as it rests within the flow sensor channel.

Figure 43A:
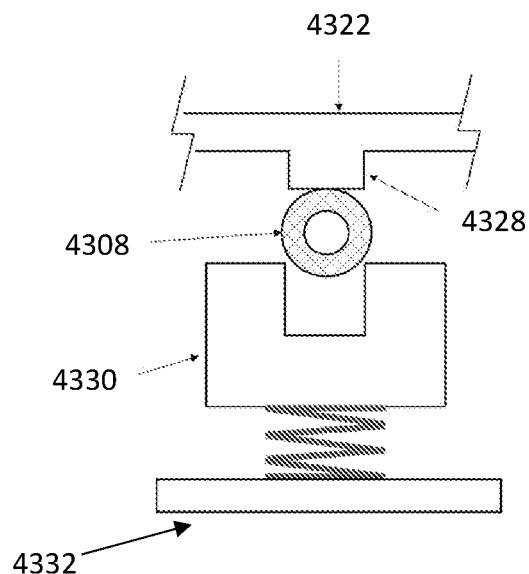
FIGS. 43A-43D illustrate embodiments for mounting patient tubing within one or more sensors such as flow sensors.
Figure 43B:
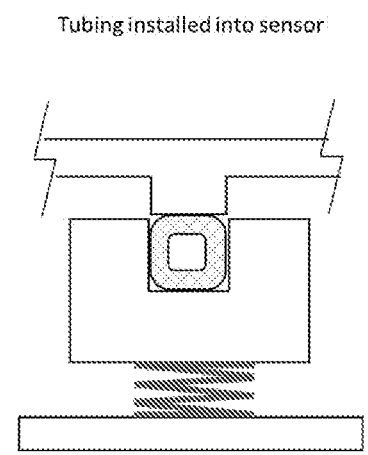
Figure 43C:
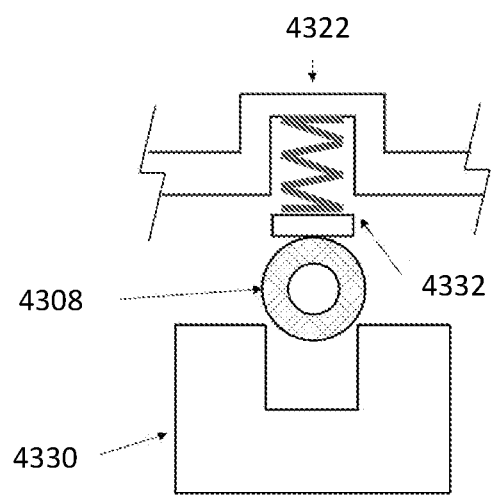
Figure 43D:
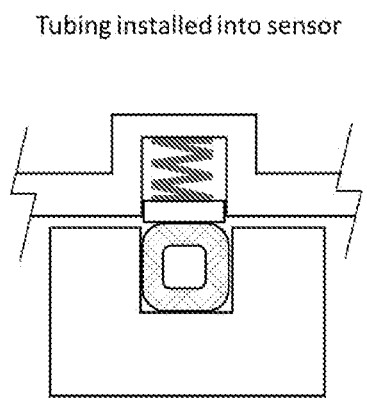

FIGS. 43A-43D shows embodiments of a tubing mounting configuration that relies on an engagement section of the cassette (e.g., engagement sections 4222, 4224, and 4226 from FIG. 42B) to assist in fully seating dialysis tubing within a channel of a flow sensor. Referring to FIG. 43A, engagement section 4322 can include an abutting ridge 4328 configured to press tubing 4308 into a groove or channel of a flow sensor 4330. FIG. 43B shows the tubing installed into the sensor. The flow sensor can mounted on a compliant mount 4332 that allows some travel as the tubing is pressed against the channel of the sensor. Only one sensor is illustrated, but it should be appreciated that the preferred embodiment comprises two or more such sensors, one on the arterial line, and one on the venous line. Due to the organization of the flow path, these sensors may be positioned directly next to one another, and in some embodiments may be contained within a single sensor block, with two separate flow channels and a single compliant mount. It can be also appreciated that the compliance of the system may be on the engagement section itself, as shown in FIGS. 43C-43D. In this example, the compliant mount 4332 is disposed within a channel configured to align with the tubing and the flow sensor channel. Although a representative coil spring is shown, the source of compliance may be a torsion spring, cantilever structure, or other structure known in the art to provide compliance.

Figure 44:
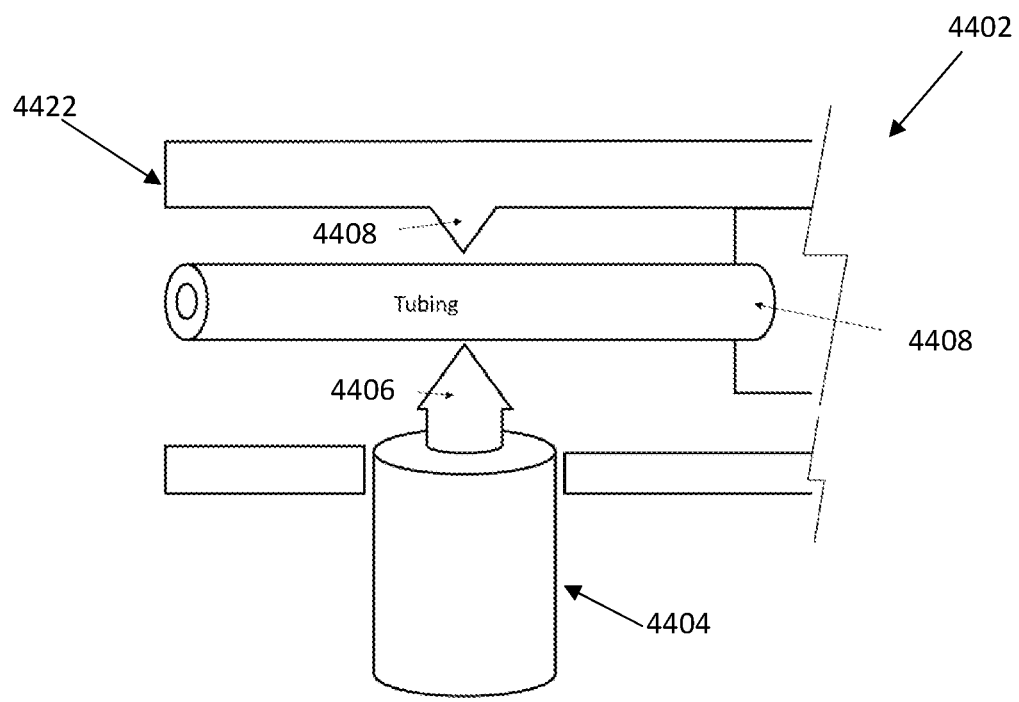
FIG. 44 is an example of a pinching mechanism configured to provide pinch valves for a patient tubing set.

FIG. 44 illustrates one embodiment of a pinch valve mechanism 4402 that relies on an engagement section 4422 of the cassette. Note that this view is rotated 90 degrees from the views described above. A linear actuator or solenoid 4404 can be connected to a first pinch mechanism 4406, which is driven against tubing 4408 welded into the smaller clamshell section, which sits under an engagement section 4422 the larger clamshell section. A second pinch mechanism 4408 is located on the engagement section of the larger clamshell section. The two pinch mechanisms may be of any configuration—such as opposing wedges, opposing rounds, offset wedges, offset rounds, wedge into flat surface, round into flat surface, or any other configuration known in the art.

In traditional hemodialysis machines, blood tubing sets are manually connected and strung through a complex series of pumps, valves and sensors. This approach is economical, as the blood tubing sets do not have any additional support structure, but the user inconvenience is such that typically only trained users are able to perform the setup. As described above, the dialysis system of the present disclosure uses a cartridge or cassette based approach to connecting the blood tubing sets to the dialysis machine, where the blood or patient tubing set is pre-routed through the cassette which is then placed over a cassette interface panel on the hemodialysis machine. This motion pre-aligns and creates all the valve, sensor and pump interfaces, which improves user convenience and helps enable setup by less skilled members of the population. However, install forces can be high with this approach, due to the need to form many interfaces. The present disclosure provides additional solutions to reduce the install forces needed for installation and further improve the installation and setup process.

Figure 45:
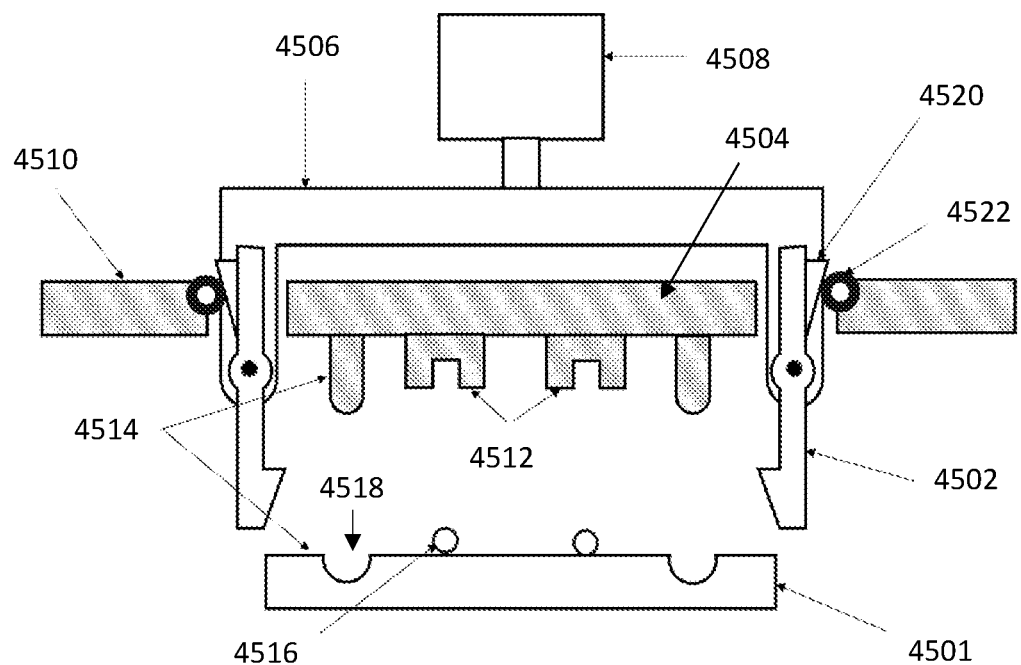
FIG. 45 is one example of a cartridge-style patient tubing set and a panel of a dialysis system.

Referring to FIG. 45, the dialysis systems described herein can include a mechanically-assisted latch scheme configured to assist with installation of a cartridge or cassette-style blood tubing set 4501. A series of latches or pivoting hinges 4502 can be arranged around a periphery (or central features) of a cassette interface panel 4504 of a dialysis machine. In the illustrated embodiment, these latches are all connected to a travel plate 4506 that sits behind the cassette interface panel, that allows these latches to move in and out perpendicular to the plane of the panel in unison. In other embodiments, these latches are not connected together, but have the ability to effect the same motion. The travel plate 4506 can be connected to linear actuator 4508, such as an electromechanical linear actuator, although other mechanisms configured to provide linear motion, such as manual mechanisms, or spring-loaded mechanisms can also be considered. As shown in FIG. 45, the latches can protrude through apertures in a fixed plate 4510, which contains interface points 4512 for the cartridge, such as sensors, pumps and valves, and optionally alignment features 4514. The interface points 4512 on the panel can align with cartridge-side interface points 4516 such as tubing, and the alignment features 4514 can be configured to align with corresponding cartridge-side alignment features 4518.

In the illustrated embodiment, the latches can pivot about a point, wherein the pivot motion is biased with a torsion spring or other mechanism, such that they can displace and allow passage a cartridge through them during install, and then pivot into place such that the cartridge is retained. Additionally, the latches comprise a ramp feature 4520, that in certain positions of displacement of the travel plate, engage with rollers 4522 mounted to the fixed plate in a manner that forces the latches to pivot against the bias torque, such that the latches effectively 'open', releasing a cartridge that was held by the latches.

Figure 46A:
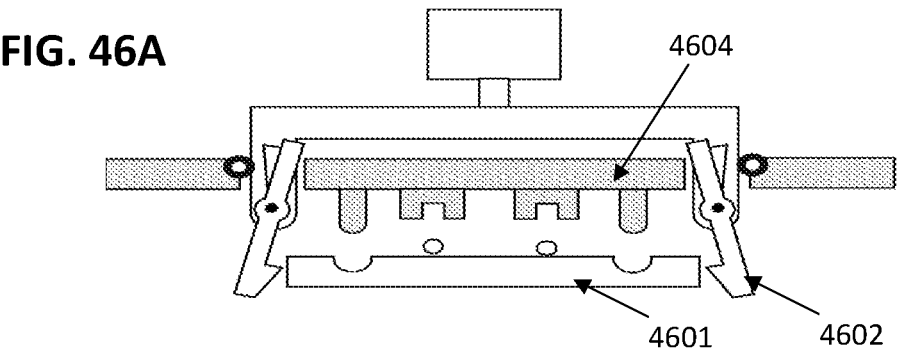
FIGS. 46A-46D illustrate the cartridge-style patient tubing set being loaded and unloaded onto the panel of the dialysis system.
Figure 46B:
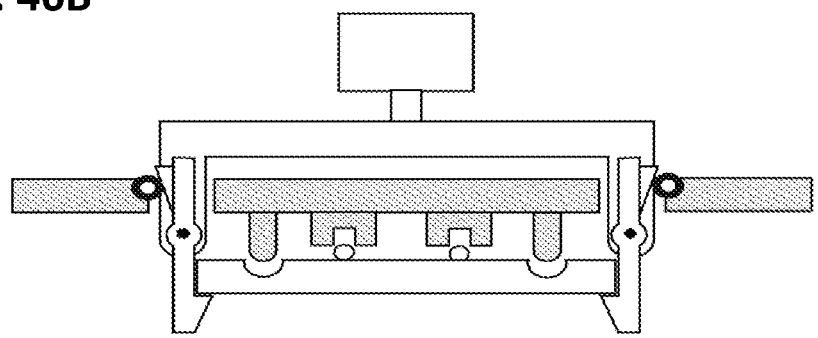

The loading and unloading of a cassette 4601 or cartridge-based tubing set onto a cassette interface panel 4604 of a dialysis system is shown in FIGS. 46A-46D. FIG. 46A shows the cartridge or cassette before it is inserted into the latches 4602. A user can place the cartridge into the latches 4602, which would pivot out of the way to allow the cartridge to be seated, requiring minimal force from the user. FIG. 46B shows the cartridge seated within the latches. It should be noted that none of the cartridge interfaces between, for example, sensors and patient tubing, (which may have high reaction forces) are fully made at this point.

Figure 46C:
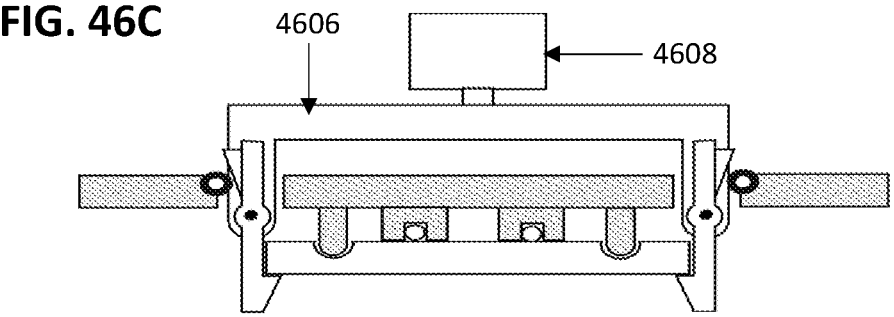
Figure 46D:
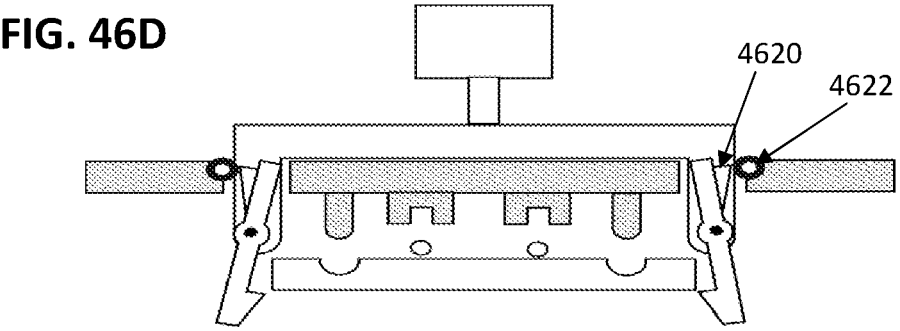

Once the cartridge is seated within the latches, referring to FIG. 46C, the linear actuator 4608 (or other mechanism) is configured to move the travel plate 4606, and therefore the cassette interface panel 4604, into the fully engaged or seated position. As is shown in FIG. 46C, in the fully seated position, the cassette patient tubing is fully installed within corresponding sensors, and the alignment features of the panel are fully aligned with and seated within cassette-side alignment features. The system may comprise sensors or detectors to inform the machine if or when the cartridge has been pressed onto the latches. The user may engage this step by a button (e.g. on the graphic user interface) or alternatively the machine may automatically engage this feature as soon as it detects the cartridge is installed. In this "engaged" position, all interfaces are fully made, and the forces needed to accomplish this is supplied by the linear actuator. The system may further comprise features limiting the distance the cartridge can move inward, to prevent fully creating interfaces until the travel plate is moved.

After entering the "engaged" position, the cartridge can be primed, and dialysis treatment can be conducted. At the conclusion of treatment, when the cartridge needs to be unloaded, the travel plate can be actuated by the linear actuator in the opposite direction into an "unload" position. In this position, the ramp features 4620 of the latches are configured to engage rollers 4622 which are connected to the fixed plate. This action causes the latches to pivot against their torsional bias, allowing the user to remove the cartridge or cassette. It should be appreciated that the roller/ramp configuration may be substituted for other mechanical devices that would function similarly. The travel plate may further comprise features that rest against the inward face of the cartridge which would serve to push the cartridge off of its interface points as the travel plate moves outwards.

Figure 47A:
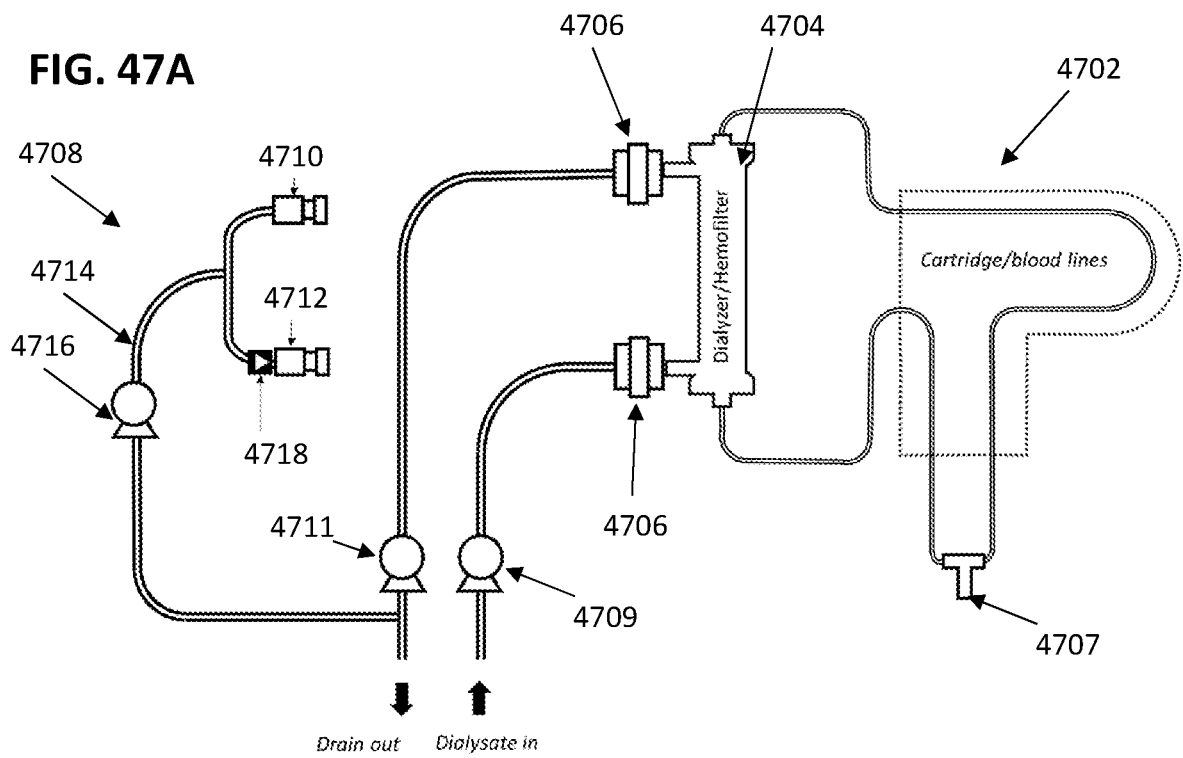

The embodiment of FIG. 35A-35B above described Hansen-style connectors for attaching a dialyzer to a source of dialysate. These connectors can further facilitate new techniques for removing priming fluid from the extracorporeal circuit after treatment and/or flushing or sanitizing a dialyzer or dialyzer lines prior to treatment. FIG. 47A illustrates a schematic diagram of an extracorporeal circuit 4702 of a dialysis system connected to a dialyzer 4704. As shown the venous and arterial lines of the extracorporeal circuit are coupled together with a union joint 4707. Hansen-style connectors 4706 can couple the dialyzer to a source of fresh dialysate and provide a fluid pathway to remove used dialysate to a drain. Pumps 4709 and 4711 are configured to provide new dialysate to the dialyzer and remove the spent or used dialysate to a drain.

FIG. 47A further illustrates a flush/drain pathway 4708 configured to flush the dialyzer lines and/or remove priming fluid from the extracorporeal circuit. The flush/drain pathway 4708 can include first connector 4710 and second connector 4712 fluidly coupled to drainage shunt 4714. A drainage pump 4716 can be configured to draw fluid into the drainage shunt 4714 and out through the drain via the first and/or second connectors. The flush/drain pathway 4708 can optionally include a one-way valve 4718 configured to allow fluid to pass only in a single direction through the second connector 4712.

Figure 47B:
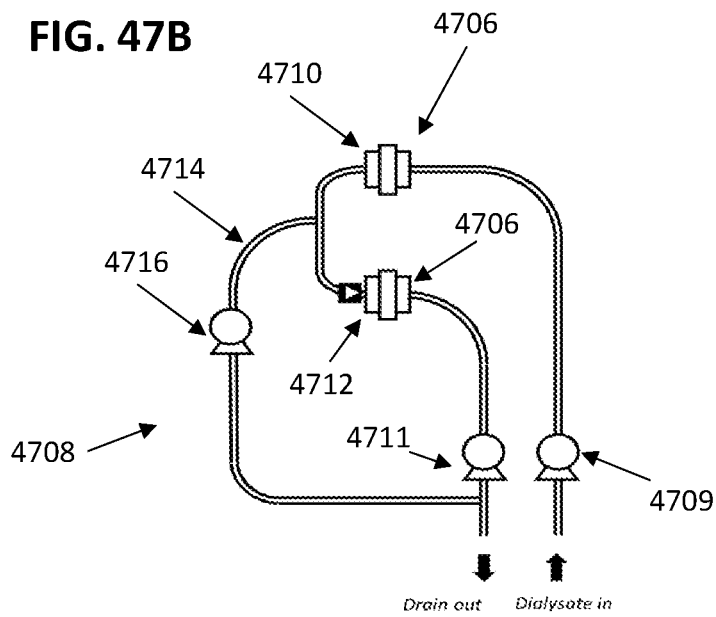

FIG. 47B illustrates a first configuration of the flush/drain pathway 4708 in which the Hansen-style connectors 4706 are connected to the first and second connectors 4710 and 4712 to form a continuous fluid pathway from the source of new dialysate to the drain. The drainage shunt 4714 branches off from the connectors 4710 and 4712. This configuration can be used to rinse or disinfect the dialysate lines. Flow of fluid can be created through the lines via pumps 4709, 4711, and 4716 to allow for disinfecting/flushing of the entire illustrated fluid circuit.

FIG. 47C illustrates the flush/drain pathway 4708 configured to remove priming fluid from the extracorporeal circuit. In this configuration, the union joint 4707 of the extracorporeal circuit has been connected to the first connector 4710 of the flush/drain pathway 4708. The second connector 4712 can be unattached to any other lines, and one-way valve 4718 can prevent fluid from leaking out of the second connector. The drainage pump 4716 can be operated to pull saline or priming fluid from the extracorporeal circuit into the flush/drain pathway 4708 via the first connector 4710 and remove the fluid through the drain, as shown. In some embodiments, the blood pump of the dialysis system may be used to run either forward or backwards, in tandem with the drainage pump 4716, to flow the priming fluid out of the extracorporeal circuit and out to drain. Once prime discard is complete, the arterial and venous lines can be disconnected from the union joint 4707 and attached to the patient's vascular access, to begin the dialysis treatment. Once treatment is completed, the Hansen-style connectors 4706 can be placed back on connectors 4710 and 4712, which automatically creates a rinse or disinfect path as described above.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A dialysate delivery subsystem of a dialysis system, comprising:
   a water supply port in fluid communication with a source of purified water;
   a concentrate connection cap having an outlet line in fluid communication with the dialysis machine, the concentrate connection cap being configured to mate with at least one of the water supply port, a powdered bicarbonate canister, or a pre-mixed liquid bicarbonate concentrate container;
   wherein in a first configuration, the powdered bicarbonate canister is connected to the water supply port, and the concentrate connection cap is connected to the powdered bicarbonate canister, and wherein purified water is delivered from the water supply port into the powdered bicarbonate canister to form a mixed bicarbonate solution which is then delivered to the dialysis system via the outlet line of the concentration connection cap;
   wherein in a second configuration, the concentrate connection cap is connected to the pre-mixed liquid bicarbonate concentrate container, and wherein a mixed bicarbonate solution is then delivered to the dialysis system via the outlet line of the concentration connection cap; and
   wherein in a third configuration, the concentrate connection cap is connected directly to the water supply port, and wherein purified water from the source of purified water is configured to flow through the concentration connection cap to flush out residual concentrates.

2. The dialysate delivery subsystem of claim 1, wherein in the second configuration, the water supply port is automatically closed.

3. The dialysate delivery subsystem of claim 1, wherein in the second configuration, a straw or conduit fluidly couples the concentrate connection cap to the pre-mixed liquid bicarbonate concentrate container.

4. The dialysate delivery subsystem of claim 1, wherein in the first configuration, the water supply port includes a selectively openable/closable valve mechanism.

5. The dialysate delivery subsystem of claim 1, further comprising a pump.

6. The dialysate delivery subsystem of claim 5, wherein in the first configuration, the pump is configured to pull purified water from the source of purified water into the powdered bicarbonate canister.

7. The dialysate delivery subsystem of claim 5, wherein in the first configuration, the pump is configured to pull mixed bicarbonate solution from the powdered bicarbonate canister into a patient tubing set of the dialysis system.

8. The dialysate delivery subsystem of claim 5, wherein in the second configuration, the pump is configured to pull mixed bicarbonate solution from the pre-mixed liquid bicarbonate concentrate container into a patient tubing set of the dialysis system.

9. The dialysate delivery subsystem of claim 1, wherein in the first configuration, the powdered bicarbonate canister includes a docking protrusion configured to mate with the water supply port.

10. The dialysate delivery subsystem of claim 1, wherein in the first configuration, the powdered bicarbonate canister includes mechanical fixation devices configured to cause the powdered bicarbonate canister to remain connected to the water supply port.

11. The dialysate delivery subsystem of claim 1, wherein in the first configuration, the powdered bicarbonate canister includes an inlet conduit configured to deliver purified water from the water supply port into the powdered bicarbonate canister.

12. The dialysate delivery subsystem of claim 1, wherein in the first configuration, the powdered bicarbonate canister includes an outlet conduit configured to deliver the mixed bicarbonate solution out of the canister through a canister outlet into the concentrate connection cap.

13. The dialysate delivery subsystem of claim 12, wherein the canister outlet includes an outlet filter and a hydrophobic filter for venting.

14. The dialysate delivery subsystem of claim 9, wherein a shutoff in the water supply port is automatically opened when the powdered bicarbonate canister is mated with the water supply port.

15. The dialysate delivery subsystem of claim 12, wherein the outlet conduit extends adjacent to a bottom portion of the powdered bicarbonate canister.

* * * * *